(12) United States Patent
Bonnamy et al.

(10) Patent No.: US 11,896,700 B2
(45) Date of Patent: Feb. 13, 2024

(54) PROCESS FOR TREATING KERATIN FIBERS USING AN ANHYDROUS COMPOSITION COMPRISING A COMPOUND OF AZOMETHINE TYPE COMPRISING TWO PYRAZOLOPYRIDINE UNITS AND AN AQUEOUS COMPOSITION

(71) Applicant: L'OREAL, Paris (FR)

(72) Inventors: Arnaud Bonnamy, Saint-Ouen (FR); Karen Teboul, Saint-Ouen (FR)

(73) Assignee: L'OREAL, Paris (FR)

( * ) Notice: Subject to any disclaimer, the term of this patent is extended or adjusted under 35 U.S.C. 154(b) by 1387 days.

(21) Appl. No.: 16/311,519

(22) PCT Filed: Jun. 21, 2017

(86) PCT No.: PCT/EP2017/065281
§ 371 (c)(1),
(2) Date: Dec. 19, 2018

(87) PCT Pub. No.: WO2017/220676
PCT Pub. Date: Dec. 28, 2017

(65) Prior Publication Data
US 2023/0137804 A1    May 4, 2023

(30) Foreign Application Priority Data

Jun. 23, 2016 (FR) .................................... 1655865

(51) Int. Cl.
| | | |
|---|---|---|
| A61Q 5/10 | (2006.01) | |
| A61K 8/49 | (2006.01) | |
| A61K 8/34 | (2006.01) | |
| A61K 8/73 | (2006.01) | |
| C09B 55/00 | (2006.01) | |

(52) U.S. Cl.
CPC .............. *A61K 8/494* (2013.01); *A61K 8/342* (2013.01); *A61K 8/731* (2013.01); *A61Q 5/10* (2013.01); *C09B 55/009* (2013.01); *A61K 2800/882* (2013.01)

(58) Field of Classification Search
CPC ........ A61K 8/494; A61K 8/342; A61K 8/731; A61K 2800/882; A61Q 5/10; C09B 55/009
USPC ......................................................... 8/426
See application file for complete search history.

(56) References Cited

U.S. PATENT DOCUMENTS

| | | |
|---|---|---|
| 2,798,053 A | 7/1957 | Brown |
| 2,923,692 A | 2/1960 | Ackerman et al. |
| 3,915,921 A | 10/1975 | Schlatzer, Jr. |
| 4,131,576 A | 12/1978 | Iovine et al. |
| 4,157,388 A | 6/1979 | Christiansen |
| 4,217,914 A | 8/1980 | Jacquet et al. |
| 4,237,243 A | 12/1980 | Quack et al. |
| 4,390,689 A | 6/1983 | Jacquet et al. |
| 4,509,949 A | 4/1985 | Huang et al. |
| 4,702,906 A | 10/1987 | Jacquet et al. |
| 4,719,282 A | 1/1988 | Nadolsky et al. |
| 5,089,578 A | 2/1992 | Valint et al. |
| 5,534,267 A | 7/1996 | Neunhoeffer et al. |
| 5,663,366 A | 9/1997 | Neunhoeffer et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

STIc Search Report dated Apr. 12, 2023.*

(Continued)

*Primary Examiner* — Eisa B Elhilo
(74) *Attorney, Agent, or Firm* — THE MARBURY LAW GROUP, PLLC

(57) ABSTRACT

The subject of the present invention is a process for treating keratin fibers using an anhydrous dye composition comprising at least one compound of azomethine type comprising two pyrazolopyridine units of formula (I) or (II) and an aqueous composition. The invention also relates to a kit comprising an anhydrous dyeing composition and an aqueous composition.

20 Claims, No Drawings

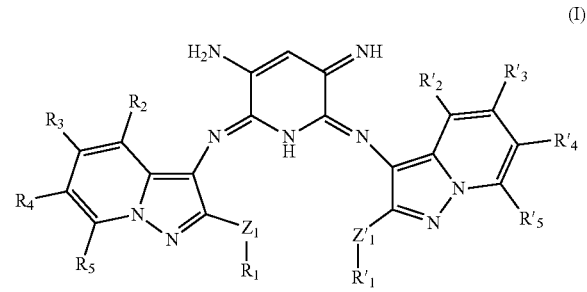

(I)

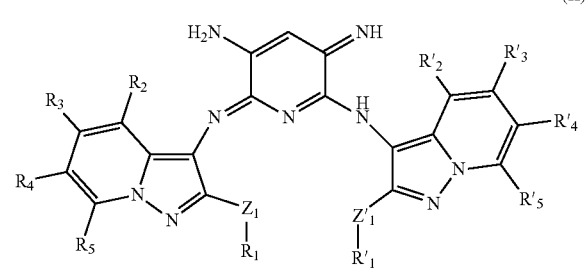

(II)

(56) References Cited

U.S. PATENT DOCUMENTS

| | | | |
|---|---|---|---|
| 5,792,221 | A | 8/1998 | Lagrange et al. |
| 6,099,592 | A | 8/2000 | Vidal et al. |
| 6,099,593 | A | 8/2000 | Terranova et al. |
| 6,312,677 | B1 | 11/2001 | Millequant et al. |
| 6,822,039 | B1 | 11/2004 | Monfreux-Gaillard et al. |
| 6,884,265 | B2 | 4/2005 | Vidal et al. |
| 7,060,110 | B2 | 6/2006 | Vidal et al. |
| 7,582,123 | B2 | 9/2009 | Fadli et al. |
| 2002/0095732 | A1 | 7/2002 | Kravtchenko et al. |
| 2003/0106169 | A1 | 6/2003 | Vidal et al. |
| 2004/0093675 | A1 | 5/2004 | Vidal et al. |
| 2004/0107513 | A1 | 6/2004 | Vidal et al. |
| 2004/0127692 | A1 | 7/2004 | David et al. |
| 2004/0143911 | A1 | 7/2004 | Vidal |
| 2004/0168263 | A1 | 9/2004 | Vidal |
| 2005/0039268 | A1 | 2/2005 | Plos et al. |
| 2005/0060815 | A1 | 3/2005 | Kravtchenko et al. |
| 2006/0053568 | A1 | 3/2006 | Fadli |
| 2010/0275390 | A1* | 11/2010 | Fadli ............ C07D 471/04 546/121 |

FOREIGN PATENT DOCUMENTS

| | | |
|---|---|---|
| DE | 4133957 A1 | 4/1993 |
| DE | 19543988 A1 | 5/1997 |
| EP | 0173109 A2 | 3/1986 |
| EP | 0503853 A2 | 9/1992 |
| EP | 0557203 A1 | 8/1993 |
| EP | 0714954 A2 | 6/1996 |
| EP | 0750899 A2 | 1/1997 |
| EP | 0770375 A1 | 5/1997 |
| EP | 1634574 A1 | 3/2006 |
| EP | 1792606 A1 | 6/2007 |
| EP | 1792903 A1 | 6/2007 |
| EP | 2246038 A1 | 11/2010 |
| FR | 2270846 A1 | 12/1975 |
| FR | 2416723 A1 | 9/1979 |
| FR | 2692572 A1 | 12/1993 |
| FR | 2733749 A1 | 11/1996 |
| FR | 2750048 A1 | 12/1997 |
| FR | 2807650 A1 | 10/2001 |
| FR | 2822693 A1 | 10/2002 |
| FR | 2822694 A1 | 10/2002 |
| FR | 2822696 A1 | 10/2002 |
| FR | 2822698 A1 | 10/2002 |
| FR | 2825625 A1 | 12/2002 |
| FR | 2825702 A1 | 12/2002 |
| FR | 2829926 A1 | 3/2003 |
| FR | 2844269 A1 | 3/2004 |
| FR | 2917737 A1 | 12/2008 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 98/44012 A1 | 10/1998 |
| WO | 00/31154 A1 | 6/2000 |
| WO | 00/68282 A1 | 11/2000 |
| WO | 02/078660 A1 | 10/2002 |
| WO | 02/100369 A2 | 12/2002 |
| WO | 02/100834 A1 | 12/2002 |
| WO | 2004/031173 A1 | 4/2004 |
| WO | WO 2004/031173 A1 * | 4/2004 ............ A61Q 5/065 |
| WO | 2016/097198 A1 | 6/2016 |

OTHER PUBLICATIONS

Fonnum, G., et al., "Associative Thickeners. Part I: Synthesis, Rheology and Aggregation Behavior," Colloid Polym. Sci., 271, (1993) pp. 380-389.

Hansen, C.M., "Hansen Solubility Parameters: A User's Handbook," CRC Press LLC, 2000, pp. 167-185.

Morishima, Yotaro, "Self-Assembling Amphiphilic Polyelectrolytes and their Nanostructures," Chinese Journal of Polymer Science, vol. 18, No. 40, (2000), pp. 323-336.

Noda, Tetsuya, et al., "Micelle Formation of Random Copolymers of Sodium 2-(Acrylamido)-2-Methylpropanesulphonate and a Nonionic Surfactant Macromonomer in Water as Studied by Fluorescence and Dynamic Light Scattering," Macromolecules 2000, 33, pp. 3694-3704.

Noda, Tetsuya et al., "Solution Properties of Micelle Networks Formed by Nonionic Surfactant Moieties Covalently Bound to a Polyelectrolyte: Salt Effects on Rheological Behavior," Langmuir 2000, 16, pp. 5324-5332.

Noda, Tetsuya, et al., "Stimuli-Responsive Amphiphilic Copolymers of Sodium 2-(Acrylamido)-2-Methylpropanesulphonate and Associative Macromonomers," Polym. Preprint, Div. Polym. Chem. 1999, 40(2), pp. 220-221.

International Search Report for counterpart Application No. PCT/EP2017/065281, dated Aug. 23, 2017.

Bagda, E., "The relation between surface tension and solubility parameter in liquids," Farbe Lack, 84, 1978, p. 212.

Crawford, Richard J., et al., "A replacement for Rubine dye for detecting cationics on keratin," Journal of the Society of Cosmetic Chemists, 31-(5), 1980, pp. 273-278.

\* cited by examiner

PROCESS FOR TREATING KERATIN FIBERS USING AN ANHYDROUS COMPOSITION COMPRISING A COMPOUND OF AZOMETHINE TYPE COMPRISING TWO PYRAZOLOPYRIDINE UNITS AND AN AQUEOUS COMPOSITION

CROSS REFERENCE TO RELATED APPLICATIONS

This is a national stage application of PCT/EP2017/065281, filed internationally on Jun. 21, 2017, which claims priority to French Application No. 1655865, filed on Jun. 23, 2016, both of which are incorporated by reference herein in their entireties.

The subject of the present invention is a process for treating keratin fibers using an anhydrous dye composition comprising at least one compound of azomethine type comprising two pyrazolopyridine units and an aqueous composition.

It is known practice to dye keratin fibers with dyeing compositions containing direct dyes. These compounds are colored and coloring molecules that have affinity for the fibers. It is known practice, for example, to use direct dyes of the nitrobenzene type, anthraquinone or nitropyridine dyes, and dyes of the azo, xanthene, acridine, azine or triarylmethane type.

These dyes are usually applied to fibers optionally in the presence of an oxidizing agent if it is desired to obtain simultaneous lightening of the fibers. Once the leave-on time has elapsed, the fibers are rinsed, optionally washed and dried.

The colorings resulting from the use of direct dyes are colorings that are often chromatic but are, however, only temporary or semi-permanent since the nature of the interactions that bind the direct dyes to the keratin fiber and their desorption from the surface and/or the core of the fiber are responsible for their weak dyeing power and their poor relative persistence with respect to washing or perspiration. These direct dyes are also generally light-sensitive since the resistance of the chromophore to photochemical attack is low, leading to fading of the coloring of the hair over time. The sensitivity of these dyes to light depends on their uniform distribution or their distribution as aggregates in and/or on the keratin fiber.

To obtain the same result, it is also possible to use the uncolored reduced form of these dyes and to apply it to the keratin fibers in the presence of an oxidizing agent in order to generate the colored and coloring oxidized form. The coloring obtained may then be faded out and then reformed rapidly by changing from one form to the other.

Thus, it is known from French patent application No. 2 917 737 to use compounds of azomethine type bearing a pyrazolinone unit and the reduced forms thereof to obtain a coloring on keratin fibers that can be faded out and then reformed readily.

The problem with some of these dyes concerns their stability in particular in the presence of water. When these dyes become hydrolyzed, they can produce colorings on the keratin fibers that are different than those obtained with the non-hydrolyzed forms. The colors can then become dull, iridescent, unnatural and unattractive. In some cases even gray turns into a color such as gray to violet pink. Added to this is a problem of packaging and storage of these dyes if they are in powder form. This is because it is then preferable for them to be in an inert medium, which represents an additional constraint.

The aim of the present invention is to provide novel coloring systems using direct dyes which make it possible to reversibly, gradually dye keratin fibers while at the same time producing good dyeing properties, and in particular the color of which does not change over time, and in the presence of water. In particular, the dyeing result does not change regardless of the storage time of the compositions used in the process according to the invention.

In particular, one of the aims of the present invention is to provide direct dyes that make it possible to obtain a strong, chromatic, esthetic, sparingly selective coloring with varied shades, which shows good resistance to the various attacking factors to which the hair may be subjected such as shampoos, light or sweat and the color of which does not change in an aqueous medium.

The applicant has thus discovered, surprisingly, that the process of the invention makes it possible to solve this (these) technical problem(s).

The process of the invention is a process for treating keratin fibers, in particular human keratin fibers, such as the hair, which consists in simultaneously mixing at least two compositions (1) and (2) wherein:
composition (1) is anhydrous and comprises one or more dyes chosen from dyes of azomethine type comprising two pyrazolopyridine units of formulae (I) and (II) below:

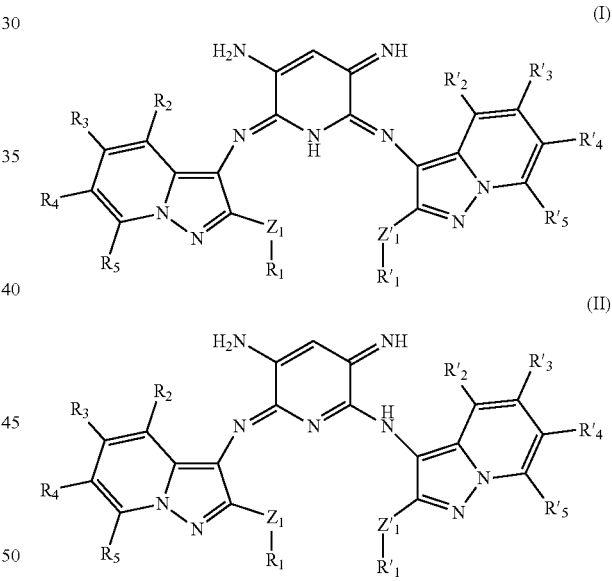

in which formulae (I) and (II):
$Z_1$ represents an oxygen atom or a group —N($R_6$)—;
$Z'_1$ represents an oxygen atom or a group —N($R'_6$)—;
when $Z_1$ represents —N($R_6$)— and/or $Z'_1$ represents —N($R'_6$)— then $R_1$ and $R_6$ and/or $R'_1$ and $R'_6$, respectively, may form, together with the nitrogen atom to which they are attached, an optionally substituted, 5- to 8-membered, optionally cationic, saturated, unsaturated or aromatic heterocycle;
$R_1$, $R'_1$, $R_6$, and $R'_6$ each independently represent:
a hydrogen atom,
a $C_1$-$C_{10}$ alkyl radical optionally interrupted with one or more non-adjacent heteroatoms, preferably oxygen, and/or optionally substituted, preferably with one or more groups chosen from i) hydroxyl, ii) optionally substituted, 5- to 8-membered, cationic or non-cationic, saturated, unsaturated or aromatic (hetero)cycle, iii) —N(R')R", iv) —N⁺R'R"R''' with R', R" and R''' each independently representing a $C_1$-$C_6$ alkyl group;

an optionally substituted, 5- to 8-membered, cationic or non-cationic, saturated, unsaturated or aromatic (hetero)cyclic radical;

in particular, $R_1$ and $R'_1$, which may be identical or different, preferably identical, represent a (poly)hydroxy($C_1$-$C_6$ alkyl), preferably hydroxy($C_1$-$C_6$ alkyl) group and $Z_1$ and $Z'_1$ represent an oxygen atom;

$R_2$, $R_3$, $R_4$, $R_5$, $R'_2$, $R'_3$, $R'_4$ and $R'_5$ each independently represent:

a hydrogen atom, an optionally substituted $C_1$-$C_4$ alkyl radical;

a group chosen from —$NH_2$, —$N(H)R_{10}$, —$N(R_{11})R_{12}$, OH and —$OR_9$, with $R_9$ and $R_{10}$ representing an optionally substituted, linear or branched $C_1$-$C_6$ alkyl, $R_{11}$ and $R_{12}$, which may be identical or different, representing an optionally substituted, linear or branched $C_1$-$C_6$ alkyl, it being possible for $R_{11}$ and $R_{12}$ to form, together with the nitrogen atom to which they are attached, a saturated, unsaturated or aromatic 5- to 8-membered heterocycle optionally containing one or more other heteroatoms or groups chosen from N, O, S, $S(O)_2$ and C(O), the heterocycle being optionally substituted, and/or $R_2$, $R_3$, $R_4$, $R_5$, $R'_2$, $R'_3$, $R'_4$ and $R'_5$ form, in pairs with adjacent radicals, an optionally substituted, saturated or unsaturated (hetero)cycle;

it being understood that when the compound of formula (I) or (II) is positively charged, then it comprises as many anionic counterions as cationic charges to achieve the electrical neutrality of the molecule; and composition (2) is aqueous, and comprises one or more ingredients chosen from:
i) hydrotropic solvents;
ii) anionic, cationic, nonionic, amphoteric or zwitterionic surfactants or mixtures thereof;
iii) anionic, cationic, nonionic, amphoteric or zwitterionic, optionally associative, optionally substantive, polymers, or blends thereof;

it being understood that composition (2) does not comprise any dye (I) or (II).

Under these conditions, the compounds of formula (I) or (II) as defined previously are used in composition (1) and are preferably soluble from 0.0000001% by weight to 1% by weight in the final mixture.

In addition, the mixing of compositions (1) and (2) is easy, fast and optimal. The shades obtained on the keratin fibers are optimal and stable, that is to say that even after a storage time of the two compositions (1) and (2) of 2 months at 45° C., the dyeing result does not change. Furthermore, the process of the invention makes it possible to obtain a gradual (for example from 1 to 5 applications) and uniform coloring without any color change as the applications are made. The treatment process of the invention makes it possible to obtain gradual colorings which become increasingly dark or strong over time.

Moreover, the process for treating keratin fibers according to the invention is used for dyeing keratin fibers with varied shades, in a strong, chromatic and esthetic manner, with sparingly selective coloring, which can readily fade and/or which can be easily re-dyed after fading. In addition, the colorings obtained using dyes (I) or (II) withstand the various attacking factors to which hair may be subjected, such as shampoos, light, sweat and permanent reshaping.

More particularly, the process of the invention makes it possible to obtain strong, chromatic colorings, at various pHs, better still at neutral and basic pH, and even more particularly at neutral pH. This process makes it possible, even in an aqueous medium, to obtain satisfactory colorings without observing any color change into unattractive colors.

Moreover the present invention provide novel method which is able to dye keratin fibers, especially natural keratin fibers such as hair, preferably white hair, in fundamental color i.e. in dark gray, blond, brown, brown chestnut, even black keratin fibers without necessarily using other hair dye than the azomethine type dye comprising two pyrazolopyridine units of formulae (I) and (II) of the invention. Dark colours obtained with dyes of the invention are very esthetic and natural looking.

For instance colours obtained on keratin fibers with dyes of the invention in the L* a* b* colorimetric system (wherein L* denotes the colour intensity, a* denotes the green/red colour axis, and b*: the blue/yellow colour axis) are such as colour data a * and b * are between 0 and 5.5, especially 0 and 5.

A subject of the present invention is also a multi-compartment device or kit for carrying out the process in accordance with the invention, comprising, in one compartment, at least one composition (1) as defined previously and, in another compartment, at least one aqueous composition (2) as defined previously.

Other subjects, characteristics, aspects and advantages of the invention will emerge even more clearly on reading the description and the examples that follow.

In the text hereinbelow, unless otherwise indicated, the limits of a range of values are included in that range, in particular in the expressions "between" and "ranging from . . . to . . . ".

The expression "at least one" used in the present description is equivalent to the expression "one or more".

In the context of the invention, unless otherwise mentioned, the term "alkyl radical" is intended to mean linear or branched alkyl radicals.

The saturated or unsaturated and optionally fused rings can also be optionally substituted.

The alkyl radicals are saturated, linear or branched, generally $C_1$-$C_{10}$ and particularly $C_1$-$C_{10}$ hydrocarbon-based radicals, preferably $C_1$-$C_6$ alkyl radicals, such as methyl, ethyl, propyl, butyl, pentyl and hexyl.

The alkenyl radicals are unsaturated, linear or branched $C_2$-$C_{10}$ hydrocarbon-based radicals, comprising at least one double bond, particularly $C_2$-$C_6$ alkenyl radicals such as ethylene, propylene, butylene, pentylene, 2-methylpropylene and decylene.

The alkynyl radicals are unsaturated, linear or branched $C_2$-$C_{10}$ hydrocarbon-based radicals, comprising at least one triple bond, particularly $C_2$-$C_6$ alkynyl radicals.

The alkoxy radicals are alkyl-oxy radicals with alkyl as defined above, preferably $C_1$-$C_{10}$ alkyl, such as methoxy, ethoxy, propoxy and butoxy.

The alkoxyalkyl radicals are preferably ($C_1$-$C_{20}$)alkoxy($C_1$-$C_{20}$)alkyl radicals, such as methoxymethyl, ethoxymethyl, methoxyethyl and ethoxyethyl.

For the purposes of the present invention, the term "interrupted" is intended to mean that the alkyl group is interrupted on the carbon-based chain of said alkyl with one or more heteroatoms. Examples that may be mentioned include -Ak-O-Ak", -Ak-N(R)-Ak", -Ak-O-Ak'—N(R)-Ak", -Ak-N(R)-Ak'—N(R)-Ak" or -Ak-O-Ak'-O-Ak", with Ak and Ak' representing $C_1$-$C_4$ alkylene groups and Ak" representing a $C_1$-$C_4$ alkyl group.

The halogens are preferably chosen from fluorine, chlorine, bromine and iodine atoms.

The "alkylcarbonyl" radicals are alkyl-carbonyl radicals with alkyl as defined previously, preferably $C_1$-$C_{10}$ alkyl, such as acetyl or propionyl.

The "alkoxycarbonyl" radicals are —O—C(O)-alkyl radicals with alkyl as defined previously, for instance acetate, propionate, citrate, tartrate, gluconate and lactate.

The "alkyl", "alkenyl", "cyclic" and "cycloalkyl" radicals, when they are substituted, are substituted with at least one substituent borne by at least one carbon atom, chosen from 1) a halogen atom, a group chosen from 2) hydroxyl; 3) oxo; 4) $C_1$-$C_2$ alkoxy; 5) $C_1$-$C_{10}$ alkoxycarbonyl; 6) $C_1$-$C_{10}$ alkylcarbonyl; 7) (poly)hydroxy($C_2$-$C_4$)alkyl; 8) (poly)hydroxy($C_2$-$C_4$)alkoxy; 9) amino; 10) quaternary ammonium —N$^+$R'R"R', M$^-$ for which R', R" and R''', which may be identical or different, represent a hydrogen atom or a $C_1$-$C_4$ alkyl group; and M$^-$ represents an anionic counterion, in particular a halide; 11) 5- or 6-membered heterocycloalkyl; 12) optionally cationic 5- or 6-membered heteroaryl, preferentially imidazolium, optionally substituted with a ($C_1$-$C_4$)alkyl radical, preferentially methyl; 13) amino substituted with one or two identical or different $C_1$-$C_6$ alkyl radicals optionally bearing at least: i) a hydroxyl group, ii) amino optionally substituted with one or two $C_1$-$C_3$ alkyl radicals, it being possible for said alkyl radicals to form, with the nitrogen atom to which they are attached, a saturated or unsaturated 5- to 7-membered heterocycle optionally comprising at least one other nitrogen or non-nitrogen heteroatom, iii) quaternary ammonium —N$^+$R'R"R''', M$^-$ for which R', R" and R''', which may be identical or different, represent a hydrogen atom or a $C_1$-$C_4$ alkyl group; and M$^-$ represents an anionic counterion, in particular a halide, iv) optionally cationic 5- or 6-membered heteroaryl, preferentially imidazolium, optionally substituted with a $C_1$-$C_4$ alkyl radical, preferentially methyl; 14) acylamino (—NR—C(O)—R') wherein the radical R is a hydrogen atom or a $C_1$-$C_4$ alkyl radical optionally bearing at least one hydroxyl group and the radical R' is a $C_1$-$C_2$ alkyl radical; 15) carbamoyl ((R)$_2$N—C(O)—) wherein the radicals R, which may be identical or different, represent a hydrogen atom or a $C_1$-$C_4$ alkyl radical optionally bearing at least one hydroxyl group; 16) alkylsulfonylamino (R'S(O)$_2$—N(R)—) wherein the radical R represents a hydrogen atom or a $C_1$-$C_4$ alkyl radical optionally bearing at least one hydroxyl group and the radical R' represents a $C_1$-$C_4$ alkyl radical, a phenyl radical; 17) aminosulfonyl ((R)$_2$N—S(O)$_2$—) wherein the radicals R, which may be identical or different, represent a hydrogen atom or a $C_1$-$C_4$ alkyl radical optionally bearing at least one hydroxyl group; 18) carboxyl in acid or salified form (preferably salified with an alkali metal or a substituted or unsubstituted ammonium); 19) cyano; 20) nitro; 21) nitroso; 22) phenoxy optionally substituted with one or more hydroxyl groups; 23) phenylcarbonyloxy optionally substituted with one or more hydroxyl groups; 24) phenyloxycarbonyl optionally substituted with one or more hydroxyl groups; and 25) a phenyl group optionally substituted with one or more hydroxyl groups.

The "aryl", "heterocyclic" or "heteroaryl" radicals or the aryl, heteroaryl or heterocyclic part of the radicals, when they are substituted, are substituted with at least one substituent borne by at least one carbon atom, chosen from: 1) halogen; 2) $C_1$-$C_{10}$ alkyl, preferably $C_1$-$C_8$alkyl, optionally substituted with one or more radicals chosen from the following radicals: i) hydroxyl, ii) $C_1$-$C_2$ alkoxy, iii) (poly)hydroxy($C_2$-$C_4$)alkoxy, iv) acylamino, v) amino substituted with two identical or different $C_1$-$C_4$ alkyl radicals optionally bearing at least one hydroxyl group or it being possible for the two radicals to form, with the nitrogen atom to which they are attached, a saturated or unsaturated 5- to 7-membered, preferably 5- or 6-membered, heterocycle optionally comprising another nitrogen or non-nitrogen heteroatom 3) hydroxyl; 4) $C_1$-$C_2$ alkoxy; 5) $C_1$-$C_{10}$ alkoxycarbonyl; 6) $C_1$-$C_{10}$ alkylcarbonyloxy; 7) (poly)hydroxy($C_2$-$C_4$)alkyl; 8) amino; 9) 5- or 6-membered heterocycloalkyl; 10) optionally cationic 5- or 6-membered heteroaryl, preferably imidazolium, optionally substituted with a ($C_1$-$C_4$)alkyl radical, preferentially methyl; 11) amino substituted with one or two identical or different $C_1$-$C_6$ alkyl radicals optionally bearing at least: i) hydroxyl, ii) amino optionally substituted with one or two $C_1$-$C_3$ alkyl radicals, it being possible for said alkyl radicals to form, with the nitrogen atom to which they are attached, a saturated or unsaturated 5- to 7-membered heterocycle optionally comprising at least one other nitrogen or non-nitrogen heteroatom, iii) quaternary ammonium —N$^+$R'R"R''', M$^-$ for which R', R" and R''', which may be identical or different, represent a hydrogen atom or a $C_1$-$C_4$ alkyl group; and M$^-$ represents an anionic counterion, in particular a halide, iv) optionally cationic 5- or 6-membered heteroaryl, preferentially imidazolium, optionally substituted with a $C_1$-$C_4$ alkyl radical, preferentially methyl; 12) quaternary ammonium —N$^+$R'R"R', M$^-$ for which R', R", R''' and M$^-$ are as defined previously; 13) acylamino (—N(R)—C(O)—R') wherein the radical R is a hydrogen atom or a $C_1$-$C_4$ alkyl radical optionally bearing at least one hydroxyl group and the radical R' is a $C_1$-$C_2$ alkyl radical; 14) carbamoyl ((R)$_2$N—C(O)—) wherein the radicals R, which may be identical or different, represent a hydrogen atom or a $C_1$-$C_4$ alkyl radical optionally bearing at least one hydroxyl group; 15) alkylsulfonylamino (R'S(O)$_2$—N(R)—) wherein the radical R represents a hydrogen atom or a $C_1$-$C_4$ alkyl radical optionally bearing at least one hydroxyl group and the radical R' represents a $C_1$-$C_4$ alkyl radical, a phenyl radical; 16) aminosulfonyl ((R)$_2$N—S(O)$_2$—) wherein the radicals R, which may be identical or different, represent a hydrogen atom or a $C_1$-$C_4$ alkyl radical optionally bearing at least one hydroxyl group; 17) carboxyl in acid or salified form (preferably salified with an alkali metal or a substituted or unsubstituted ammonium); 18) cyano; 19) nitro; 20) nitroso; 21) polyhaloalkyl, preferentially trifluoromethyl; 22) carboxyl; 23) phenylcarbonyloxy optionally substituted with one or more hydroxyl groups; 24) phenyloxycarbonyl optionally substituted with one or more hydroxyl groups; 25) phenyl optionally substituted with one or more hydroxyl or alkoxy groups; and 26) phenoxy.

The term "optionally substituted amino" is intended to mean an amino group which may bear one or two 1) identical or different $C_1$-$C_6$ alkyl radicals optionally bearing at least: i) a hydroxyl group, ii) an amino group optionally substituted with one or two $C_1$-$C_3$ alkyl radicals, said alkyl radicals or the two alkyl radicals form, with the nitrogen atom to which they are attached, a saturated or unsaturated, optionally substituted 5- to 7-membered heterocycle optionally comprising at least one other nitrogen or non-nitrogen heteroatom; 2) —C(O)(alkyl), the alkyl group possibly being substituted; 3) —C(O)O(alkyl), the alkyl group possibly being substituted; 4) —C(O)NH(alkyl), the alkyl group possibly being substituted; 5) —SO$_2$(alkyl), the alkyl group possibly being substituted.

The "cyclic" radicals are fused or non-fused, saturated or unsaturated, aromatic or non-aromatic monocyclic or polycyclic radicals, comprising from 4 to 30 carbon ring members, preferentially from 5 to 15 carbon atoms, optionally substituted with one or more atoms or groups as defined previously, in particular one or more alkyl, alkoxy, carboxyl, hydroxyl, amine or oxo groups.

The "aryl" radicals are fused or non-fused, monocyclic or polycyclic carbon-based radicals, preferentially comprising from 6 to 20 carbon atoms, and of which at least one ring is aromatic; preferentially chosen from phenyl, biphenyl, naphthyl, indenyl, anthracenyl and tetrahydronaphthyl radicals; more preferentially, the aryl radicals of the invention are phenyl radicals.

The "heterocyclic" radicals are fused or non-fused, saturated or unsaturated, aromatic or non-aromatic monocyclic or polycyclic, optionally cationic, 4- to 30-membered, preferentially 5- to 15-membered radicals, in at least one ring at least one ring member is a heteroatom, chosen in particular from O, N and S, preferably comprising from 1 to 6 heteroatoms, in particular O or N, optionally substituted with one or more atoms or groups as defined previously, in particular one or more alkyl, alkoxy, carboxyl, hydroxyl, amine or oxo groups.

When the heterocycle is cationic, then it bears a cationic charge inside the ring (endocyclic) or outside the ring (exocyclic), i.e. the heterocycle is substituted with a cationic group.

The "heteroaryl" radicals are fused or non-fused, preferentially 5- to 22-membered monocyclic or polycyclic radicals, comprising from 1 to 6 heteroatoms chosen from nitrogen, oxygen and sulfur atoms, and at least one ring of which is aromatic; preferentially, the heteroaryl radicals are chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salts thereof.

Among the heterocyclic radicals that may be used in the invention, mention may be made particularly of furyl, pyranyl, pyrrolyl, piperazinyl, piperidyl, morpholinyl, imidazolyl, pyrazolyl, pyridyl and thienyl groups. Preferably, the heterocyclic groups are fused heteroaryl groups such as benzofuryl, chromenyl, xanthenyl, indolyl, isoindolyl, quinolyl, isoquinolyl, chromanyl, isochromanyl, indolinyl, isoindolinyl, coumarinyl or isocoumarinyl groups, these groups possibly being substituted, in particular with one or more non-adjacent hydroxyl groups.

The "heterocycloalkyl" radicals are saturated heterocyclic radicals as defined previously, such as tetrahydrofuranyl, tetrahydropyranyl, piperazinyl, piperidyl or morpholinyl.

The cycloalkyl radicals are cyclic radicals as defined previously, preferably saturated C$_4$-C$_8$ monocyclic radicals, such as cyclobutyl, cyclopentyl or cyclohexyl. The cycloalkyl radicals may be substituted, in particular with alkyl, alkoxy, carboxylic acid, hydroxyl, amine and ketone groups.

The nitrogenous heterocycle(s) formed by R$_1$ and R$_6$, and/or R'$_1$ and R'$_6$ may contain one or more other heteroatoms, in particular a heteroatom chosen from N, O and S, one or more groups such as —S(O)—, —S(O)2- and —C(O)—, and combinations thereof, and more particularly O or N. They may moreover be optionally substituted, in particular as described above.

The term "anionic counterion" is intended to mean an anion or an anionic group derived from an organic or mineral acid salt which counterbalances the cationic charge of the dye; more particularly, the anionic counterion is chosen from: i) halides such as chloride or bromide; ii) nitrates; iii) sulfonates, including C$_1$-C$_6$ alkylsulfonates: Alk-S(O)$_2$O$^-$ such as methylsulfonate or mesylate and ethylsulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O—)$_2$—OHO=P(O$^-$)$_3$, HO—[P(O)(O$^-$)]$_w$—P(O)(O$^-$)$_2$ with w being an integer; xiv) acetate; xv) triflate; and xvi) borates such as tetrafluoroborate, xvii) disulfate (O=)$_2$S(O$^-$)$_2$ or SO$_4^{2-}$ and monosulfate HSO$_4^-$.

The anionic counterion, derived from the organic or mineral acid salt, ensures the electrical neutrality of the molecule; thus, it is understood that when the anion comprises several anionic charges, then the same anion may serve for the electrical neutrality of several cationic groups in the same molecule or else may serve for the electrical neutrality of several molecules; for example, a dye of formula (I) or (II) which contains two cationic chromophores may contain either two "singly charged" anionic counterions or a "doubly charged" anionic counterion such as (O=)$_2$S(O$^-$)$_2$ or O=P(O$^-$)$_2$—OH.

In formulae (I) and (II) above, when R$_1$, R'$_1$, R$_6$ and/or R'$_6$ represent a substituted alkyl radical, then the substituents are in particular chosen from halogen atoms, —OH, —OR$_9$, —NH$_2$, —N(H)R$_{10}$ or —N(R$_{11}$)R$_{12}$ radicals, saturated or unsaturated cyclic radicals optionally containing a heteroatom chosen from N, S and O, the ring itself possibly being substituted, wherein R$_9$, R$_{10}$, R$_{11}$ and R$_{12}$, which may be identical or different, represent a saturated linear or branched C$_1$-C$_6$ and preferably C$_1$-C$_4$ alkyl radical, such as methyl or ethyl. Preferably, mention may be made of —OH, —OR'$_9$, —NH$_2$, —N(H)R'$_{10}$ or —N(R'$_{11}$)R'$_{12}$ radicals and cyclic radicals of the imidazole, piperazine, pyrrolidine, pyridine, piperidine, morpholine and pyrimidine type.

According to a particular embodiment of the invention, the compounds of formula (I) or (II) above are such that Z$_1$ and Z'$_1$, which may be identical or different, represent an oxygen atom, a radical —N(R$_6$)— and a radical —N(R'$_6$)— forming with R$_1$ and R'$_1$, respectively, a cationic or non-cationic heterocycle, such as piperazinyl, piperazinium, imidazolyl, pyrrolidinyl, pyridyl, morpholinyl, morpholinium, piperidyl or piperidinium, preferentially piperazinyl or piperazinium optionally substituted in particular with one or more C$_1$-C$_4$ alkyl groups such as methyl.

The radicals R$_6$ and R'$_6$ may be chosen from a hydrogen atom; a C$_1$-C$_6$ alkyl radical and a C$_1$-C$_6$ alkyl radical substituted with one or more hydroxyl groups. According to this embodiment, Z$_1$ and Z'$_1$ preferably represent an oxygen atom or an NH radical.

According to the invention, the radicals R$_1$ and R'$_1$ may be chosen from the following groups: i) C$_1$-C$_6$ alkyl; ii) C$_1$-C$_{10}$ alkyl substituted with one or more hydroxyl groups; iii) C$_1$-C$_6$ alkyl substituted with one or more amino or (di)(C$_1$-

$C_4$) alkylamino groups such as dimethylamino; iv) $C_1$-$C_6$ alkyl substituted with a nitrogenous heterocycle, for example piperazinyl, imidazolyl, pyrrolidinyl, morpholinyl or piperidyl; v) —[(CH$_2$)$_m$—O]$_p$-L-Y with p=1, 2 or 3, preferably 1 or 2, m=1, 2 or 3, preferably 2, L denoting a linear or branched, saturated $C_1$-$C_6$ divalent hydrocarbon-based group, and Y denoting a hydroxyl group or a hydrogen atom.

Preferably, the radicals $R_1$ and $R'_1$ represent a $C_1$-$C_6$ alkyl group such as a methyl, ethyl, n-propyl, isopropyl or tert-butyl radical; a $C_1$-$C_6$ alkyl radical substituted with a hydroxyl group such as a hydroxyethyl or hydroxypropyl radical; a $C_1$-$C_6$ alkyl radical substituted with a di($C_1$-$C_4$) alkylamino such as a dimethylaminoethyl or dimethylaminopropyl radical; a $C_1$-$C_6$ alkyl radical substituted with a nitrogenous heterocycle chosen from imidazolyl, pyrrolidinyl, piperidyl, morpholinyl and piperazinyl, these heterocycles possibly being substituted; or a radical —[(CH$_2$)$_m$—O]$_p$-L-Y with m=2, p=1 or 2, L denoting an ethylene or isopropylene radical, and Y denoting a hydroxyl radical or a hydrogen atom.

According to the particular embodiment wherein $Z_1$ and $Z'_1$ denote, respectively, a radical —$NR_6$ and —$NR'_6$ with $R_1$ and $R_6$ and $R'_1$ and $R'_6$ together forming a heterocycle with the nitrogen atom to which they are attached, the heterocycle is preferentially chosen from imidazolyl, piperazino, pyrrolidino, piperidino and morpholino, these heterocycles possibly being substituted, in particular with one or more $C_1$-$C_4$ alkyl or hydroxyl radicals.

According to a particular embodiment of the invention, the compounds of formulae (I) and (II) are such that $R_2$, $R'_2$, $R_3$, $R'_3$, $R_4$, $R'_4$, $R_5$ and $R'_5$ independently represent a hydrogen atom or a $C_1$-$C_4$ alkyl radical such as methyl, ethyl, propyl, isopropyl, butyl or tert-butyl, or $R_4$ and $R_5$ and $R'_4$ and $R'_5$ together form a 5- to 8-membered ring. Preferably, $R_2$, $R'_2$, $R_3$, $R'_3$, $R_4$, $R'_4$, $R_5$ and $R'_5$ independently represent a hydrogen atom or a $C_1$-$C_4$ alkyl radical such as methyl, ethyl, propyl, isopropyl, butyl or tert-butyl.

In the context of the invention, the term "derivative of formula (I) and/or (II)" is intended to mean all mesomeric, tautomeric or optical or geometrical isomer forms, or leuco forms.

The term "addition salts" is intended to mean the salts of physiologically acceptable organic or mineral acids of the compounds of formula (I) and/or (II).

The compounds of formulae (I) and/or (II) may be optionally salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

Moreover, the addition salts that may be used in the context of the invention are also chosen from addition salts with a cosmetically acceptable base such as the basifying agents as defined below, for instance alkali metal hydroxides such as sodium hydroxide, potassium hydroxide, aqueous ammonia, amines or alkanolamines.

The compounds of formula (I) or (II) may also be in the form of solvates, for example a hydrate or a solvate of a linear or branched alcohol such as ethanol or isopropanol.

The present invention makes it possible in particular to rapidly obtain chromatic colorings that withstand the various attacking factors to which hair may be subjected, in particular shampoos and light, which can be faded out and then reformed just as quickly.

The compounds of formula (I) and/or (II) are colored and coloring species.

The compounds of formulae (I) and (II) are preferably symmetrical, i.e. $R_1$ represents the same radical as $R'_1$; the same is true for $R_2$ and $R'_2$, $R_3$ and $R'_3$, $R_4$ and $R'_4$, $R_5$ and $R'_5$, $R_6$ and $R'_6$, and $Z_1$ and $Z'_1$.

According to another particular embodiment of the invention, the compounds of formulae (I) and (II) are non-cationic.

According to a particular embodiment, the azomethine dyes bearing two pyrazolopyridine units are chosen from the symmetrical compounds of formula (I') or (II') below, and also the leuco forms, optical isomers, geometrical isomers and tautomers thereof, the addition salts thereof with an acid or a base and the solvates thereof such as hydrates:

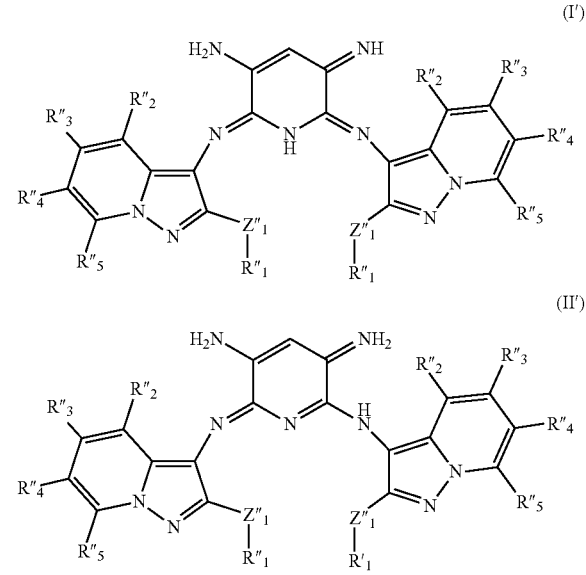

in which formulae (I') and (II'):
$Z''_1$ is chosen from an oxygen atom and a group —N(R''$_6$)—;
when $Z''_1$ represents —N(R''$_6$)—, then R''$_1$ and R''$_6$ may form, together with the nitrogen atom to which they are attached, an optionally substituted, 5- or 6-membered, saturated, unsaturated or aromatic heterocycle;
R''$_1$ represents a $C_1$-$C_6$ alkyl radical, optionally interrupted with one or more non-adjacent oxygen atoms, and/or optionally substituted with:
a hydroxyl radical;
a di($C_1$-$C_4$)alkylamino radical,
a heterocycle optionally substituted with one or more $C_1$-$C_4$ alkyl and/or hydroxyl radicals and chosen from pyrrolidine, piperidine, morpholine, piperazine and imidazole;
R''$_6$ represents:
a hydrogen atom,
a $C_1$-$C_{10}$ alkyl radical optionally substituted with a hydroxyl radical;
R''$_2$, R''$_3$, R''$_4$ and R''$_5$ each independently represent:
a hydrogen atom,
a $C_1$-$C_4$ alkyl radical.

According to a particular embodiment, the compound(s) of formula (I') or (II') are such that, when $Z''_1$ represents an oxygen atom, R''$_1$ denotes a linear or branched $C_1$-$C_6$ alkyl radical, a $C_1$-$C_6$ hydroxyalkyl radical; a di($C_1$-$C_4$ alkyl)

amino($C_1$-$C_6$ alkyl) radical; a radical —[($CH_2$)$_{m'}$—O]$_{p'}$-L'-Y' with p'=1, 2, 3, preferably 1 or 2, m'=2 or 3, L' denoting a saturated linear $C_1$-$C_6$ divalent hydrocarbon-based radical, and Y' denoting a hydroxyl radical or a hydrogen atom; an alkyl radical substituted with a heterocycle chosen from pyrrolidinyl, piperidyl, morpholinyl, piperazinyl and imidazolyl, said heterocycle being optionally substituted with one or more $C_1$-$C_4$ alkyl radicals such as methyl, or hydroxyl. Better still, R'$_1$ denotes a linear or branched saturated $C_1$-$C_6$ alkyl radical, such as a methyl, ethyl, n-propyl, isopropyl or tert-butyl radical; a $C_1$-$C_6$ hydroxyalkyl radical such as a hydroxyethyl or hydroxypropyl radical; a dimethylaminoethyl or dimethylaminopropyl radical; a radical —[($CH_2$)$_2$—O]$_{p'}$-L'-Y' with p'=1 or 2, L' denoting a saturated, linear, $C_1$-$C_6$ divalent hydrocarbon-based radical, and Y' denoting a hydroxyl radical or a hydrogen atom such that -L'-Y' denotes an isopropyl or ethyl radical; or an ethyl or propyl radical substituted with a heterocycle chosen from pyrrolidinyl, piperidyl, morpholinyl, piperazinyl and imidazolyl, said heterocycle being optionally substituted with one or more $C_1$-$C_4$ alkyl radicals such as methyl, or hydroxyl.

According to a particular embodiment of the invention, the compound(s) of formula (I') or (II') are such that, when Z"$_1$ represents NH, R"$_1$ denotes a $C_1$-$C_6$ hydroxyalkyl radical, a di($C_1$-$C_4$ alkyl)amino($C_1$-$C_6$ alkyl) radical, an alkyl radical substituted with a heterocycle chosen from pyrrolidinyl, piperidyl, morpholinyl, piperazinyl and imidazolyl, said heterocycle being optionally substituted with one or more $C_1$-$C_4$ alkyl radicals such as methyl, or hydroxyl.

According to another embodiment, when Z"$_1$ represents —N(R"$_6$)—, R"$_1$ and R"$_6$ each independently denote a $C_1$-$C_6$ alkyl radical or a $C_1$-$C_6$ hydroxyalkyl radical, and preferably R'$_1$ and R'$_6$ are identical.

According to another embodiment, when Z"$_1$ is —N(R"$_6$)— and when R"$_1$ forms a ring with R"$_6$, this ring is chosen from pyrrolidinyl, piperidyl, morpholinyl and piperazinyl rings optionally substituted with one or more $C_1$-$C_4$ alkyl and/or hydroxyl radicals.

As examples of dyes of formula (I), (II), (I') and/or (II'), mention may be made of the compounds presented below:

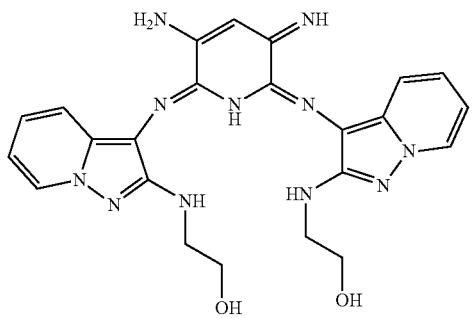

2,2'-[(5-amino-3-iminopyridine-2,6-(1H,3H)-diylidene)bis(nitrilopyrazolo[1,5-a]pyridine-3,2-diylimino)]diethanol

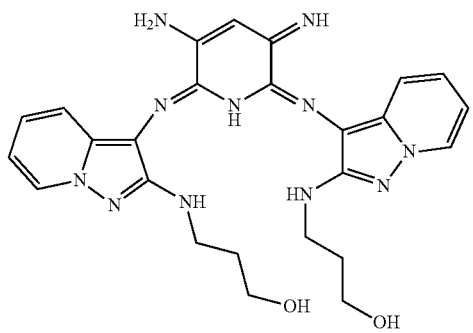

3,3'-[(5-amino-3-iminopyridine-2,6-(1H,3H)-diylidene)bis(nitrilopyrazolo[1,5-a]pyridine-3,2-diylimino)]dipropan-1-ol

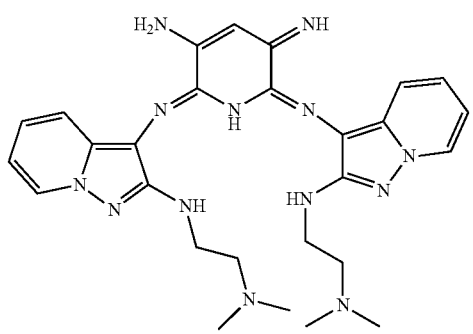

N3,N3'-(5-amino-3-iminopyridine-2,6-(1H,3H)-diylidene)bis{N2-[2-(dimethylamino)ethyl]pyrazolo[1,5-a]pyridine-2,3-diamine}

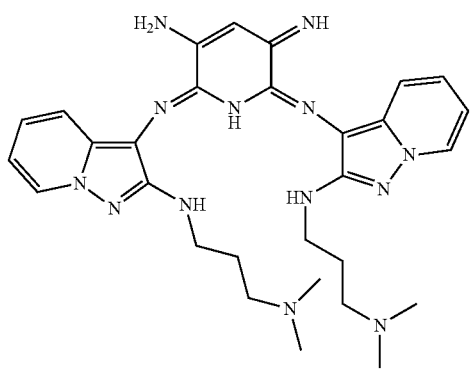

N3,N3'-(5-amino-3-iminopyridine-2,6-(1H,3H)-diylidene)bis{N2-[3-(dimethylamino)propyl]pyrazolo[1,5-a]pyridine-2,3-diamine}

-continued

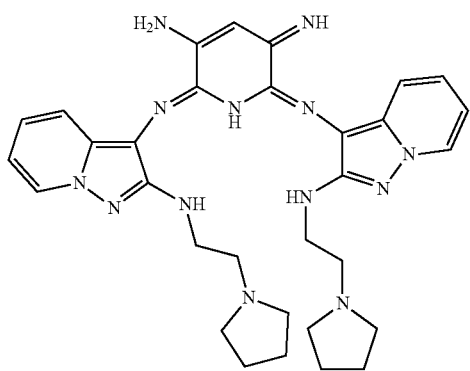

N3,N3'-(5-amino-3-iminopyridine-2,6-(1H,3H)-diylidene)bis{N2-[2-(pyrrolidin-1-yl)ethyl]pyrazolo[1,5-a]pyridine-2,3-diamine}

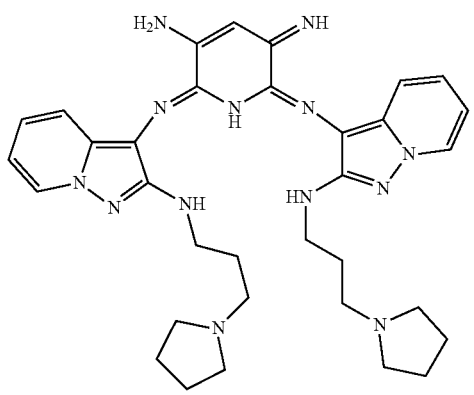

N3,N3'-(5-amino-3-iminopyridine-2,6-(1H,3H)-diylidene)bis{N2-[3-(pyrrolidin-1-yl)propyl]pyrazolo[1,5-a]pyridine-2,3-diamine}

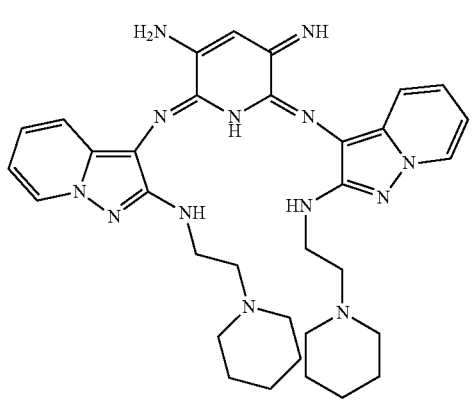

N3,N3'-(5-amino-3-iminopyridine-2,6-(1H,3H)-diylidene)bis{N2-[2-(piperidin-1-yl)ethyl]pyrazolo[1,5-a]pyridine-2,3-diamine}

-continued

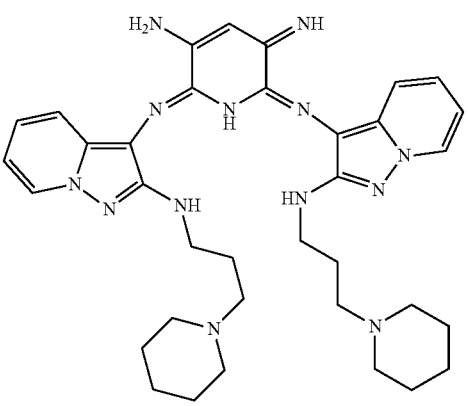

N3,N3'-(5-amino-3-iminopyridine-2,6(1H,3H)-diylidene)bis{N2-[3-(piperidin-1-yl)propyl]pyrazolo[1,5-a]pyridine-2,3-diamine}

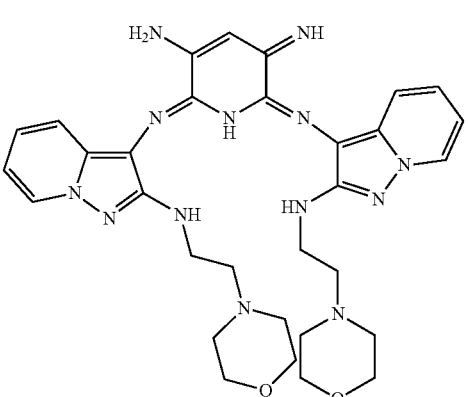

N3,N3'-(5-amino-3-iminopyridine-2,6-(1H,3H)-diylidene)bis{N2-[2-(morpholin-4-yl)ethyl]pyrazolo[1,5-a]pyridine-2,3-diamine}

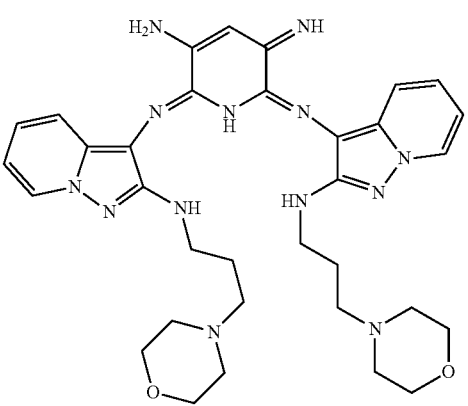

N3,N3'-(5-amino-3-iminopyridine-2,6-(1H,3H)-diylidene)bis{N2-[3-(morpholin-4-yl)propyl]pyrazolo[1,5-a]pyridine-2,3-diamine}

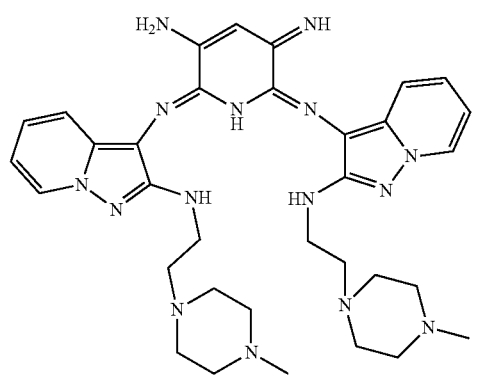

N3,N3'-(5-amino-3-iminopyridine-2,6-(1H,3H)-diylidene)bis
{N2-[2-(4-methylpiperazin-1-yl)ethyl]pyrazolo[1,5-a]pyridine-2,3-diamine}

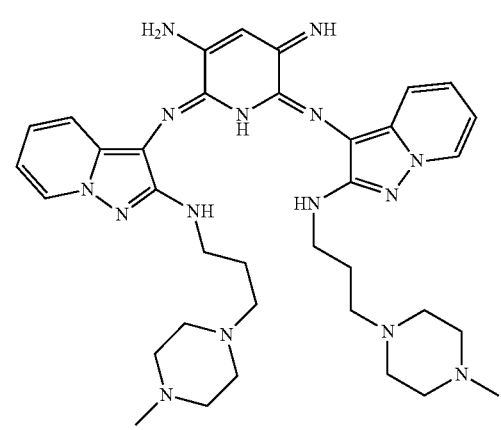

N3,N3'-(5-amino-3-iminopyridine-2,6-(1H,3H)-diylidene)bis
{N2-[3-(4-methylpiperazin-1-yl)propyl]pyrazolo[1,5-a]pyridine-2,3-diamine}

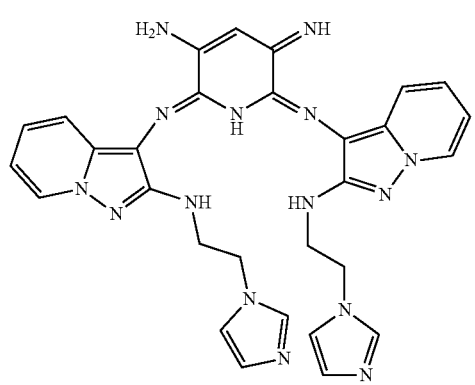

N3,N3'-(5-amino-3-iminopyridine-2,6-(1H,3H)-diylidene)bis
{N2-[2-(1H-imidazol-1-yl)ethyl]pyrazolo[1,5-a]pyridine-2,3-diamine}

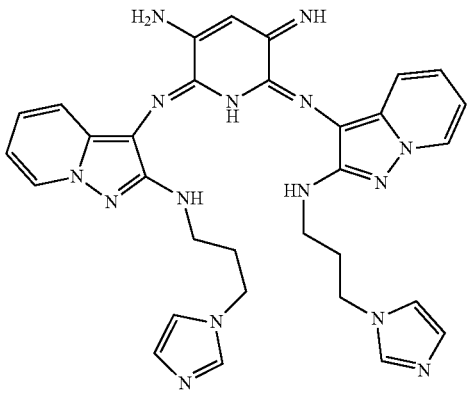

N3,N3'-(5-amino-3-iminopyridine-2,6-(1H,3H)-diylidene)bis
{N2-[3-(1H-imidazol-1-yl)propyl]pyrazolo[1,5-a]pyridine-2,3-diamine}

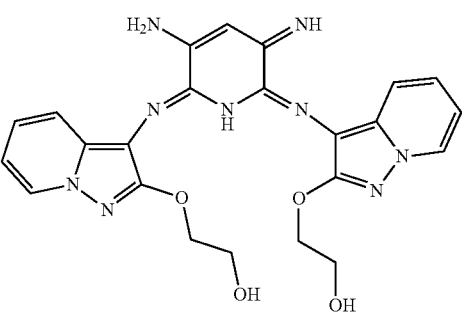

2,2'-[(5-amino-3-iminopyridine-2,6-(1H,3H)-diylidene)
bis(nitrilopyrazolo[1,5-a]pyridine-3,2-diyloxy)]diethanol

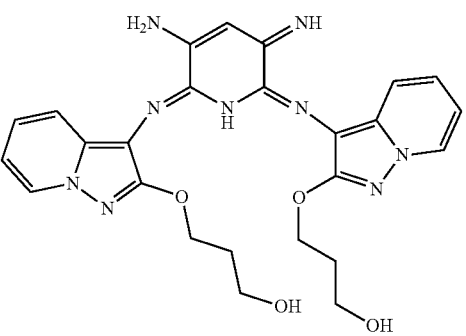

3,3'-[(5-amino-3-iminopyridine-2,6-(1H,3H)-diylidene)bis
(nitrilopyrazolo[1,5-a]pyridine-3,2-diyloxy)]dipropan-1-ol

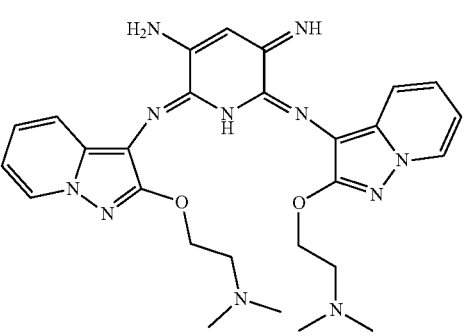

N,N'-(5-amino-3-iminopyridine-2,6-(1H,3H)-diylidene)bis
{2-[2-(dimethylamino)ethoxy]pyrazolo[1,5-a]pyridin-3-amine}

-continued

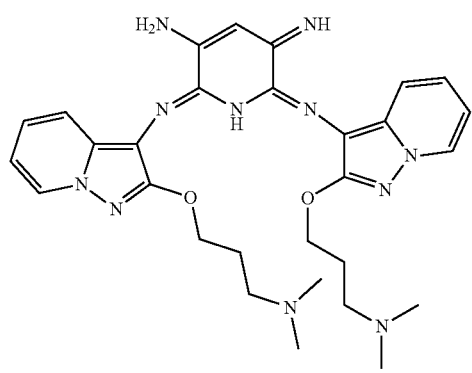

N,N′-(5-amino-3-iminopyridine-2,6-(1H,3H)-diylidene)bis
{2-[3-(dimethylamino)propoxy]pyrazolo[1,5-a]pyridin-3-amine}

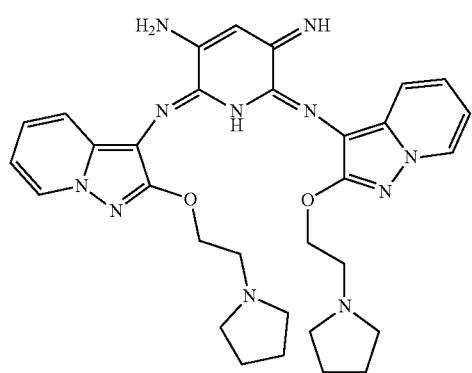

N,N′-(5-amino-3-iminopyridine-2,6-(1H,3H)-diylidene)bis
{2-[2-(pyrrolidin-1-yl)ethoxy]pyrazolo[1,5-a]pyridin-3-amine}

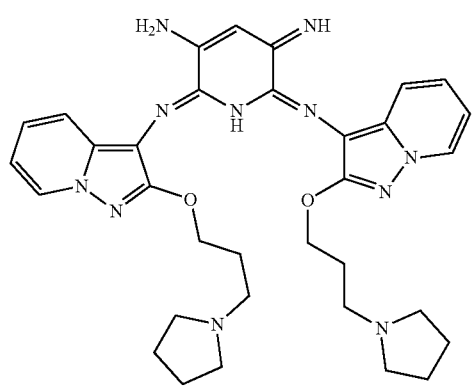

N,N′-(5-amino-3-iminopyridine-2,6-(1H,3H)-diylidene)bis
{2-[3-(pyrrolidin-1-yl)propoxy]pyrazolo[1,5-a]pyridin-3-amine}

-continued

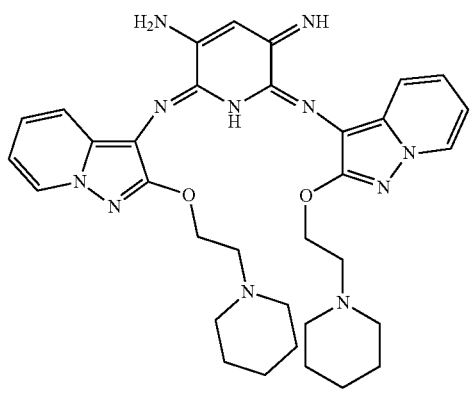

N,N′-(5-amino-3-iminopyridine-2,6-(1H,3H)-diylidene)bis
{2-[2-(piperidin-1-yl)ethoxy]pyrazolo[1,5-a]pyridin-3-amine}

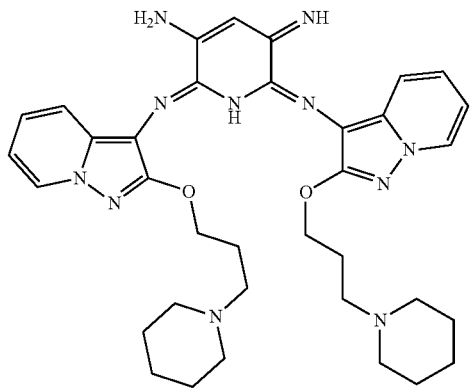

N,N′-(5-amino-3-iminopyridine-2,6-(1H,3H)-diylidene)bis
{2-[3-(piperidin-1-yl)propoxy]pyrazolo[1,5-a]pyridin-3-amine}

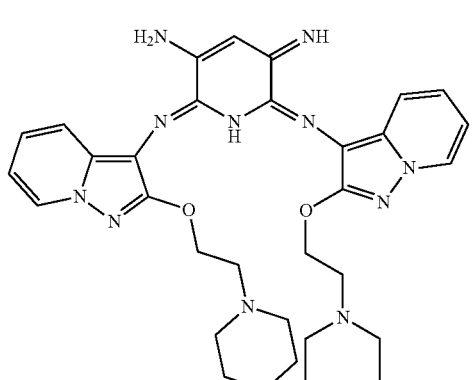

N,N′-(5-amino-3-iminopyridine-2,6-(1H,3H)-diylidene)bis
{2-[2-(morpholin-4-yl)ethoxy]pyrazolo[1,5-a]pyridin-3-amine}

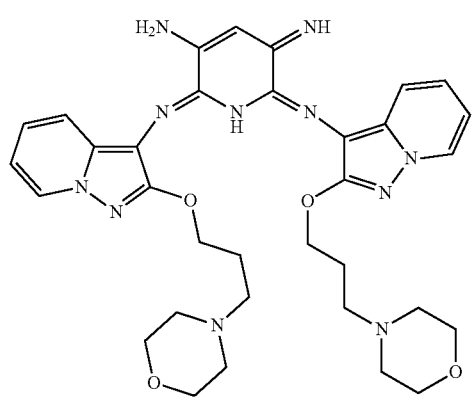

N,N'-(5-amino-3-iminopyridine-2,6-(1H,3H)-diylidene)bis
{2-[3-(morpholin-4-yl)propoxy]pyrazolo[1,5-a]pyridin-3-
amine}

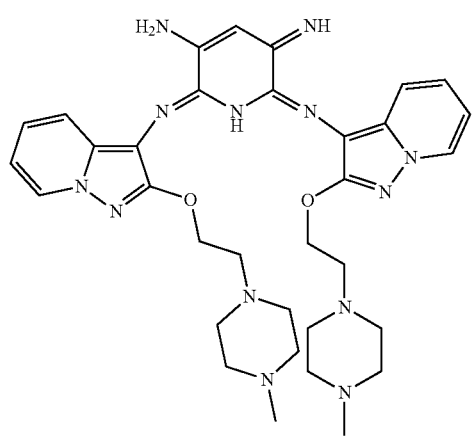

N,N'-(5-amino-3-iminopyridine-2,6-(1H,3H)-diylidene)bis
{2-[2-(4-methylpiperazin-1-yl)ethoxy]pyrazolo[1,5-a]
pyridin-3-amine}

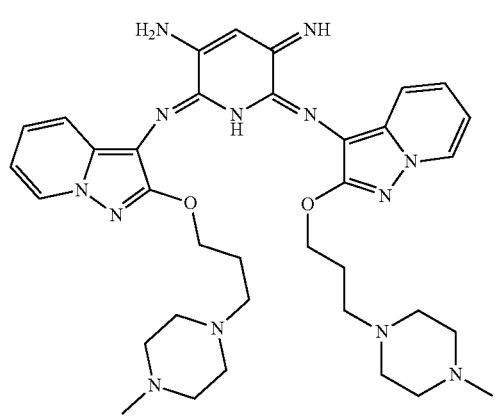

N,N'-(5-amino-3-iminopyridine-2,6-(1H,3H)-diylidene)bis
{2-[3-(4-methylpiperazin-1-yl)propoxy]pyrazolo[1,5-a]
pyridin-3-amine}

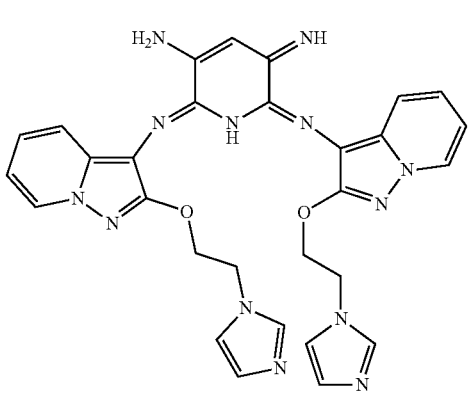

N,N'-(5-amino-3-iminopyridine-2,6-(1H,3H)-diylidene)bis
{2-[2-(1H-imidazol-1-yl)ethoxy]pyrazolo[1,5-a]pyridin-3-
amine}

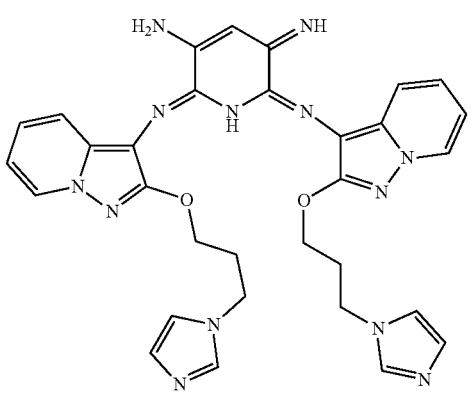

N,N'-(5-amino-3-iminopyridine-2,6-(1H,3H)-diylidene)bis
{2-[3-(1H-imidazol-1-yl)propoxy]pyrazolo[1,5-a]pyridin-3-
amine}

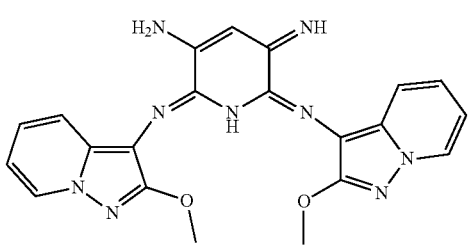

N,N'-(5-amino-3-iminopyridine-2,6-(1H,3H)-diylidene)bis
(2-methoxypyrazolo[1,5-a]pyridin-3-amine)

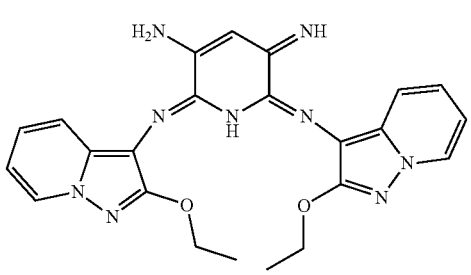

N,N'-(5-amino-3-iminopyridine-2,6-(1H,3H)-diylidene)bis
(2-ethoxypyrazolo[1,5-a]pyridin-3-amine)

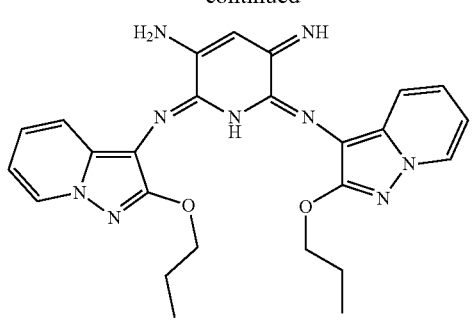

N,N'-(5-amino-3-iminopyridine-2,6-(1H,3H)-diylidene)bis(2-propoxypyrazolo[1,5-a]pyridin-3-amine)

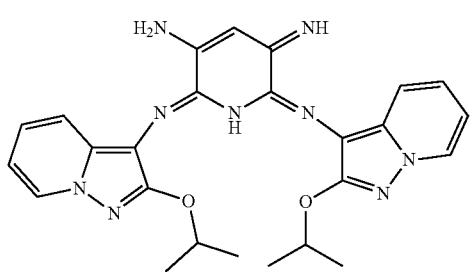

N,N'-(5-amino-3-iminopyridine-2,6-(1H,3H)-diylidene)bis[2-(propan-2-yloxy)pyrazolo[1,5-a]pyridin-3-amine]

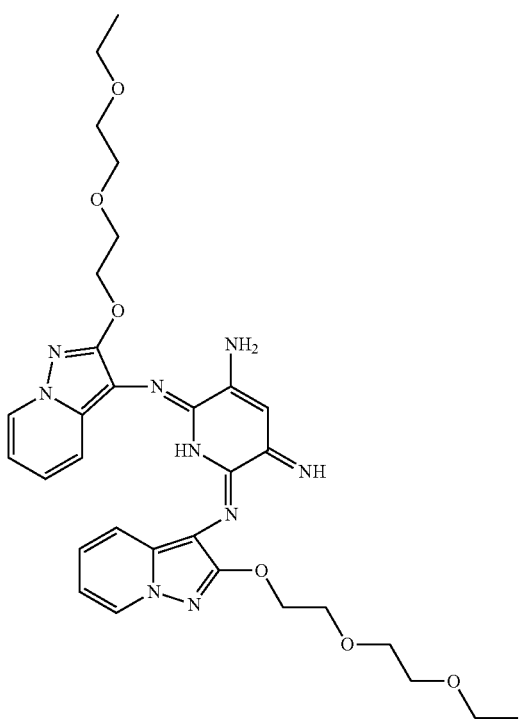

N,N'-(5-amino-3-iminopyridine-2,6-(1H,3H)-diylidene)bis{2-[2-(2-ethoxyethoxy)ethoxy]-6,7-dimethylpyrazolo[1,5-a]pyridin-3-amine}

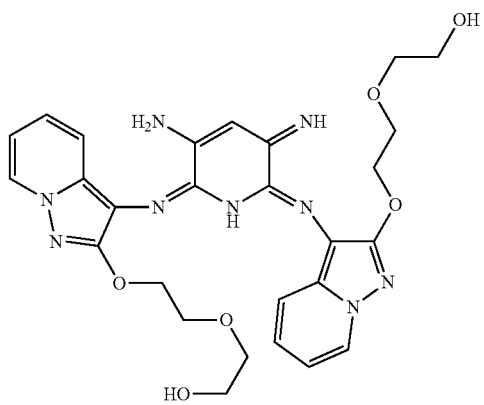

2-{2-[(3-{[3-amino-6-({2-[2-(2-hydroxyethoxy)ethoxy]pyrazolo[1,5-a]pyridin-3-yl}amino-5-imino-5,6-dihydropyridin-2(1H)-ylidene]amino}pyrazolo[1,5-a]pyridin-2-yl)oxy]ethoxy}ethanol

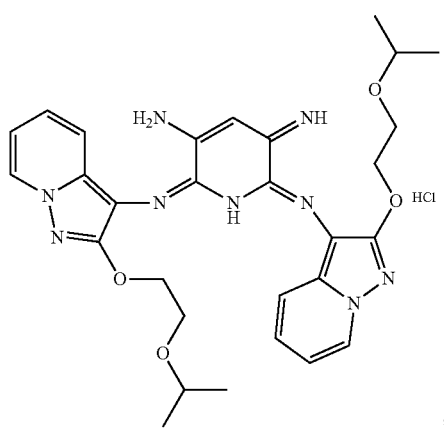

N,N'-(5-amino-3-iminopyridine-2,6-(1H,3H)-diylidene)bis{2-[2-(propan-2-yloxy)ethoxy]pyrazolo[1,5-a]pyridin-3-amine}

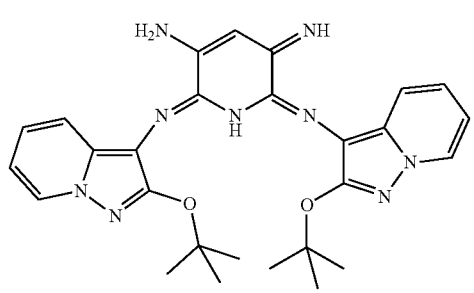

N,N'-(5-amino-3-iminopyridine-2,6-(1H,3H)-diylidene)bis(2-tert-butoxypyrazolo[1,5-a]pyridin-3-amine)

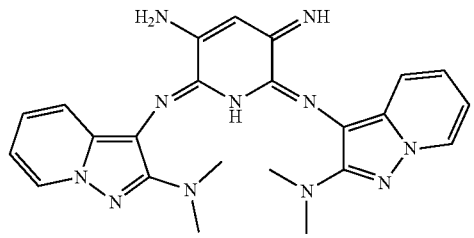

N3,N3'-(5-amino-3-iminopyridine-2,6-(1H,3H)-diylidene)bis(N2,N2-dimethylpyrazolo[1,5-a]pyridine-2,3-diamine)

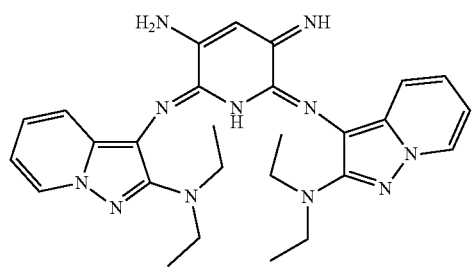

N3,N3′-(5-amino-3-iminopyridine-2,6-(1H,3H)-diylidene)bis
(N2,N2-diethylpyrazolo[1,5-a]pyridine-2,3-diamine)

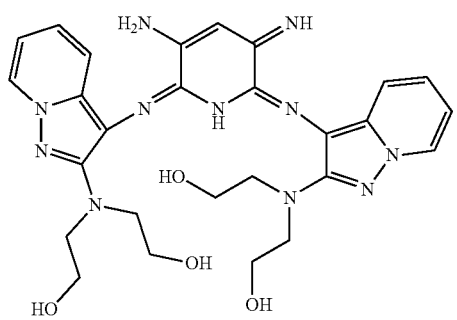

2,2′,2″,2‴-[(5-amino-3-iminopyridine-2,6-(1H,3H)-diylidene)
bis(nitrilopyrazolo[1,5-a]pyridine-3,2-diylnitrilo)]tetraethanol

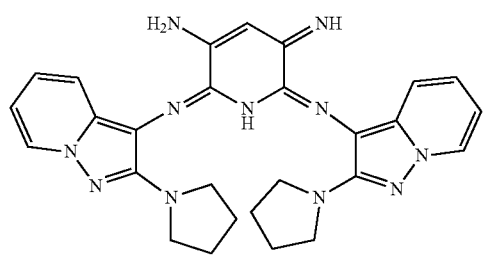

N,N′-(5-amino-3-iminopyridine-2,6-(1H,3H)-diylidene)bis
[2-(pyrrolidin-1-yl)pyrazolo[1,5-a]pyridin-3-amine]

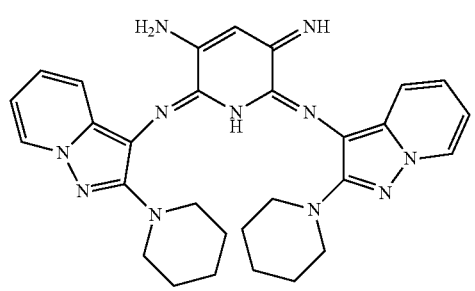

N,N′-(5-amino-3-iminopyridine-2,6-(1H,3H)-diylidene)bis
[2-(piperidin-1-yl)pyrazolo[1,5-a]pyridin-3-amine]

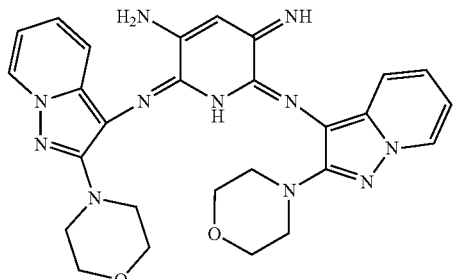

N,N′-(5-amino-3-iminopyridine-2,6-(1H,3H)-diylidene)
bis[2-(morpholin-4-yl)pyrazolo[1,5-a]pyridin-3-amine]

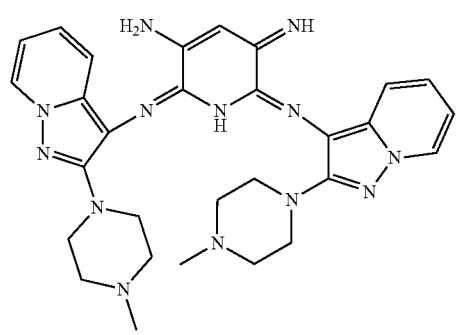

N,N′-(5-amino-3-iminopyridine-2,6-(1H,3H)-diylidene)bis
[2-(4-methylpiperazin-1-yl)pyrazolo[1,5-a]pyridin-3-amine]

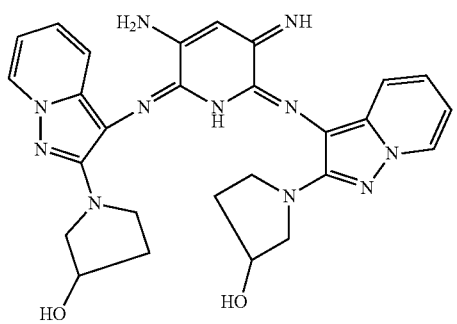

1,1′-[(5-amino-3-iminopyridine-2,6-(1H,3H)-diylidene)bis
(nitrilopyrazolo[1,5-a]pyridine-3,2-diyl)]dipyrrolidin-3-ol

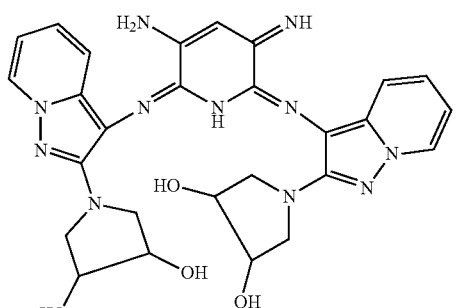

1,1′-[(5-amino-3-iminopyridine-2,6-(1H,3H)-diylidene)bis
(nitrilopyrazolo[1,5-a]pyridine-3,2-diyl)]dipyrrolidine-3,4-
diol -continued

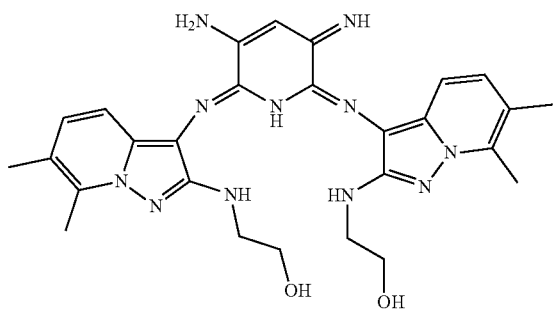

2,2'-{(5-amino-3-iminopyridine-2,6-(1H,3H)-diylidene)bis[nitrilo(6,7-dimethylpyrazolo[1,5-a]pyridine-3,2-diyl)imino]}diethanol

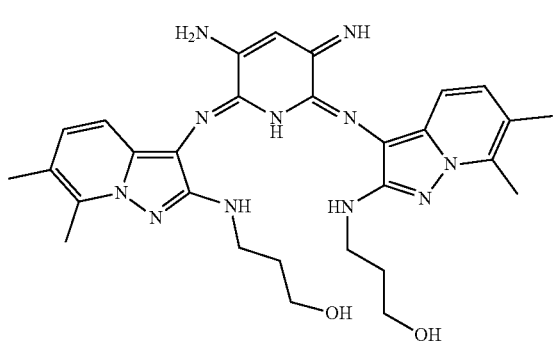

3,3'-{(5-amino-3-iminopyridine-2,6-(1H,3H)-diylidene)bis[nitrilo(6,7-dimethylpyrazolo[1,5-a]pyridine-3,2-diyl)imino]}dipropan-1-ol

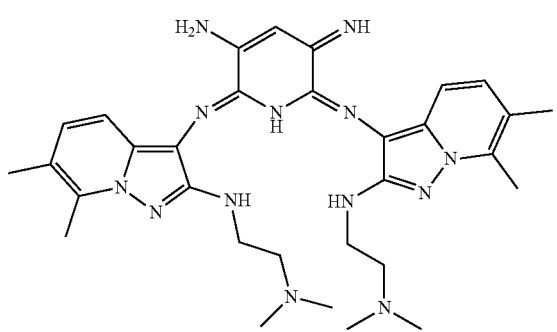

N3,N3'-(5-amino-3-iminopyridine-2,6-(1H,3H)-diylidene)bis{N2-[2-(diamethylamino)ethyl]-6,7-dimethylpyrazolo[1,5-a]pyridine-3,2-diamine}

-continued

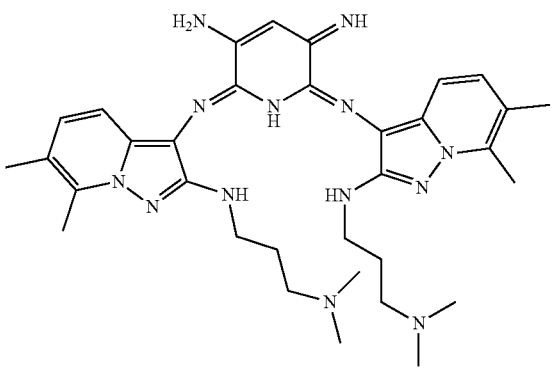

N3,N3'-(5-amino-3-iminopyridine-2,6-(1H,3H)-diylidene)bis{N2-[3-(diamethylamino)propyl]-6,7-dimethylpyrazolo[1,5-a]pyridine-2,3-diamine}

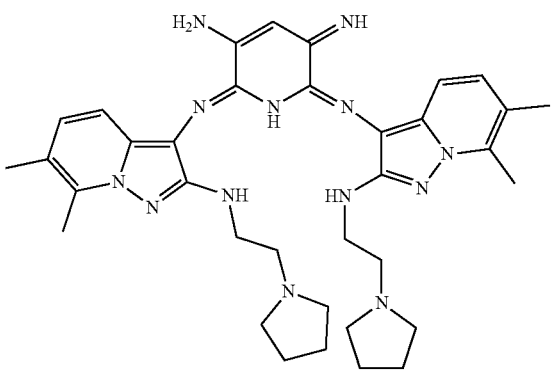

N3,N3'-(5-amino-3-iminopyridine-2,6-(1H,3H)-diylidene)bis{6,7-dimethyl-N2-[2-(pyrrolidin-1-yl)ethyl]pyrazolo[1,5-a]pyridine-2,3-diamine}

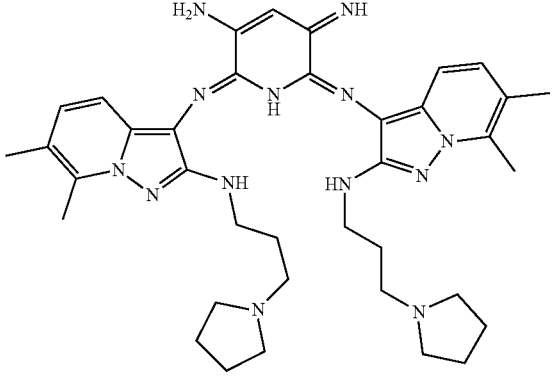

N3,N3'-(5-amino-3-iminopyridine-2,6-(1H,3H)-diylidene)bis{6,7-dimethyl-N2-[3-(pyrrolidin-1-yl)propyl]pyrazolo[1,5-a]pyridine-2,3-diamine}

53

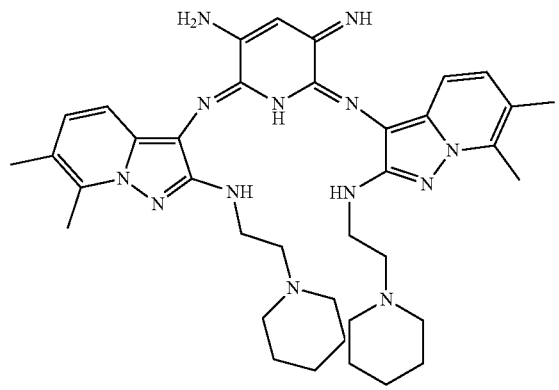

N3,N3'-(5-amino-3-iminopyridine-2,6-(1H,3H)-diylidene)bis{6,7-dimethyl-N2-[2-(piperidin-1-yl)ethyl]pyrazolo[1,5-a]pyridine-2,3-diamine}

54

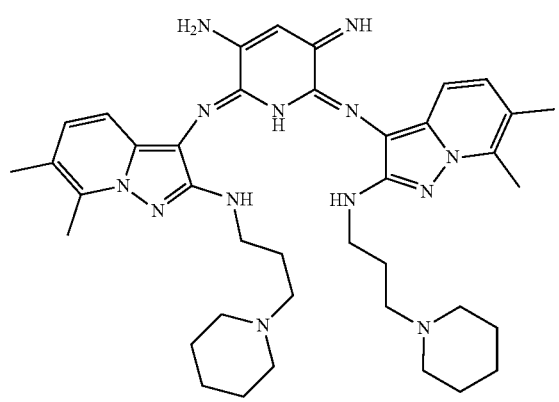

N3,N3'-(5-amino-3-iminopyridine-2,6-(1H,3H)-diylidene)bis{6,7-dimethyl-N2-[3-(piperidin-1-yl)propyl]pyrazolo[1,5-a]pyridine-2,3-diamine}

55

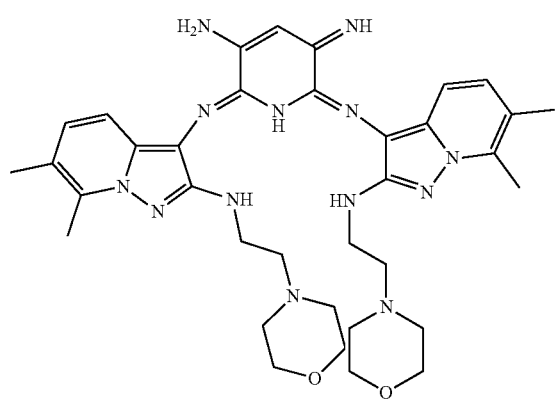

N3,N3'-(5-amino-3-iminopyridine-2,6-(1H,3H)-diylidene)bis{6,7-dimethyl-N2-[2-(morpholin-4-yl)ethyl]pyrazolo[1,5-a]pyridine-2,3-diamine}

56

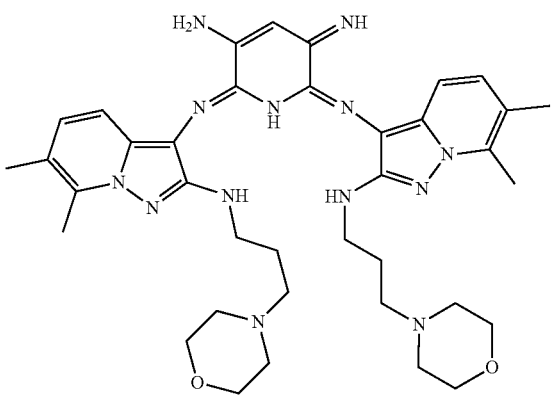

N3,N3'-(5-amino-3-iminopyridine-2,6-(1H,3H)-diylidene)bis{6,7-dimethyl-N2-[3-(morpholin-4-yl)propyl]pyrazolo[1,5-a]pyridine-2,3-diamine}

57

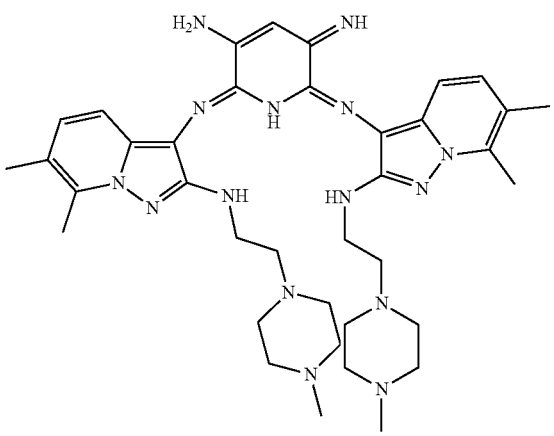

N3,N3'-(5-amino-3-iminopyridine-2,6-(1H,3H)-diylidene)bis{6,7-dimethyl-N2-[2-(4-methylpiperazin-1-yl)ethyl]pyrazolo[1,5-a]pyridine-2,3-diamine}

58

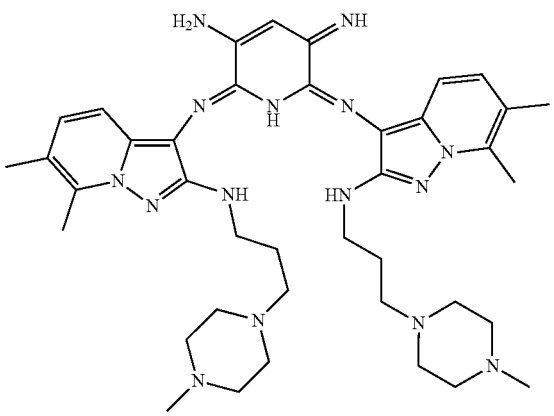

N3,N3'-(5-amino-3-iminopyridine-2,6-(1H,3H)-diylidene)bis{6,7-dimethyl-N2-[3-(4-methylpiperazin-1-yl)propyl]pyrazolo[1,5-a]pyridine-2,3-diamine}

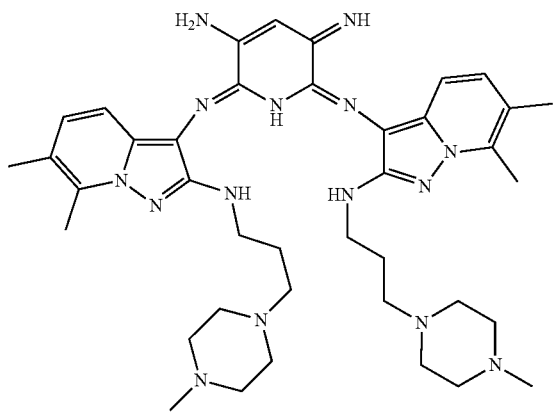

59

N3,N3'-(5-amino-3-iminopyridine-2,6-(1H,3H)-diylidene)bis{N2-[2-(1H-imidazol-1-yl)ethyl]-6,7-dimethylpyrazolo[1,5-a]pyridine-2,3-diamine}

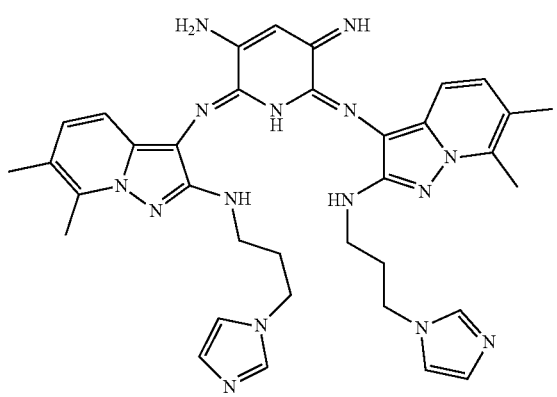

60

N3,N3'-(5-amino-3-iminopyridine-2,6-(1H,3H)-diylidene)bis{N2-[3-(1H-imidazol-1-yl)propyl]-6,7-dimethylpyrazolo[1,5-a]pyridine-2,3-diamine}

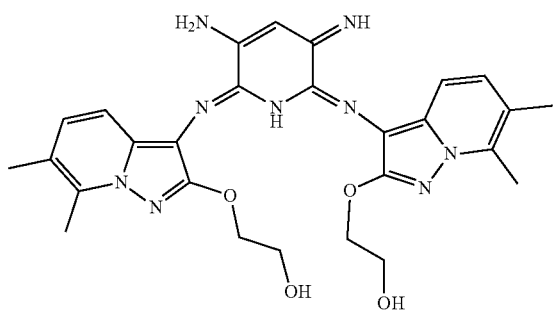

61

2,2'-{(5-amino-3-iminopyridine-2,6-(1H,3H)-diylidene)bis[nitrilo(6,7-dimethylpyrazolo[1,5-a]pyridine-3,2-diyl)oxy]}diethanol

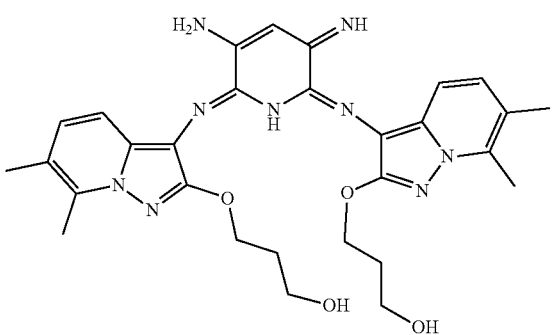

62

3,3'-{(5-amino-3-iminopyridine-2,6-(1H,3H)-diylidene)bis[nitrilo(6,7-dimethylpyrazolo[1,5-a]pyridine-3,2-diyl)oxy]}dipropan-1-ol

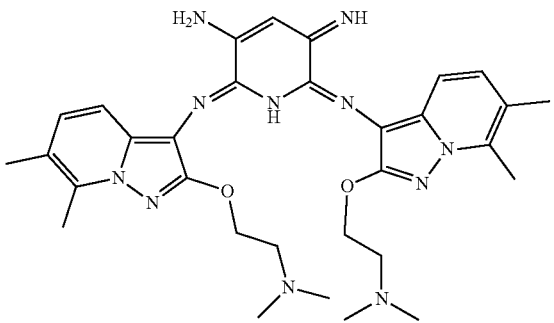

63

N,N'-(5-amino-3-iminopyridine-2,6-(1H,3H)-diylidene)bis{2-[2-(dimethylamino)ethoxy]-6,7-dimethylpyrazolo[1,5-a]pyridin-3-amine}

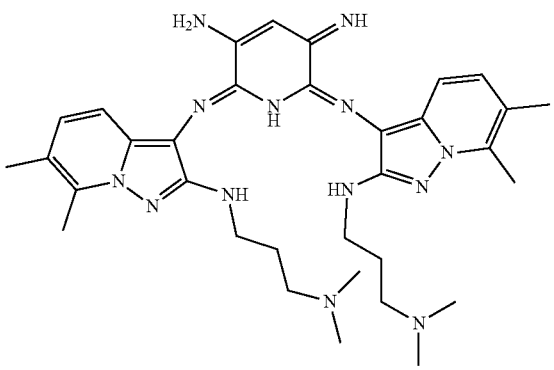

64

N3,N3'-(5-amino-3-iminopyridine-2,6-(1H,3H)-diylidene)bis{N2-[3-(dimethylamino)propyl]-6,7-dimethylpyrazolo[1,5-a]pyridine-2,3-diamine}

65

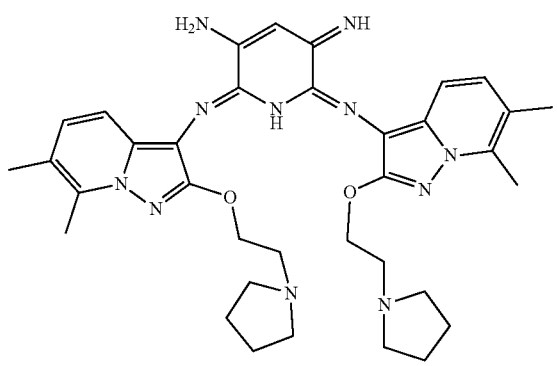

N3,N3'-(5-amino-3-iminopyridine-2,6-(1H,3H)-diylidene)bis{6,7-dimethyl-N2-[2-(pyrrolidin-1-yl)ethyl]pyrazolo[1,5-a]pyridine-2,3-diamine}

66

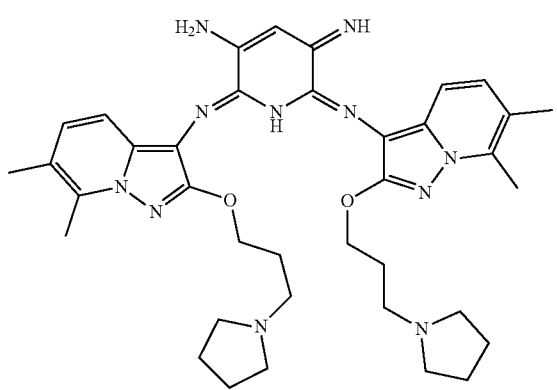

N,N'-(5-amino-3-iminopyridine-2,6-(1H,3H)-diylidene)bis{6,7-dimethyl-2-[3-(pyrrolidin-1-yl)propoxy]pyrazolo[1,5-a]pyridin-3-amine}

67

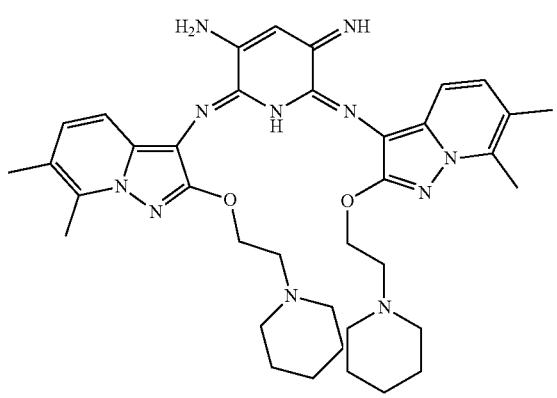

N,N'-(5-amino-3-iminopyridine-2,6-(1H,3H)-diylidene)bis{6,7-dimethyl-2-[2-(-piperidin-1-yl)ethoxy]pyrazolo[1,5-a]pyridin-3-amine}

68

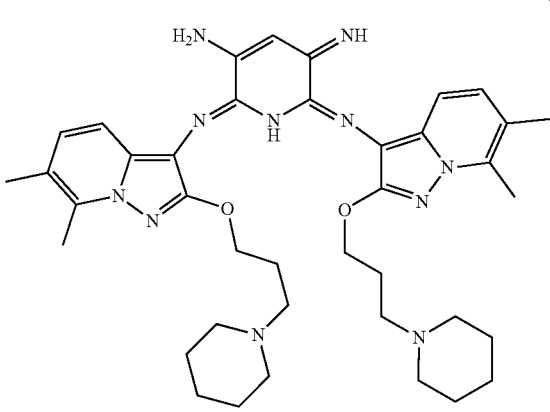

N,N'-(5-amino-3-iminopyridine-2,6-(1H,3H)-diylidene)bis{6,7-dimethyl-2-[3-(piperidin-1-yl)propoxy]pyrazolo[1,5-a]pyridin-3-amine}

69

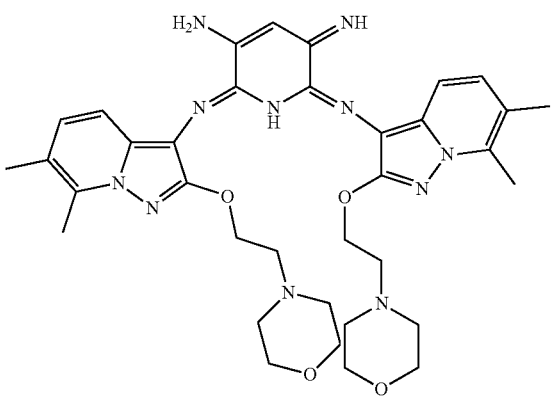

N,N'-(5-amino-3-iminopyridine-2,6-(1H,3H)-diylidene)bis{6,7-dimethyl-2-[2-(morpholin-4-yl)ethoxy]pyrazolo[1,5-a]pyridin-3-amine}

70

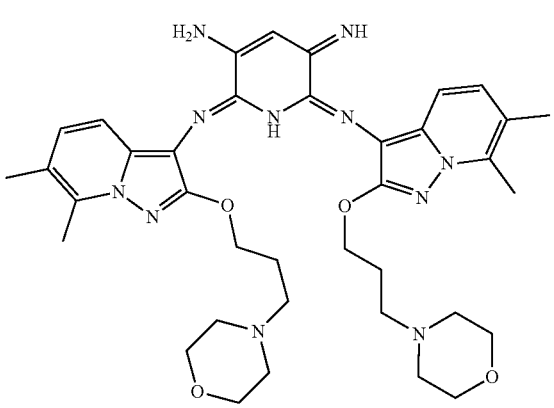

N,N'-(5-amino-3-iminopyridine-2,6-(1H,3H)-diylidene)bis{6,7-dimethyl-2-[3-(morpholin-4-yl)propoxy]pyrazolo[1,5-a]pyridin-3-amine}

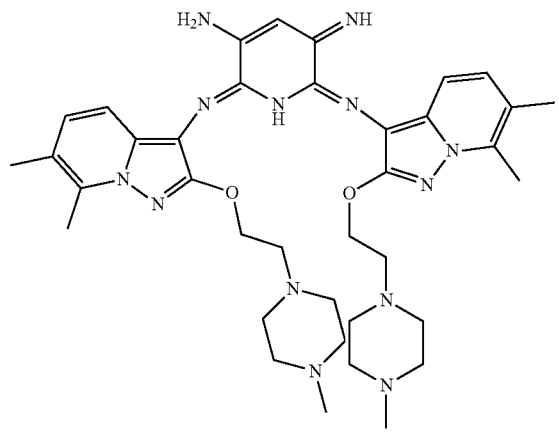

N,N'-(5-amino-3-iminopyridine-2,6-(1H,3H)-diylidene)bis{6,7-dimethyl-2-[2-(4-methylpiperazin-1-yl)ethoxy]pyrazolo[1,5-a]pyridin-3-amine}

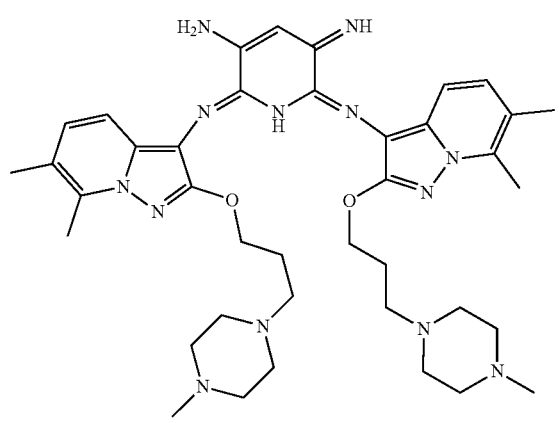

N,N'-(5-amino-3-iminopyridine-2,6-(1H,3H)-diylidene)bis{6,7-dimethyl-2-[3-(4-methylpiperazin-1-yl)propoxy]pyrazolo[1,5-a]pyridin-3-amine}

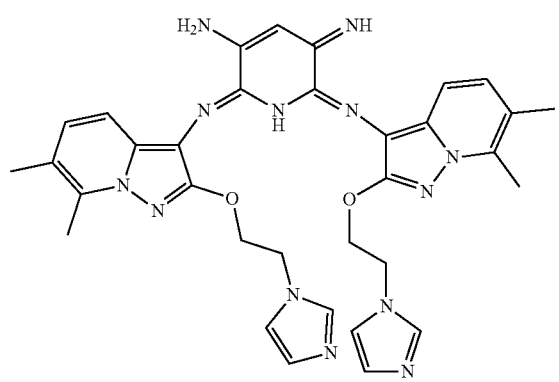

N,N'-(5-amino-3-iminopyridine-2,6-(1H,3H)-diylidene)bis{2-[2-(1H-imidazol-1-yl)ethoxy]-6,7-dimethylpyrazolo[1,5-a]pyridin-3-amine}

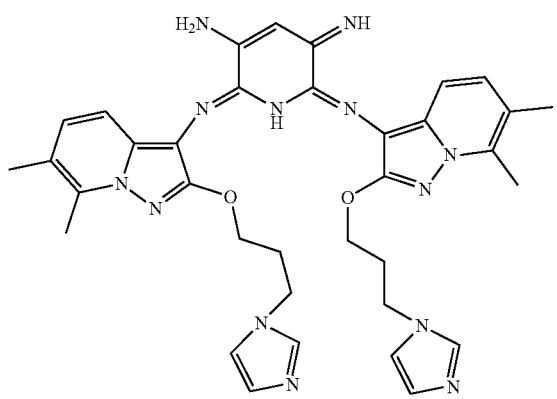

N,N'-(5-amino-3-iminopyridine-2,6-(1H,3H)-diylidene)bis{2-[3-(1H-imidazol-1-yl)propoxy]-6,7-dimethylpyrazolo[1,5-a]pyridin-3-amine}

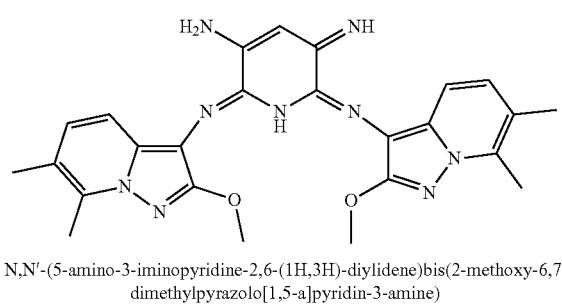

N,N'-(5-amino-3-iminopyridine-2,6-(1H,3H)-diylidene)bis(2-methoxy-6,7-dimethylpyrazolo[1,5-a]pyridin-3-amine)

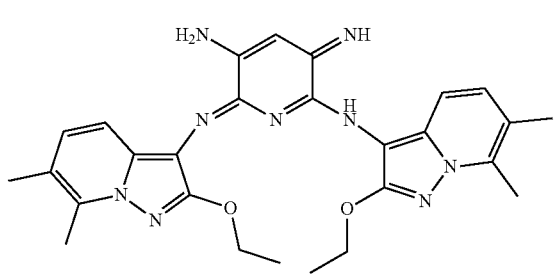

N2-(2-ethoxy-6,7-dimethylpyrazolo[1,5-a]pyridin-3-yl)-6-[(2-ethoxy-6,7-dimethylpyrazolo[1,5-a]pyridin-3-yl)imino]-3-imino-3,6-dihydropyridine-2,5-diamine

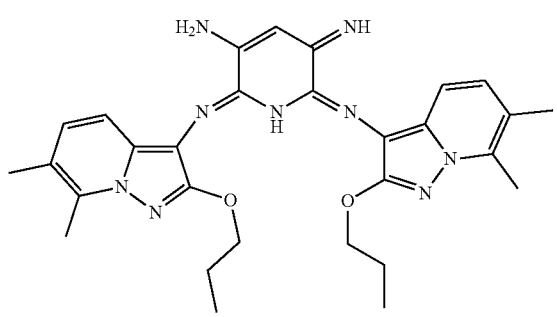

N,N'-(5-amino-3-iminopyridine-2,6-(1H,3H)-diylidene)bis(6,7-dimethyl-2-propoxypyrazolo[1,5-a]pyridin-3-amine)

78

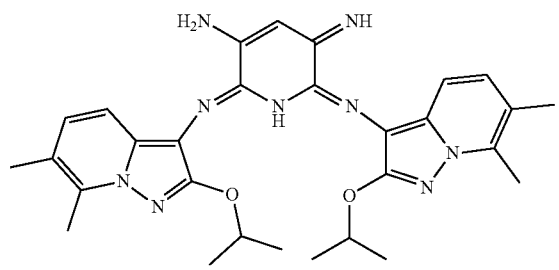

N,N'-(5-amino-3-iminopyridine-2,6-(1H,3H)-diylidene)bis(6,7-dimethyl-2-(propan-2-yloxy)pyrazolo[1,5-a]pyridin-3-amine)

79

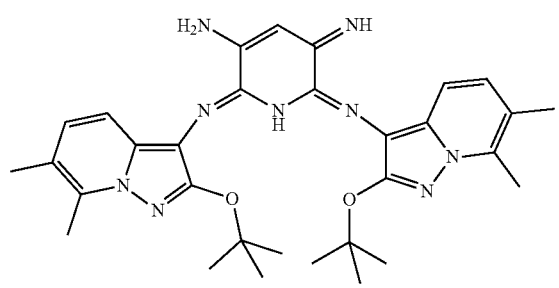

N,N'-(5-amino-3-iminopyridine-2,6-(1H,3H)-diylidene)bis(2-tert-butoxy-6,7-dimethylpyrazolo[1,5-a]pyridin-3-amine)

80

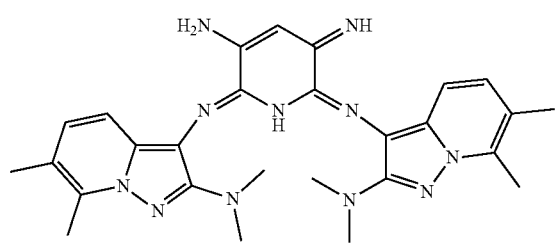

N3,N3'-(5-amino-3-iminopyridine-2,6-(1H,3H)-diylidene)bis(N2,N2,6,7-tetramethylpyrazolo[1,5-a]pyridin-2,3-damine)

81

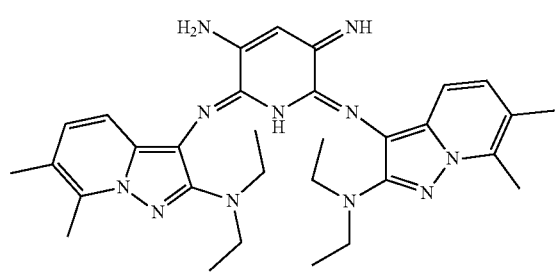

N3,N3'-(5-amino-3-iminopyridine-2,6-(1H,3H)-diylidene)bis(N2,N2-diethyl-6,7-dimethylpyrazolo[1,5-a]pyridin-2,3-damine)

82

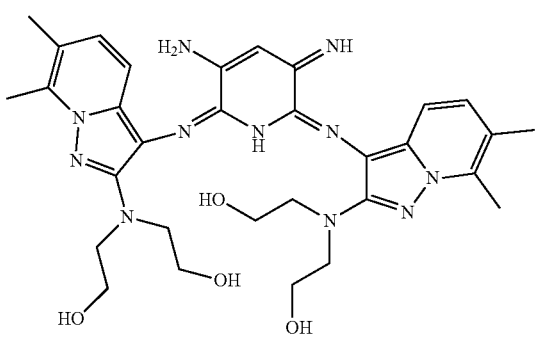

2,2',2'',2'''-{(5-amino-3-iminopyridine-2,6-(1H,3H)-diylidene)bis[nitrilo(6,7-dimethylpyrazolo[1,5-a]pyridine-3,2-diyl)nitrilo]}tetraethanol

83

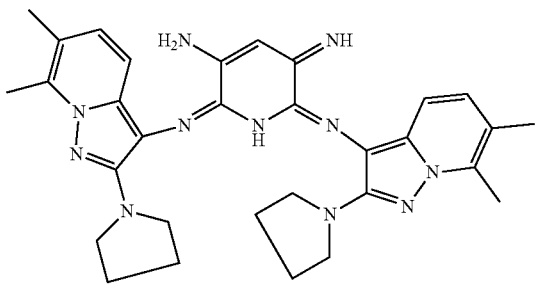

N,N'-(5-amino-3-iminopyridine-2,6-(1H,3H)-diylidene)bis[6,7-dimethyl-2-(pyrrolidin-1-yl)pyrazolo[1,5-a]pyridin-3-amine]

84

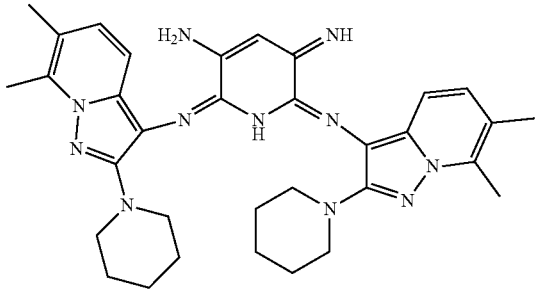

N,N'-(5-amino-3-iminopyridine-2,6-(1H,3H)-diylidene)bis[6,7-dimethyl-2-(piperidin-1-yl)pyrazolo[1,5-a]pyridin-3-amine]

85

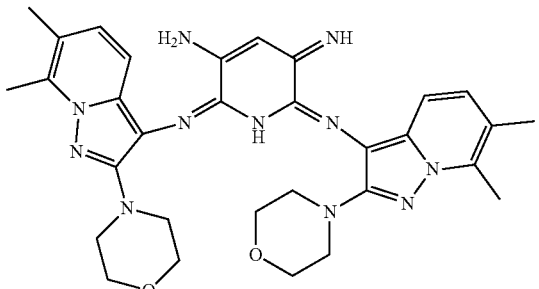

N,N'-(5-amino-3-iminopyridine-2,6-(1H,3H)-diylidene)bis[6,7-dimethyl-2-(morpholin-4-yl)pyrazolo[1,5-a]pyridin-3-amine]

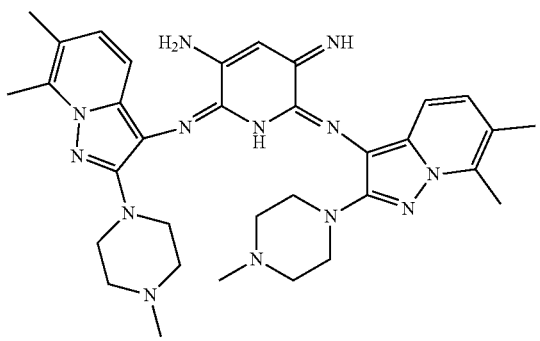

N,N'-(5-amino-3-iminopyridine-2,6-(1H,3H)-diylidene)bis[6,7-dimethyl-2-(4-methylpiperazin-1-yl)pyrazolo[1,5-a]pyridin-3-amine]

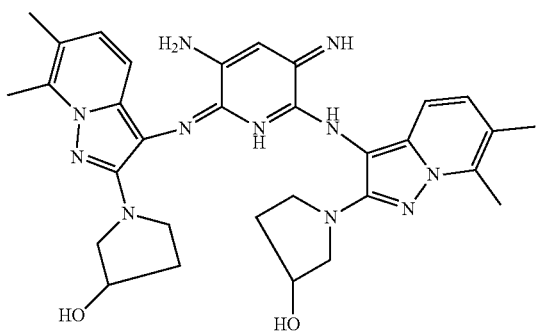

1,1'-{(5-amino-3-iminopyridine-2,6-(1H,3H)-diylidene)bis[nitrilo(6,7-dimethylpyrazolo[1,5-a]pyridine-3,2-diyl)]}dipyrrolidin-3-ol 1,1'-{(5-amino-3-iminopyridine-2,6-(1H,3H)-diylidene)bis[nitrilo(6,7-dimethylpyrazolo[1,5-a]pyridine-3,2-diyl)]}dipyrrolidin-3,4-diol and also the leuco forms thereof, the optical isomers, geometrical isomers, tautomers, solvates and addition salts thereof; more preferentially the compound of formula 1.

The compounds of formulae (I) and (II) are prepared from reagents available by conventional methods known to those skilled in the art or from commercial compounds. Mention may for example be made of the preparation process according to the following scheme:

in the case where formulae (I) and (II) are symmetrical:

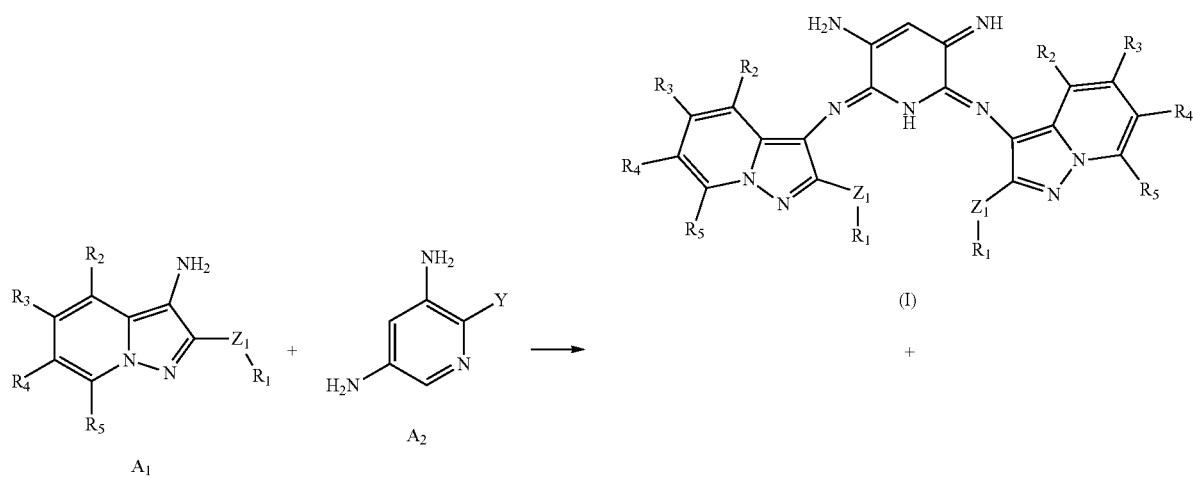

-continued

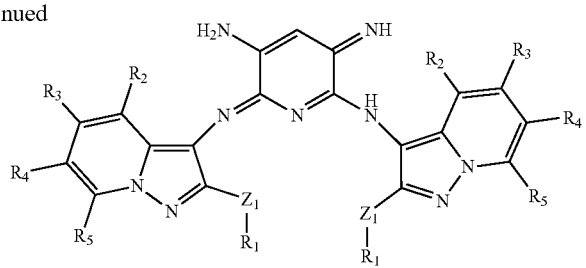

(II)

which consists:

in a first step, in reacting at least two molar equivalents of pyrazolo[1,5-a]pyridine compound $A_1$ comprising an amino group in position 3 with a pyridine compound $A_2$ which is free in position 6 and comprising in position 2 either a hydrogen atom or an electrofugal group, preferably, this reaction is performed i) in a polar protic solvent such as in water or a mixture of water/$C_1$-$C_{10}$ alcohol such as ethanol, ii) and/or in the presence of one or more mineral or organic basifying agents, as defined below, chosen in particular from sodium hydroxide, potassium hydroxide, a mineral carbonate such as potassium carbonate, or an acetate, iii) and/or in the presence of a chemical oxidizing agent such as peroxides or persulfates, iv) and/or at a temperature between ambient temperature; i.e. 25° C., and the reflux temperature of the solvent, preferably at ambient temperature; then in a second step, in maintaining the reaction medium under stirring for a time of between 5 minutes and 48 hours, more particularly between 30 minutes and 24 hours if the reaction is performed at ambient temperature; and then the reaction products (I) and (II) are optionally purified via a standard technique such as recrystallization, filtration or chromatography;

it being understood that, in formulae $A_1$, $A_2$, (I) and (II), the radicals $R_1$ to $R_5$ and $Z_1$ are as defined previously and Y represents a hydrogen atom or an electrofugal group, preferably an electrofugal group such as halogen, (poly)halo($C_1$-$C_6$ alkoxy), or (poly)(halo)($C_1$-$C_6$ alkyl)-$SO_3$—;

in the case where formulae (I) and (II) are symmetrical or dissymmetrical:

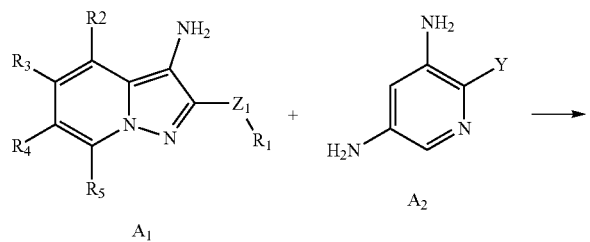

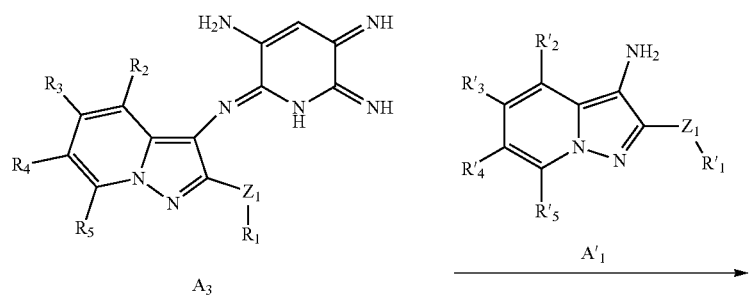

-continued

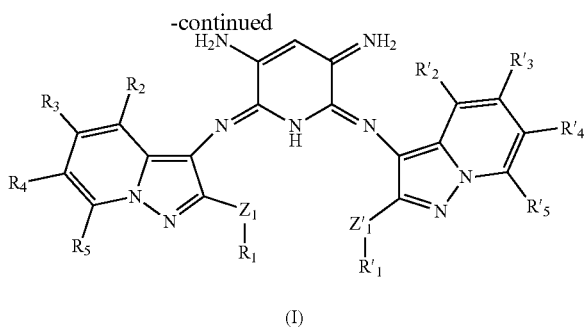

(I)

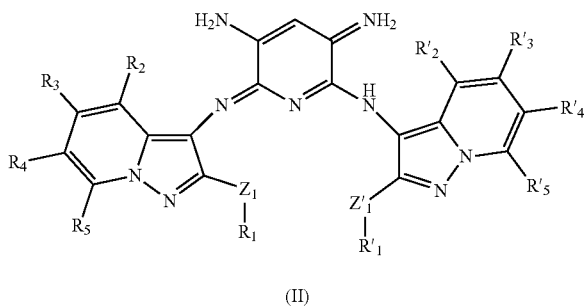

(II)

which consists:
- in a first step, in reacting one molar equivalent of pyrazolo[1,5-a]pyridine compound $A_1$ comprising an amino group in position 3 with a pyridine compound $A_2$ which is free in position 6 and comprising in position 2 either a hydrogen atom or an electrofugal group,
- preferably, this reaction is performed i) in a polar protic solvent such as in water or a mixture of water/$C_1$-$C_{10}$ alcohol such as ethanol, ii) and/or in the presence of one or more mineral or organic basifying agents, as defined below, chosen in particular from sodium hydroxide, potassium hydroxide, a mineral carbonate such as potassium carbonate, or an acetate, iii) and/or in the presence of a chemical oxidizing agent such as peroxides or persulfates, iv) and/or at a temperature between ambient temperature, i.e. 25° C., and the reflux temperature of the solvent, preferably at ambient temperature; then
- in a second step, in maintaining the reaction medium under stirring for a time of between 5 minutes and 48 hours, more particularly between 30 minutes and 24 hours if the reaction is performed at ambient temperature; and then
- the reaction product $A_3$ is optionally purified via a standard technique such as recrystallization, filtration or chromatography;
- according to a variant, compound $A_3$ once purified reacts with a molar equivalent of pyrazolo[1,5-a]pyridine compound $A'_1$ comprising an amino group in position 3, under the same conditions as steps a) and b), to give the products (I) and (II), which are optionally purified via a standard technique such as recrystallization, filtration or chromatography;
- according to another variant, compound $A_3$ is not purified, and reacts with a molar equivalent of pyrazolo[1,5-a]pyridine compound $A'_1$ comprising an amino group in position 3, under the same conditions as steps a) and b), to give the products (I) and (II), which are optionally purified via a standard technique such as recrystallization, filtration or chromatography;

it being understood that, in formulae $A_1$, $A_2$, $A_3$, (I) and (II), the radicals $R_1$ to $R_5$, $Z_1$, $R'_1$ to $R'_5$, Y and $Z'_1$ are as defined previously.

More particularly, the compounds of formula (I) and/or (II) may be obtained according to the procedure described below.

In a reactor, compound $A_1$ is dissolved in water and/or ethanol at ambient temperature. Compound $A_2$ is then added, followed by a base such as ammonia, sodium hydroxide, potassium hydroxide, a mineral carbonate such as potassium carbonate, or a sodium or potassium or ammonium acetate in the presence of an oxidizing agent. The oxidizing agent may be air, aqueous hydrogen peroxide solution or any other chemical oxidizing agent. The reaction medium becomes colored as soon as the last two reagents are added. The reaction medium thus obtained is stirred for a time of from 30 minutes to 6 days. The product formed is filtered off and then washed with water and then optionally with isopropyl ether. The compound recovered in powder form is dried at 20° C. under vacuum to constant weight. In the case where there is no precipitation, the compound resulting from this reaction is recovered by evaporating off the solvent and optionally purified on a column of silica.

The characterization is performed by NMR spectroscopy and/or mass spectrometry.

According to one particular embodiment of the invention, the compound(s) of formula (I), (II), (I') or (II') as defined previously represent from 0.01% to 15%, more particularly from 0.05% to 10% by weight, preferentially from 0.1% to 5%, relative to the total weight of the composition (1).

The composition (1) of the invention is anhydrous.

The term "anhydrous" is in particular intended to mean that water is not deliberately added to the composition (1)

but may be present in trace amount in the various compounds used in the composition.

Thus, the anhydrous composition according to the invention does not contain water or, if it does contain water, its amount is very low, i.e. less than 5%, better still less than 3%, preferably less than 2%, more preferentially less than 1% by weight relative to the total weight of the composition (1).

According to one preferred embodiment of the invention, the composition (1) comprises one or more hydrotropic solvent(s).

The term "hydrotropic solvent" is intended to mean a liquid organic compound having a Hansen solubility parameter δH greater than 0 and less than 16 MPa$^{1/2}$. The term "hydrotropic compound" is intended to mean more specifically a compound capable of increasing the solubility of hydrophobic compounds in aqueous phases.

Said hydrotropic solvent(s) is (are) liquid and more preferentially exhibit a Hansen solubility parameter δH of between 5 and 15.8 MPa$^{1/2}$, even more preferentially between 8 and 15.8 MPa$^{1/2}$ and better still between 8 and 15 MPa$^{1/2}$.

These hydrotropic solvents are liquid at a temperature of 25° C. and at atmospheric pressure (760 mmHg; i.e. 1.013×10$^5$ Pa).

The hydrotropic solvent(s) is (are) for example described in the reference publication "Hansen solubility parameters A user's handbook, Charles M. Hansen", CRC Press, 2000, pages 167 to 185, or else in the publication "Handbook of Solubility Parameters and other cohesion parameters", CRC, Press, pages 95 to 121 and pages 177 to 185.

This value of the solubility parameter δH is related to the formation of hydrogen bonds. It may be recalled that there exist three major types of interactions in organic compounds: non-polar interactions, permanent dipole-dipole interactions and interactions of hydrogen bond type, these interactions forming the subject of the parameter defining the hydrotropic solvent present in the composition (2) employed in accordance with the invention.

In particular, the publication "Handbook of Solubility Parameters and other cohesion parameters", CRC Press, pages 95 to 121 and pages 177 to 185, gives the equation δH=(Σ−zUh/V)$^{1/2}$ where zUh (in J.mol-1) describes the contributions of the functional group considered in the solubility parameters, bonded with hydrogen bonds (values in table 14, page 183), this parameter zUh also being described in the publication "The relation between surface tension and solubility parameter in liquids», Bagda, E, Farbe Lack, 84, 212, 1978; and V is the volume of the molecule.

It should be noted that the value of the solubility parameter δH is usually given for a temperature of 25° C. and at atmospheric pressure (760 mmHg, i.e. 1.013×10$^5$ Pa).

In particular, the hydrotropic solvent(s) are nonionic solvents.

Preferably, said hydrotropic solvent(s) are chosen from alcohol ethers, aliphatic esters, aliphatic ethers, aromatic ethers, alkanols bearing aryl substituents, lactones and mixtures thereof.

According to one preferred embodiment of the invention, the composition (1) comprises one or more hydrotropic solvent(s) chosen from:
- alcohol ethers, in particular $C_1$-$C_4$ ethers of $C_5$-$C_{30}$ alcohols, which are preferably saturated, linear or branched, optionally interrupted with one or more non-adjacent ether functions;
- aliphatic esters of $C_1$-$C_4$ carboxylic acids and of $C_3$-$C_{10}$ monoalcohols or polyhydroxylated alcohols, interrupted with one or more non-adjacent ether functions;
- aromatic ethers, in particular of $C_6$-$C_{10}$, of a $C_1$-$C_6$ alkyl optionally bearing a hydroxyl group;
- ($C_6$-$C_{10}$)aryl($C_1$-$C_6$)alkyl ethers, of a $C_1$-$C_6$ alkyl optionally bearing a hydroxyl group;
- alkanols bearing an aryl substituent, preferably for which the aryl part is $C_6$-$C_{10}$, advantageously $C_6$, and the alkyl part of the alkanol is $C_1$-$C_4$, this alkyl part possibly ending or being interrupted with a heteroatom, advantageously oxygen or a hydroxyl group, preferably such as benzyl alcohol;
- lactones preferably of formula (iii), and also mixtures thereof, with:

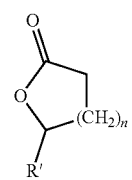

(iii)

in which formula (iii) R' represents a hydrogen, a linear or branched $C_1$-$C_8$ alkyl or a linear or branched $C_1$-$C_4$ hydroxyalkyl and n has the value 1, 2 or 3, and preferably R' represents a hydrogen, a linear or branched $C_1$-$C_6$ alkyl or a linear or branched $C_1$-$C_2$ hydroxyalkyl.

Mention may be made, as particularly advantageous examples of lactones, of γ-butyrolactone.

Mention may also be made of certain liquid alkanols, such as, for example, 1-pentanol.

Even more preferentially, said hydrotropic solvent(s) according to the invention are chosen from dipropylene glycol monomethyl ether acetate, dipropylene glycol methyl ether, dipropylene glycol mono(n-butyl) ether (the INCI name of which is PPG-2 Butyl Ether), tripropylene glycol methyl ether, propylene glycol n-butyl ether, propylene glycol n-propyl ether, propylene glycol monomethyl ether, diethylene glycol monomethyl ether and monoethyl ether, 3-phenyl-1-propanol, 2-phenyl-1-propanol, benzyl alcohol, benzyloxyethanol, phenoxyethanol, and mixtures of these compounds.

The hydrotropic solvent(s) is (are) preferably chosen from propylene glycol derivatives and aromatic alcohols, and mixtures thereof; even more preferentially chosen from alkanols bearing aryl substituents and even more preferentially benzyl alcohol and phenoxyethanol.

Preferably, the composition (1) according to the invention comprises one or more hydrotropic solvents, preferentially chosen from alkanols bearing aryl substituents and even more preferentially benzyl alcohol and phenoxyethanol.

Preferably, the hydrotropic solvent(s) represent(s) a total content ranging from 0.1% to 50% by weight, preferably from 1% to 40% by weight, better still from 5% to 30% by weight relative to the total weight of the composition (1).

According to one particular embodiment of the invention, the composition (1) also comprises an organic solvent other than the hydrotropic solvent(s) as defined previously. Mention may in particular be made of $C_1$-$C_4$ lower alkanols such as ethanol and isopropanol; polyols and polyol ethers.

Preferably, composition (1) according to the invention comprises at least one $C_1$-$C_4$ lower alkanol, such as ethanol or isopropanol. Preferably, the composition (1) according to the invention comprises ethanol.

The organic solvents other than the hydrotropic solvents are present in a total content preferably of between 1% and 95% by weight approximately, relative to the total weight of the composition (1), and even more preferentially between 5% and 80% by weight relative to the total weight of the composition (1).

The composition (1) may also comprise one or more ii) surfactants or iii) polymers as defined below.

When the composition (1) comprises one or more ii) surfactants, it (they) is (are) present particularly in an amount of between 0.01% and 60% by weight relative to the total weight of the composition (1), preferably between 0.5% and 30% by weight and even more preferentially between 1% and 20% by weight of the composition (1).

When the composition (1) comprises one or more polymers, it (they) is (are) present in a content ranging from 0.01% 10% by weight and preferably from 0.1% to 5% by weight, more preferentially between 0.5% and 3% by weight, relative to the total weight of the composition (1).

The dyeing process of the invention also uses an aqueous composition (2).

According to one particular embodiment of the invention, the composition (2) comprises at least 5% by weight of water relative to the total weight of the composition (2), more particularly at least 15% by weight, preferably at least 30% by weight, more preferentially at least 50% by weight, even better still at least 70% by weight relative to the total weight of the composition (2).

According to one preferred embodiment of the invention, the composition (2) comprises i) one or more hydrotropic solvents as defined previously, preferentially chosen from alkanols bearing aryl substituents and even more preferentially benzyl alcohol and phenoxyethanol.

In this embodiment, the hydrotropic solvent(s) is (are) present in a total content ranging from 0.01% to 50% by weight, preferably from 0.1% to 30% by weight, better still from 0.5% to 20% by weight, relative to the total weight of the composition (2).

More particularly, if the composition (1) comprises a hydrotropic solvent, the composition (2) comprises a hydrotropic solvent which is preferably different than that contained in the composition (1). More preferentially, the composition (1) comprises one or more organic solvents different than the hydrotropic solvents and the composition (2) comprises one or more hydrotropic solvents chosen from alkanols bearing aryl substituents such as benzyl alcohol and phenoxyethanol.

Preferably, the composition (2) comprises one or more hydrotropic solvents as defined previously and more preferentially phenoxyethanol.

According to one particular embodiment of the invention, the composition (2) also comprises ii) one or more anionic, cationic, nonionic, amphoteric or zwitterionic surfactants or mixtures thereof.

According to a first particular embodiment, the composition (2) of the invention contains at least one nonionic surfactant. Among the nonionic surfactants according to the invention, mention may be made, alone or as mixtures, of fatty alcohols, α-diols and alkylphenols, these three types of compound being polyethoxylated, polypropoxylated and/or polyglycerolated and containing a fatty chain comprising, for example, 8 to 22 carbon atoms, the number of ethylene oxide or propylene oxide groups possibly ranging in particular from 2 to 50 and the number of glycerol groups possibly ranging in particular from 2 to 30. Mention may also be made of ethylene oxide and propylene oxide copolymers, condensates of ethylene oxide and of propylene oxide with fatty alcohols; polyethoxylated fatty amides preferably having from 2 to 30 ethylene oxide units, polyglycerolated fatty amides containing on average 1 to 5, and in particular 1.5 to 4, glycerol groups, oxyethylenated fatty acid esters of sorbitan containing from 2 to 30 ethylene oxide units, fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

More particularly, the nonionic surfactant is chosen from: i) (poly)ethoxylated fatty alcohols; ii) glycerolated fatty alcohols; and iii) alkylpolyglycosides (APGs).

The term "fatty chain" is intended to mean a linear or branched, saturated or unsaturated hydrocarbon-based chain comprising from 6 to 30 carbon atoms and preferably from 8 to 24 carbon atoms.

As regards the alkylpolyglycosides, these compounds are well known and may be represented more particularly by the following general formula:

$$R_1O—(R_2O)_t(G)_v \qquad (III)$$

in which formula (III):

R$_1$ represents a linear or branched alkyl and/or alkenyl radical comprising from about 8 to 24 carbon atoms, or an alkylphenyl radical of which the linear or branched alkyl radical comprises from 8 to 24 carbon atoms;

R$_2$ represents an alkylene radical comprising from about 2 to 4 carbon atoms;

G represents a sugar unit comprising from 5 to 6 carbon atoms;

t denotes an integer between 0 and 10 inclusive, preferably between 0 and 4; and v denotes an integer between 1 and 15 inclusive.

Preferred alkylpolyglycosides according to the present invention are compounds of formula (III) wherein R$_1$ more particularly denotes a linear or branched, saturated or unsaturated alkyl radical comprising from 8 to 18 carbon atoms, t denotes a value ranging from 0 to 3 and more particularly equal to 0, and G may denote glucose, fructose or galactose, preferably glucose. The degree of polymerization, i.e. the value of v in formula (III), may range from 1 to 15 and preferably from 1 to 4. The average degree of polymerization is more particularly between 1 and 2 and even more preferentially from 1.1 to 1.5.

The glycoside bonds between the sugar units are of 1-6 or 1-4 type and preferably of 1-4 type.

Compounds of formula (III) are in particular represented by the products sold by the company Cognis under the names Plantaren® (600 CS/U, 1200 and 2000) or Plantacare® (818, 1200 and 2000). It is also possible to use the products sold by the company SEPPIC under the names Triton CG 110 (or Oramix CG 110) and Triton CG 312 (or Oramix® NS 10), the products sold by the company BASF under the name Lutensol GD 70 or else those sold by the company Chem Y under the name AG10 LK.

It is also possible to use, for example, ($C_8$/$C_{16}$)alkyl-1,4-polyglucoside as an aqueous 53% solution, sold by the company Cognis under the reference Plantacare® 818 UP.

As regards the mono- or polyglycerolated surfactants, they preferably comprise on average from 1 to 30 glycerol groups, more particularly from 1 to 10 and in particular from 1.5 to 5 glycerol groups.

The monoglycerolated or polyglycerolated surfactants are preferably chosen from the compounds of the following formulae:

RO[CH$_2$CH(CH$_2$OH)O]$_m$H, RO[CH$_2$CH(OH)CH$_2$O]$_m$H or RO[CH(CH$_2$OH)CH$_2$O]$_m$H;

in which formulae:
R represents a linear or branched, saturated or unsaturated, hydrocarbon-based radical comprising from 8 to 40 carbon atoms and preferably from 10 to 30 carbon atoms; and m is a number between 1 and 30, preferably between 1 and 10, more particularly from 1.5 to 6. R may optionally comprise heteroatoms, for instance oxygen and nitrogen. In particular, R may optionally comprise one or more hydroxyl and/or ether and/or amide groups. R preferably denotes optionally mono- or polyhydroxylated $C_{10}$-$C_{20}$ alkyl and/or alkenyl radicals.

Use may be made, for example, of the polyglycerolated (3.5 mol) hydroxylauryl ether sold under the name Chimexane® NF from Chimex.

The (poly)ethoxylated fatty alcohols which are suitable for implementing the invention are selected more particularly from alcohols containing from 8 to 30 carbon atoms, and preferably from 12 to 22 carbon atoms.

The (poly)ethoxylated fatty alcohols more particularly contain one or more linear or branched, saturated or unsaturated hydrocarbon-based groups, comprising 8 to 30 carbon atoms, which are optionally substituted, in particular with one or more (in particular 1 to 4) hydroxyl groups. If they are unsaturated, these compounds may comprise one to three conjugated or unconjugated carbon-carbon double bonds.

The (poly)ethoxylated fatty alcohol(s) preferably have the following formula:

$$R^a\text{---}[O\text{---}CH_2\text{---}CH_2]_n\text{---}OH$$

with
$R^a$ representing a linear or branched $C_1$-$C_{40}$ alkyl or linear or branched $C_2$-$C_{30}$ alkenyl (preferentially $C_8$-$C_{30}$ alkyl) group and
n representing an integer between 1 and 200 inclusive, preferentially between 2 and 50 and more particularly between 2 and 30 inclusive, such as 20.

The (poly)ethoxylated fatty alcohols are more particularly fatty alcohols comprising from 8 to 22 carbon atoms and oxyethylenated with 1 to 30 mol of ethylene oxide (1 to 30 EO). Among them, mention may be made more particularly of lauryl alcohol 2 EO, lauryl alcohol 3 EO, decyl alcohol 3 EO, decyl alcohol 5 EO and oleyl alcohol 20 EO.

Mixtures of these (poly)oxyethylenated fatty alcohols may also be used.

Among the nonionic surfactants, use is preferably made of $C_6$-$C_{24}$ alkyl polyglucosides and (poly)ethoxylated fatty alcohols, and $C_8$-$C_{16}$ alkyl polyglucosides are more particularly used.

When it (they) is(are) present, the total amount of non-ionic surfactants preferably ranges from 0.01% to 60% by weight relative to the total weight of the composition (2), preferably from 0.5% to 30% by weight, and more particularly from 2% to 10% by weight relative to the total weight of the composition of the invention.

According to another particular embodiment of the invention, the composition (2) comprises one or more anionic surfactants.

The term "anionic surfactant" is intended to mean a surfactant comprising, as ionic or ionizable groups, only anionic groups. These anionic groups are preferably chosen from the groups —C(O)OH, —C(O)O$^-$, —SO$_3$H, —S(O)$_2$O, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$ and =POH, =PO$^-$, the anionic parts comprising a cationic counterion such as those derived from an alkali metal, an alkaline-earth metal, an amine or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may in particular be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts, and in particular sodium or magnesium salts.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, in particular in the form of alkali metal, ammonium, amino alcohol and alkaline-earth metal salts, or a mixture of these compounds.

It is in particular preferred to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds. Even better still, it is preferred to use sodium lauryl ether sulfate, in particular those containing 2.2 mol of ethylene oxide, more preferentially ($C_{12}$-$C_{20}$)alkyl sulfates such as an alkali metal lauryl sulfate such as sodium lauryl sulfate.

According to one particular embodiment of the invention, the composition (2) comprises one or more amphoteric or zwitterionic surfactants. The amphoteric or zwitterionic surfactant(s) of the invention are non-silicone, and are in particular derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of $(C_8-C_{20})$alkyl betaines, sulfobetaines, $(C_8-C_{20})$alkylamido$(C_3-C_8)$alkyl betaines and $(C_8-C_{20})$alkylamido$(C_6-C_8)$alkyl sulfobetaines.

Among the amphoteric or zwitterionic surfactants mentioned above, use is preferably made of $(C_8-C_{20})$alkylbetaines such as cocoylbetaine, and $(C_8-C_{20})$alkylamido$(C_3-C_8)$alkylbetaines such as cocamidopropylbetaine, and mixtures thereof. More preferentially, the amphoteric or zwitterionic surfactant(s) are chosen from cocamidopropylbetaine and cocoylbetaine.

According to one particular embodiment, the composition (2) comprises one or more cationic surfactant(s), in particular optionally polyoxyalkylenated primary, secondary or tertiary fatty amine salts, or quaternary amine salts, and mixtures thereof. Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

When it (they) is (are) present, the surfactant(s) represent(s) in total particularly from 0.01% to 60% by weight relative to the total weight of the composition (2), preferably from 0.5% to 30% by weight and even more preferentially from 1% to 20% by weight of the composition (2).

According to another particular embodiment of the invention, the composition (2) comprises iii) one or more optionally associative, optionally substantive, preferably thickening, anionic, cationic, nonionic, amphoteric or zwitterionic polymers or blends thereof.

According to one particular embodiment, the composition (2) of the invention contains one or more thickening polymers. The thickening polymers according to the invention may be of natural or synthetic origin.

Thickening polymers that may be mentioned include nonassociative thickening polymers bearing sugar units.

Within the context of the present invention, the term "sugar unit" is intended to mean a unit derived from a carbohydrate of formula $C_n(H_2O)_{n-1}$, or $(CH_2O)_n$, which may be optionally modified by substitution and/or by oxidation and/or by dehydration.

Sugar units which may be part of the composition of the thickening polymers of the invention are preferably derived from the following sugars: i) glucose; ii) galactose; iii) arabinose; iv) rhamnose; v) mannose; vi) xylose; vii) fucose; viii) anhydrogalactose; ix) galacturonic acid; x) glucuronic acid; xi) mannuronic acid; xii) galactose sulfate; xiii) anhydrogalactose sulfate and xiv) fructose.

Thickening polymers of the invention that may in particular be mentioned include native gums such as:
a) tree or shrub exudates, including:
  gum arabic (branched polymer of galactose, arabinose, rhamnose and glucuronic acid);
  ghatti gum (polymer derived from arabinose, galactose, mannose, xylose and glucuronic acid);
  karaya gum (polymer derived from galacturonic acid, galactose, rhamnose and glucuronic acid);
  gum tragacanth (or tragacanth) (polymer of galacturonic acid, galactose, fucose, xylose and arabinose);
b) gums resulting from algae, including:
  agar (polymer derived from galactose and anhydrogalactose);
  alginates (polymers of mannuronic acid and of glucuronic acid);
  carrageenans and furcellerans (polymers of galactose sulfate and of anhydrogalactose sulfate);
c) gums derived from seeds or tubers, including:
  guar gum (polymer of mannose and galactose);
  locust bean gum (polymer of mannose and galactose);
  fenugreek gum (polymer of mannose and galactose);
  tamarind gum (polymer of galactose, xylose and glucose);
  konjac gum (polymer of glucose and mannose);
d) microbial gums, including:
  xanthan gum (polymer of glucose, mannose acetate, mannose/pyruvic acid and glucuronic acid);
  gellan gum (polymer of partially acylated glucose, rhamnose and glucuronic acid);
  scleroglucan gum (glucose polymer);
e) plant extracts, including:
  cellulose (glucose polymer);
  starch (glucose polymer) and
  inulin.

These polymers can be physically or chemically modified. As physical treatment, mention may in particular be made of the temperature.

As chemical treatments, mention may be made of esterification, etherification, amidation or oxidation reactions. These treatments make it possible to lead to polymers that may in particular be nonionic, anionic or amphoteric.

Preferably, these chemical or physical treatments are applied to guar gums, locust bean gums, starches and celluloses.

The nonionic guar gums that may be used according to the invention may be modified with $C_1-C_6$ (poly)hydroxyalkyl groups.

Among the $C_1-C_6$ (poly)hydroxyalkyl groups, mention may be made, for example, of hydroxymethyl, hydroxyethyl, hydroxypropyl and hydroxybutyl groups.

These guar gums are well known in the prior art and may be prepared, for example, by reacting the corresponding alkene oxides, for instance, propylene oxides, with the guar gum so as to obtain a guar gum modified with hydroxypropyl groups.

The degree of hydroxyalkylation preferably varies from 0.4 to 1.2 and corresponds to the number of alkylene oxide molecules consumed by the number of free hydroxyl functional groups present on the guar gum.

Such nonionic guar gums optionally modified with hydroxyalkyl groups are sold, for example, under the trade names Jaguar HP8, Jaguar HP60 and Jaguar HP120 by the company Rhodia Chimie.

The botanical origin of the starch molecules used in the present invention may be cereals or tubers. Thus, the starches are chosen, for example, from corn starch, rice starch, cassava starch, barley starch, potato starch, wheat starch, sorghum starch and pea starch.

The starches may be chemically or physically modified, in particular by one or more of the following reactions: pregelatinization, oxidation, crosslinking, esterification, etherification, amidation, heat treatments.

Distarch phosphates or compounds rich in distarch phosphate will preferentially be used, for instance the product sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized corn distarch phosphate).

According to the invention, amphoteric starches may also be used, these amphoteric starches comprising one or more anionic groups and one or more cationic groups. The anionic and cationic groups may be bonded to the same reactive site of the starch molecule or to different reactive sites; they are preferably bonded to the same reactive site. The anionic groups may be of carboxylic, phosphate or sulfate type, preferably carboxylic. The cationic groups may be of primary, secondary, tertiary or quaternary amine type.

The starch molecules may be derived from any plant source of starch, in particular such as corn, potato, oat, rice, tapioca, sorghum, barley or wheat. It is also possible to use the hydrolyzates of the starches mentioned above. The starch is preferably derived from potato.

The nonassociative thickening polymers of the invention may be cellulose-based polymers not comprising a $C_{10}$-$C_{30}$ fatty chain in their structure.

According to the invention, the term "cellulose-based" polymer is intended to mean any polysaccharide compound having in its structure sequences of glucose residues linked together via β-1,4 bonds; in addition to unsubstituted celluloses, the cellulose derivatives may be anionic, cationic, amphoteric or nonionic.

Thus, the cellulose-based polymers of the invention may be chosen from unsubstituted celluloses, including those in a microcrystalline form, and cellulose ethers.

Among these cellulose-based polymers, cellulose ethers, cellulose esters and cellulose ester ethers are distinguished.

Among the cellulose esters are mineral esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/mineral esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

Among the nonionic cellulose ethers without a $C_{10}$-$C_{30}$ fatty chain, i.e. which are "nonassociative", mention may be made of $(C_1$-$C_6)$alkylcelluloses, such as methylcelluloses and ethylcelluloses (for example, Ethocel standard 100 Premium from Dow Chemical); (poly)hydroxy$(C_1$-$C_6)$alkylcelluloses, such as hydroxymethylcelluloses, hydroxyethylcelluloses (for example, Natrosol 250 HHR provided by Aqualon) and hydroxypropylcelluloses (for example, Klucel EF from Aqualon); mixed (poly)hydroxy$(C_1$-$C_6)$alkyl-$(C_1$-$C_6)$alkylcelluloses, such as hydroxypropylmethylcelluloses (for example, Methocel E4M from Dow Chemical), hydroxyethylmethylcelluloses, hydroxyethylethylcelluloses (for example, Bermocoll E 481 FQ from Akzo Nobel) and hydroxybutylmethylcelluloses.

Among the anionic cellulose ethers without a fatty chain, mention may be made of (poly)carboxy$(C_1$-$C_4)$alkylcelluloses and salts thereof. By way of example, mention may be made of carboxymethylcelluloses, carboxymethylmethylcelluloses (for example Blanose 7M from the company Aqualon) and carboxymethylhydroxyethylcelluloses, and the sodium salts thereof.

Among the cationic cellulose ethers without a fatty chain, mention may be made of cationic cellulose derivatives such as cellulose copolymers or cellulose derivatives grafted with a water-soluble quaternary ammonium monomer, and described in particular in patent U.S. Pat. No. 4,131,576, such as (poly)hydroxy$(C_1$-$C_4)$alkyl celluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt. The commercial products corresponding to this definition are more particularly the products sold under the names Celquat® L 200 and Celquat® H 100 by the company National Starch.

Among the nonassociative thickening polymers not bearing sugar units that may be used, mention may be made of crosslinked acrylic acid or methacrylic acid homopolymers or copolymers, crosslinked 2-acrylamido-2-methylpropanesulfonic acid homopolymers and crosslinked acrylamide copolymers thereof, ammonium acrylate homopolymers, or copolymers of ammonium acrylate and of acrylamide, alone or mixtures thereof.

A first family of nonassociative thickening polymers that is suitable for use is represented by crosslinked acrylic acid homopolymers.

Among the homopolymers of this type, mention may be made of those crosslinked with an allyl alcohol ether of the sugar series, for instance, the products sold under the names Carbopol 980, 981, 954, 2984 and 5984 by the company Noveon or the products sold under the names Synthalen M and Synthalen K by the company 3 VSA.

The nonassociative thickening polymers may also be crosslinked (meth)acrylic acid copolymers, such as the polymer sold under the name Aqua SF1 by the company Noveon.

The nonassociative thickening polymers may be chosen from crosslinked 2-acrylamido-2-methylpropanesulfonic acid homopolymers and the crosslinked acrylamide copolymers thereof.

Among the partially or totally neutralized crosslinked copolymers of 2-acrylamido-2-methylpropanesulfonic acid and of acrylamide, mention may be made in particular of the product described in Example 1 of document EP 503 853, and reference may be made to said document as regards these polymers.

The composition may similarly comprise, as nonassociative thickening polymers, ammonium acrylate homopolymers or copolymers of ammonium acrylate and of acrylamide.

Among the ammonium acrylate homopolymers that may be mentioned is the product sold under the name Microsap PAS 5193 by the company Hoechst. Among the copolymers of ammonium acrylate and of acrylamide that may be mentioned is the product sold under the name Bozepol C Nouveau or the product PAS 5193 sold by the company Hoechst. Reference may be made in particular to documents FR 2 416 723, U.S. Pat. Nos. 2,798,053 and 2,923,692 as regards the description and preparation of such compounds.

Among the aqueous-phase thickening polymers, mention may also be made of the non-cellulose-based associative polymers that are well known to those skilled in the art and in particular of nonionic, anionic, cationic or amphoteric nature.

It is recalled that "associative polymers" are polymers that are capable, in an aqueous medium, of reversibly associating with each other or with other molecules.

Their chemical structure more particularly comprises at least one hydrophilic region and at least one hydrophobic region.

The term "hydrophobic group" is intended to mean a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferably, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, such as, for example, polybutadiene.

Among the associative polymers of anionic type that may be mentioned are:

(a) those comprising at least one hydrophilic unit and at least one fatty-chain allyl ether unit, more particularly those of which the hydrophilic unit is formed by an ethylenic unsaturated anionic monomer, more particularly by a vinylcarboxylic acid and most particularly by an acrylic acid or a methacrylic acid or mixtures thereof.

Among these anionic associative polymers, those that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether, and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), in particular those sold by the company Ciba under the names Salcare SC 80® and Salcare SC 90®, which are aqueous 30% emulsions of a crosslinked terpolymer of methacrylic acid, of ethyl acrylate and of steareth-10 allyl ether (40/50/10);

(b) those comprising i) at least one hydrophilic unit of unsaturated olefinic carboxylic acid type, and ii) at least one hydrophobic unit of the ($C_{10}$-$C_{30}$) alkyl ester of an unsaturated carboxylic acid type.

($C_{10}$-$C_{30}$) alkyl esters of unsaturated carboxylic acids that are useful in the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to patents U.S. Pat. Nos. 3,915,921 and 4,509,949.

Among anionic associative polymers of this type, use will more particularly be made of those constituted of 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or else of those constituted of 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

Mention may also be made of the acrylic acid/lauryl methacrylate/vinylpyrrolidone terpolymer sold under the name Acrylidone LM by the company ISP;

(c) maleic anhydride/$C_{30}$-$C_{33}$ α-olefin/alkyl maleate terpolymers, such as the product (maleic anhydride/$C_{30}$-$C_{33}$ α-olefin/isopropyl maleate copolymer) sold under the name Performa V 1608® by the company Newphase Technologies;

(d) acrylic terpolymers comprising:
i) approximately 20% to 70% by weight of an α,β-monoethylenically unsaturated carboxylic acid [A],
ii) approximately 20% to 80% by weight of an α,β-monoethylenically unsaturated non-surfactant monomer other than [A],
iii) approximately 0.5% to 60% by weight of a nonionic monourethane which is the product of reaction of a monohydric surfactant with a monoethylenically unsaturated monoisocyanate, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 OE) terpolymer, as an aqueous 25% dispersion;

(e) copolymers comprising among their monomers an α,β-monoethylenically unsaturated carboxylic acid and an ester of an α,β-monoethylenically unsaturated carboxylic acid and of an oxyalkylenated fatty alcohol.

Preferably, these compounds also comprise as monomer an ester of an α,β-monoethylenically unsaturated carboxylic acid and of a $C_1$-$C_4$ alcohol.

An example of a compound of this type that may be mentioned is Aculyn 22® sold by the company Röhm & Haas, which is a methacrylic acid/ethyl acrylate/oxyalkylenated stearyl methacrylate terpolymer;

(f) amphiphilic polymers comprising at least one ethylenically unsaturated monomer bearing a sulfonic group, in free or partially or totally neutralized form and comprising at least one hydrophobic part. These polymers may be crosslinked or non-crosslinked. They are preferably crosslinked.

The ethylenically unsaturated monomers bearing a sulfonic group are in particular chosen from vinylsulfonic acid, styrenesulfonic acid, (meth)acrylamido($C_1$-$C_{22}$)alkylsulfonic acids, N—($C_1$-$C_{22}$)alkyl(meth)acrylamido($C_1$-$C_{22}$)alkylsulfonic acids such as undecylacrylamidomethanesulfonic acid, and also partially or totally neutralized forms thereof.

More preferably, use will be made of (meth)acrylamido ($C_1$-$C_{22}$)alkylsulfonic acids, such as, for example, acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also their partially or totally neutralized forms.

2-Acrylamido-2-methylpropanesulfonic acid (AMPS), and also partially or totally neutralized forms thereof, will more particularly be used.

The polymers of this family may be chosen in particular from random amphiphilic AMPS polymers modified by reaction with a C6-C22 n-monoalkylamine or di-n-alkylamine, and such as those described in patent application WO 00/31154 (which form an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid and maleic acid, or mixtures of these compounds.

The preferred polymers of this family are chosen from amphiphilic copolymers of AMPS and of at least one ethylenically unsaturated hydrophobic monomer.

These same copolymers may also contain one or more ethylenically unsaturated monomers not comprising a fatty chain, such as (meth)acrylic acids, 3-substituted alkyl derivatives thereof or esters thereof obtained with monoalcohols or mono- or polyalkylene glycols, (meth)acrylamides, vinylpyrrolidone, maleic anhydride, itaconic acid and maleic acid, or mixtures of these compounds.

These copolymers are described in particular in patent application EP-A-750 899, U.S. Pat. No. 5,089,578 and in the following publications from Yotaro Morishima:

«Self-assembling amphiphilic polyelectrolytes and their nanostructures—Chinese *Journal of Polymer Science* Vol. 18, N°40, (2000), 323-336.»

«Miscelle formation of random copolymers of sodium 2-(acrylamido)-2-methylpropanesulfonate and a non-ionic surfactant macromonomer in water as studied by fluorescence and dynamic light scattering—*Macromolecules*, Vol. 33, N° 10 (2000), 3694-3704»;

«Solution properties of miscelle networks formed by non-ionic moieties covalently bound to an polyelectrolyte: salt effects on rheological behavior—*Langmuir*, Vol. 16, N° 12, (2000) 5324-5332»;

«Stimuli responsive amphiphilic copolymers of sodium 2-(acrylamido)-2-methylpropanesulfonate and associative macromonomers—*Polym. Preprint, Div. Polym. Chem.*, 40(2), (1999), 220-221».

Among these polymers, mention may be made of:

crosslinked or non-crosslinked, neutralized or non-neutralized copolymers, comprising from 15% to 60% by weight of AMPS units and from 40% to 85% by weight of ($C_8$-$C_{16}$)alkyl(meth)acrylamide or ($C_8$-$C_{16}$)alkyl (meth)acrylate units relative to the polymer, such as those described in patent application EP-A750 899;

terpolymers comprising from 10 mol % to 90 mol % of acrylamide units, from 0.1 mol % to 10 mol % of AMPS units and from 5 mol % to 80 mol % of n-($C_6$-$C_{18}$)alkylacrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Among the cationic associative polymers, mention may be made of:

(I) cationic associative polyurethanes;

(II) the compound sold by the company Noveon under the name Aqua CC and which corresponds to the INCI name Polyacrylate-1 Crosspolymer.

Polyacrylate-1 Crosspolymer is the product of polymerization of a monomer mixture comprising:

a di($C_1$-$C_4$ alkyl)amino($C_1$-$C_6$ alkyl) methacrylate, one or more $C_1$-$C_{30}$ alkyl esters of (meth)acrylic acid, a polyethoxylated $C_{10}$-$C_{30}$ alkyl methacrylate (20-25 mol of ethylene oxide units), a 30/5 polyethylene glycol/polypropylene glycol allyl ether, a hydroxy($C_2$-$C_6$ alkyl) methacrylate, and an ethylene glycol dimethacrylate;

(III) quaternized (poly)hydroxyethylcelluloses modified with groups comprising at least one fatty chain, such as alkyl, arylalkyl or alkylaryl groups comprising at least 8 carbon atoms, or mixtures thereof. The alkyl radicals borne by the above quaternized celluloses or hydroxyethylcelluloses preferably comprise from 8 to 30 carbon atoms. The aryl radicals preferably denote phenyl, benzyl, naphthyl or anthryl groups. Examples of quaternized alkylhydroxyethylcelluloses containing $C_8$-$C_{30}$ fatty chains that may be indicated include the products Quatrisoft LM 200®, Quatrisoft LM-X 529-18-A®, Quatrisoft LM-X 529-18-B® ($C_{12}$ alkyl) and Quatrisoft LM-X 529-8® ($C_{18}$ alkyl) sold by the company Aqualon, and the products Crodacel QM®, Crodacel QL® ($C_{12}$ alkyl) and Crodacel QS® ($C_{18}$ alkyl) sold by the company Croda and the product Softcat SL 100® sold by the company Aqualon;

(IV) cationic polyvinyllactam polymers.

Such polymers are described, for example, in patent application WO-00/68282.

As cationic poly(vinyllactam) polymers according to the invention, vinylpyrrolidone/dimethylaminopropylmethacrylamide/dodecyldimethylmethacryl-amidopropylammonium tosylate terpolymers, vinylpyrrolidone/dimethylaminopropylmethacrylamide/cocoyldimethylmethacrylamidopropylammonium tosylate terpolymers, vinylpyrrolidone/dimethylaminopropylmethacrylamide/ lauryldimethylmethacrylamidopropyl ammonium tosylate or chloride terpolymers are used in particular.

The amphoteric associative polymers are preferably chosen from those comprising at least one noncyclic cationic unit. Even more particularly, those prepared from or comprising 1 mol % to 20 mol %, preferably 1.5 to 15 mol % and even more particularly 1.5 to 6 mol % of fatty-chain monomer relative to the total number of moles of monomers are preferred.

Amphoteric associative polymers according to the invention are described and prepared, for example, in patent application WO 98/44012.

Among the amphoteric associative polymers according to the invention, the ones that are preferred are acrylic acid/ (meth)acrylamidopropyltrimethylammonium chloride/ stearyl methacrylate terpolymers.

The associative polymers of nonionic type that may be used according to the invention are preferably chosen from:

(a) copolymers of vinylpyrrolidone and of fatty-chain hydrophobic monomers, of which examples that may be mentioned include:

the products Antaron V216® or Ganex V216® (vinylpyrrolidone/hexadecene copolymer) sold by the company I.S.P.

the products Antaron V220® or Ganex V220® (vinylpyrrolidone/eicosene copolymer) sold by the company I.S.P.;

(b) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®;

(c) copolymers of hydrophilic methacrylates or acrylates and of hydrophobic monomers comprising at least one fatty chain, for instance the polyethylene glycol methacrylate/lauryl methacrylate copolymer;

(d) polyurethane polyethers comprising in their chain both hydrophilic blocks usually of polyoxyethylenated nature and hydrophobic blocks, which may be aliphatic sequences alone and/or cycloaliphatic and/or aromatic sequences;

(e) polymers with an aminoplast ether backbone containing at least one fatty chain, such as the Pure Thix® compounds sold by the company Sud-Chemie;

(f) celluloses or derivatives thereof, modified with groups comprising at least one fatty chain, such as alkyl, arylalkyl or alkylaryl groups or mixtures thereof wherein the alkyl groups are of $C_8$, and in particular:
nonionic alkylhydroxyethylcelluloses such as the products Natrosol Plus Grade 330 CS and Polysurf 67 ($C_{16}$ alkyl) sold by the company Aqualon;
nonionic nonoxynylhydroxyethylcelluloses such as the product Amercell HM-1500 sold by the company Amerchol;
nonionic alkylcelluloses such as the product Bermocoll EHM 100 sold by the company Berol Nobel;
(g) associative guar derivatives, for instance hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be envisaged. In addition, the polymer may comprise a hydrocarbon-based chain at one end or at both ends of a hydrophilic block.

The polyurethane polyethers may be multiblock, in particular in triblock form. The hydrophobic blocks may be at each end of the chain (for example: triblock copolymer having a hydrophilic central block) or distributed both at the ends and in the chain (for example, multiblock copolymer). These same polymers may also be graft polymers or star polymers.

The nonionic fatty-chain polyurethane polyethers may be triblock copolymers, the hydrophilic block of which is a polyoxyethylene chain comprising from 50 to 1000 oxyethylene groups. The nonionic polyurethane polyethers comprise a urethane bond between the hydrophilic blocks, hence the origin of the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Röhm & Haas containing a $C_{20}$ alkyl chain and a urethane bond, sold at a solids content of 20% in water, may also be used.

Use may also be made of solutions or dispersions of these polymers, in particular in water or in aqueous/alcoholic medium. Examples of such polymers that may be mentioned are Rheolate® 255, Rheolate® 278 and Rheolate® 244 sold by the company Rheox. The products DW 1206F and DW 1206J sold by the company Röhm & Haas may also be used.

The polyurethane polyethers which can be used according to the invention are in particular those described in the paper by G. Fonnum, J. Bakke and Fk. Hansen—*Colloid Polym. Sci.*, 271, 380-389 (1993).

It is even more particularly preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold in particular by the company Röhm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

According to one particular embodiment of the invention, the composition (2) comprises one or more nonionic, cationic or amphoteric, preferably cationic or amphoteric, substantive polymer(s). More particularly, the substantive polymers are chosen from cationic polymers.

The substantive nature (i.e. the capacity for deposition onto the hair) of the polymers is conventionally determined using the test described by Richard J. Crawford, Journal of the Society of Cosmetic Chemists, 1980, 31-(5)-pages 273 to 278 (detection with Red 80 acid dye).

These substantive polymers are in particular described in the literature in patent application EP-A-0 557 203.

Among the substantive polymers of the dimethyldiallylammonium halide homopolymer or copolymer type that may be used according to the invention, mention may be made in particular of:
polymers of diallyldimethylammonium salts, in particular diallyldimethylammonium halides (chloride), for instance polyquaternium-6;
copolymers of salts of diallyldimethylammonium and of acrylic acid, in particular halides (chloride) of salts of diallyldimethylammonium and of acrylic acid, for instance that with proportions (80/20 by weight) sold under the name Merquat 280 Dry by the company Calgon;
copolymers of diallyldimethylammonium salts, in particular halides (chloride) of diallyldimethylammonium and of acrylamide.

Among the substantive polymers of the methacryloyloxyethyltrimethylammonium halide polymer type that may be used according to the invention, mention may be made in particular of the products that are known in the CTFA dictionary (5th edition, 1993) as Polyquaternium 37, Polyquaternium 32 and Polyquaternium 35, which correspond respectively, as regards Polyquaternium 37, to crosslinked poly(methacryloyloxyethyltrimethylammonium chloride), in dispersion at 50% in mineral oil, and sold under the name Salcare SC95 by the company Allied Colloids; as regards Polyquaternium 32, to the crosslinked copolymer of acrylamide and methacryloyloxyethyltrimethylammonium chloride (20/80 by weight), in dispersion at 50% in mineral oil, and sold under the name Salcare SC92 by the company Allied Colloids; and as regards Polyquaternium 35, to the methosulfate of the methacryloyloxyethyltrimethylammonium/methacryloyloxyethyldimethylacetylammonium copolymer.

The substantive polymers of the quaternary polyammonium type that may be used according to the invention are as follows:
polymers constituted of repeating units corresponding to formula (α) below: $-(CH_3)_2N^+-(CH_2)_3-(CH_3)_2N^+-(CH_2)_6-$, $2X^-$ with $X^-$, which may be identical or different, representing an anionic counterion as defined previously, in particular a halide such as Cl⁻, these polymers being prepared and described in French patent 2 270 846; preference is given to the polymers with repeating units of formula (α) of which the molecular weight, determined by gel permeation chromatography, is between 9500 and 9900;

polymers constituted of repeating units corresponding to formula (β) below: —(CH$_3$)$_2$N$^+$—(CH$_2$)$_3$—(CH$_3$)$_2$N$^+$—(CH$_2$)$_3$—, 2X⁻ with X⁻ as defined for (α), these polymers being prepared and described in French patent 2 270 846; preference is given to the polymers with repeating units of formula (β) of which the molecular weight, determined by gel permeation chromatography, is about 1200;

polymers constituted of repeating units corresponding to formula (γ) below: —(CH$_3$)$_2$N$^+$—(CH$_2$)$_p$—N(H)—C(O)-G-N(H)—(CH$_2$)$_p$—(CH$_3$)$_2$N$^+$—(CH$_2$)$_2$—O—(CH$_2$)$_2$—, 2X⁻ wherein p denotes an integer ranging from 1 to 6 approximately, G may represent a bond or a group —(CH$_2$)$_r$—C(O)— wherein r denotes an integer equal to 4 or 7, these polymers being prepared and described in patents U.S. Pat. Nos. 4,157,388, 4,390,689, 4,702,906 and 4,719,282; preference is given to the polymers with repeating units of formula (γ) of which the molecular weight is less than 100 000 and preferably less than or equal to 50 000.

Preferably, the polymer(s) of the invention are chosen from nonassociative thickening polymers and more preferentially chosen from cellulose-based polymers, in particular (poly)hydroxy(C$_1$-C$_4$)alkylcellulose nonionic cellulose ethers, such as hydroxyethylcellulose (HEC), and microbial gums such as xanthan gum.

Preferably, the composition (2) comprises one or more polymers, preferably chosen from nonassociative thickening polymers and more preferentially chosen from cellulose-based polymers, in particular (poly)hydroxy(C$_1$-C$_4$)alkylcellulose nonionic cellulose ethers, such as hydroxyethylcellulose (HEC), and microbial gums such as xanthan gum.

When it (they) is (are) present, the polymer(s) is (are) present in the composition (2) according to the invention in a content ranging from 0.01% 10% by weight and preferably from 0.1% to 5% by weight, more preferentially from 0.5% to 3% by weight relative to the total weight of the composition (2).

The dye composition (2) and that derived from mixing (1) and (2) that are useful in the context of the invention may be in various forms, such as in the form of liquids, creams or gels, or in any other form that is suitable for dyeing keratin fibers, and in particular human hair.

The dyeing process of the invention comprises mixing, just before use, the composition (1) with the composition (2) and applying the mixture of the composition resulting from the mixture (1)+(2) to the keratin fibers.

The mixing of the process is carried out while preferably adhering to a composition (1)/composition (2) weight ratio of between 10/1 and 1/10, better still between 1/1 and 1/5, such as 1/4.

The composition (1) and/or the composition (2) that is useful in the context of the invention may furthermore comprise an oxidation base. This oxidation base may be chosen from the oxidation bases conventionally used in oxidation dyeing, for example para-phenylenediamines, bis(phenyl)alkylenediamines, para-aminophenols, ortho-aminophenols and heterocyclic bases.

Among the para-phenylenediamines, examples that may be mentioned more particularly include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 2-(2,5-diaminophenyl)ethanol, 2-(methoxymethyl)benzene-1,4-diamine, 3(-2,5-diaminophenyl)propan-1-ol and 1-{3-[(4-aminophenyl)amino]propyl}-3-methyl-1H-imidazol-3-ium chloride, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, 2-(2,5-diaminophenyl)ethanol, 2-(methoxymethyl)benzene-1,4-diamine, 3(-2,5-diaminophenyl)propan-1-ol and 1-{3-[(4-aminophenyl)amino]propyl}-3-methyl-1H-imidazol-3-ium chloride, and the acid addition salts thereof, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid.

Among the heterocyclic bases, examples that may be mentioned include pyridine derivatives, pyrimidine derivatives and pyrazole derivatives, and derivatives of pyrazolo

[1,2-a]pyrazol-1-one type and derivatives of pyrazolopyridine type as described in European patent applications Nos 1 792 903 and 1 792 606.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made of the compounds described, for example, in patents DE 2 359 399; JP 88-169 571; JP 05 163 124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-aminopyrazolo[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a] pyrimidine-3,7-diamine, 2,5,N7,N7-tetramethylpyrazolo[1, 5-a]pyrimidine-3,7-diamine and 3-amino-5-methyl-7-imidazolylpropylaminopyrazolo[1,5-a]pyrimidine, and the addition salts thereof with an acid, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof with an acid.

Among the derivatives of pyrazolo[1,2a]pyrazol-1-one type, mention may be made of compounds such as 2,3-diamino-6,7-dihydro, 1H-5H-pyrazolo[1,2a]pyrazol-1-one.

The composition (1) and/or (2) that is useful in the context of the invention may also contain one or more couplers that are conventionally used for dyeing keratin fibers. Among these couplers, mention may be made in particular of meta-phenylenediamines, meta-aminophenols, meta-diphenols, naphthalene-based couplers and heterocyclic couplers.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2, 4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof with an acid.

In general, the addition salts with an acid that may be used in the context of the invention for the oxidation bases and the couplers are in particular chosen from the hydrochlorides, hydrobromides, sulfates, citrates, succinates, tartrates, lactates, tosylates, benzenesulfonates, phosphates and acetates.

If the oxidation base(s) are present in the dye composition (1) according to the invention, their amount preferably ranges from 0.001% to 10% by weight and more preferentially from 0.005% to 6% by weight relative to the total weight of the composition.

When they are present, the coupler(s) are generally present in an amount ranging from 0.001% to 10% by weight and even more preferentially from 0.005% to 6% by weight relative to the total weight of the composition.

The composition (1) and/or (2) that is useful in the context of the invention may optionally comprise at least one additional direct dye conventionally used for the dyeing of keratin fibers. It may be chosen from anionic, cationic and nonionic species.

Nonlimiting examples that may be mentioned include nitrobenzene dyes, azo, azomethine, methine, tetraazapentamethine, anthraquinone, naphthoquinone, benzoquinone, phenothiazine, indigoid, xanthene, phenanthridine and phthalocyanin dyes, triarylmethane-based dyes and natural dyes, alone or as mixtures.

It may be chosen, for example, from the following red or orange nitrobenzene dyes: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(β-aminoethyl)amino-2-nitro-4-(β-hydroxyethyloxy)benzene, 1-(β,γ-dihydroxypropyl)oxy-3-nitro-4-(β-hydroxyethyl) aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine and 1-amino-2-nitro-4-hydroxy-5-methylbenzene.

The additional direct dye may also be chosen from yellow and green-yellow nitrobenzene direct dyes. Examples that may be mentioned include the compounds chosen from: 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-bis (β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulfonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)amino-2-nitrobenzene and 4-(β-hydroxyethyl)amino-3-nitrobenzamide.

Mention may also be made of blue or violet nitrobenzene direct dyes, for instance 1-(β-hydroxyethyl)amino-4-N,N-bis(β-hydroxyethyl)amino-2-nitrobenzene, 1-(γ-hydroxypropyl)amino-4-N,N-bis(β-hydroxyethyl)amino-2-nitrobenzene, 1-(β-hydroxyethyl)amino-4-(N-methyl-N-β-hydroxyethyl)amino-2-nitrobenzene, 1-(β-hydroxyethyl)amino-4-(N-ethyl-N-β-hydroxyethyl)amino-2-nitrobenzene, 1-(β,γ-dihydroxypropyl)amino-4-(N-ethyl-N-β-hydroxyethyl)amino-2-nitrobenzene, and the 2-nitro-paraphenylenediamines of formula (III) below:

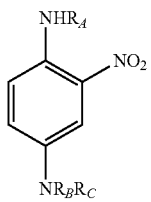

(IV)

in which formula (IV):
$R_B$ represents a $C_1$-$C_4$ alkyl radical or a β-hydroxyethyl, β-hydroxypropyl or γ-hydroxypropyl radical;
$R_A$ and $R_C$, which may be identical or different, represent a β-hydroxyethyl, β-hydroxypropyl, γ-hydroxypropyl or β,γ-dihydroxypropyl radical, at least one of the radicals $R_B$, $R_C$ or $R_A$ representing a γ-hydroxypropyl radical and $R_B$ and $R_C$ not being able simultaneously to denote a β-hydroxyethyl radical when R is a γ-hydroxypropyl radical.

These compounds of formula (III) can be found in French patent FR 2 692 572.

Among the azo direct dyes that can be used according to the invention, mention may be made of the cationic azo dyes described in patent applications WO 95/15144, WO 95/01772, EP 714 954, FR 2 822 696, FR 2 825 702, FR 2 825 625, FR 2 822 698, FR 2 822 693, FR 2 822 694, FR 2 829 926, FR 2 807 650, WO 02/078 660, WO 02/100 834, WO 02/100 369 and FR 2 844 269.

Among these compounds, mention may be made most particularly of the following dyes: 1,3-dimethyl-2-[[4-(dimethylamino)phenyl]azo]-1H-imidazolium halides, 1,3-dimethyl-2-[(4-aminophenyl)azo]-1H-imidazolium halides, 1-methyl-4-[(methylphenylhydrazono)methyl]pyridinium halides or alkyl sulfates.

Among the azo direct dyes that may also be mentioned are the following dyes, described in the Color Index International, 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone.

Among the azine dyes, mention may be made of the following compounds: Basic Blue 17, Basic Red 2.

Among the triarylmethane dyes that can be used according to the invention, mention may be made of the following compounds: Basic Green 1, Acid blue 9, Basic Violet 3, Basic Violet 14, Basic Blue 7, Acid Violet 49, Basic Blue 26, Acid Blue 7.

Among the indoamine dyes that may be used according to the invention, mention may be made of the following compounds: 2-β-hydroxyethlyamino-5-[bis(β-4'-hydroxyethyl)amino]anilino-1,4-benzoquinone, 2-β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N(3'-chloro-4'-methylamino)phenylureido-6-methyl-1,4-benzoquinoneimine and 3-[4'-N-(ethylcarbamylmethyl)amino]phenylureido-6-methyl-1, 4-benzoquinoneimine.

Among the dyes of tetraazapentamethine type that may be used according to the invention, mention may be made of the following compounds: 2-((E)-{(E)-[(1,3-dimethyl-1,3-dihydro-2H-imidazol-2-ylidene)hydrazono]methyl}diazenyl)-1,3-dimethyl-1H-imidazol-3-ium chloride; 2-{(E)-[(1Z)—N-(1,3-dimethyl-1,3-dihydro-2H-imidazol-2-ylidene)ethanehydrazonoyl]diazenyl}-1,3-dimethyl-1H-imidazol-3-ium chloride; 4-methoxy-2-((E)-{(1E)-1-[(2E)-(4-methoxy-1-methylpyridin-2(1H)-ylidene)hydrazono]ethyl}diazenyl)-1-methylpyridinium chloride; 1-methyl-2-((E)-{(1E)-1-[(2E)-(1-methylpyridin-2(1H)-ylidene)hydrazono]ethyl}diazenyl)pyridinium chloride; 1-(2-hydroxyethyl)-2-[(E)-((1E)-1-{(2E)-[1-(2-hydroxyethyl)pyridin-2(1H)-ylidene]hydrazono}ethyl)diazenyl] pyridinium chloride; 1-methyl-2-((E)-{(E)-[(2Z)-(1-methylpyridin-2(1H)-ylidene)hydrazono]methyl}diazenyl)pyridinium chloride; 1-(2-hydroxyethyl)-2-[(E)-((E)-{(2E)-[1-(2-hydroxyethyl)pyridin-2(1H)-ylidene] hydrazono}methyl)diazenyl]pyridinium acetate.

Among the additional natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Use may also be made of extracts or decoctions comprising these natural dyes and in particular henna-based poultices or extracts.

When they are present, the content of additional direct dyes in the composition generally ranges from 0.001% to 20% and preferably from 0.01% to 10% by weight relative to the weight of the composition.

The compositions (1) and (2) that are useful in the context of the invention may also contain various adjuvants conventionally used in hair dyeing compositions, such as mineral thickeners, antioxidants, penetration agents, sequestrants, fragrances, buffers, dispersants, conditioning agents such as, for example, volatile or nonvolatile, modified or nonmodified silicones, film-forming agents, ceramides, preservatives, opacifiers or clays. These above adjuvants are generally present in an amount, for each of them, of between 0.01% and 20% by weight relative to the weight of the composition.

Needless to say, those skilled in the art will take care to select this or these optional additional compound(s) such that the advantageous properties intrinsically associated with the dyeing composition that is useful in the context of the invention are not, or are not substantially, adversely affected by the envisaged addition(s).

The pH of the aqueous composition (2) that is useful in the context of the invention is generally between 3 and 12 approximately and preferably between 5 and 11 approximately. It can be adjusted to the desired value by means of acidifying or basifying agents regularly used in the dyeing of keratin fibers or alternatively using conventional buffer systems.

Among the acidifying agents, examples that may be mentioned include mineral acids, for instance hydrochloric acid, nitric acid or sulfuric acid, or organic acids, for instance compounds comprising at least one carboxylic acid function such as acetic acid, tartaric acid, citric acid or lactic acid, a sulfonic acid function, a phosphonic acid function or a phosphoric acid function.

Among the basifying agents, examples that may be mentioned include aqueous ammonia, alkali metal carbonates, alkanolamines, such as mono-, di- and triethanolamines and derivatives thereof, sodium hydroxide, potassium hydroxide and the compounds of formula (V) below:

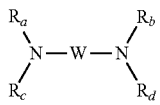
(V)

in which formula (V) W is a linear or branched ($C_1$-$C_6$) alkylene, such as propylene, optionally substituted with a hydroxyl group; $R_a$, $R_b$, $R_c$ and $R_d$, which may be identical or different, represent a hydrogen atom or a $C_1$-$C_4$ alkyl or $C_1$-$C_4$ hydroxyalkyl radical.

According to one particular embodiment, an oxidizing agent is used in the dyeing process. The oxidizing agent will also be necessary for obtaining simultaneous lightening of the keratin fibers (lightening dyeing) and/or when the composition (1) and/or (2) contain(s) oxidation bases or couplers.

When an oxidizing agent is used, it may be present in the composition (2) of the invention. Alternatively it may be mixed just before use with (1) and (2). The oxidizing agent(s) may also be applied separately, as a pretreatment or post-treatment.

The oxidizing agent may be chosen from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. The oxidizing agent will preferably be hydrogen peroxide.

In the case where the oxidizing agent(s) are present in the composition (2) according to the invention, their amount will preferably range from 1% to 95% by weight and better still from 5% to 50% by weight relative to the total weight of the composition.

In the dyeing process of the invention, the application of the composition resulting from the mixing of the compositions (1) and (2) as defined previously may or may not be followed by rinsing.

The leave-on time, on keratin fibers, in particular human keratin fibers such as the hair, of the composition resulting from the mixing of the compositions (1) and (2) is generally between 3 and 60 minutes, preferably between 5 and 40 minutes, even more preferentially between 10 and 30 minutes.

The application temperature generally used is ambient temperature, preferably between 25 and 55° C.

After application of the mixture of the compositions (1) and (2) to the keratin fibers, for a leave-on time as defined previously, and at a temperature between 25 and 55° C., the keratin fibers are preferably rinsed, shampooed and dried.

According to one particular embodiment of the dyeing process of the invention, i) the mixture of the compositions (1) and (2) is applied to the keratin fibers for a leave-on-time and at a temperature as defined previously, ii) the fibers are optionally rinsed, shampooed and dried, and then the dyeing process of the invention which carries out step i) and optionally step ii) is repeated from 1 to 6 times, preferably from 1 to 4 times, more preferentially from 1 to 3 times.

A subject of the present invention is also a multi-compartment device or kit comprising at least two separate compartments comprising, in the first compartment, the composition (1) as defined previously and, in a second compartment, the composition (2) as defined previously. Such a kit makes it possible to carry out the process for dyeing keratin fibers described above.

The examples that follow serve to illustrate the invention without, however, being limiting in nature.

EXAMPLES

Example 1: Synthesis of the Dye Having the Following Formula

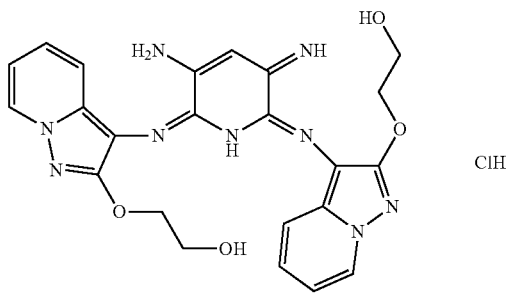

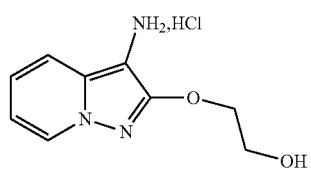 + 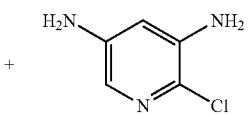 → 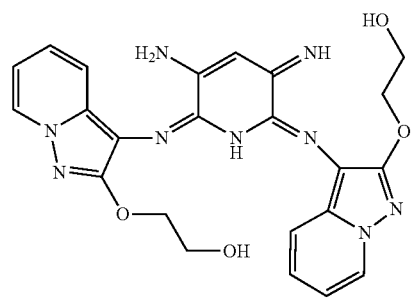

500 ml of ethanol are placed in a 1-liter one-necked round-bottomed flask equipped with a calcium chloride guard tube, followed by addition, with stirring, of 50 g (0.2177 mol) of 2-[(3-aminopyrazolo[1,5-a]pyridin-2-yl)oxy]ethanol hydrochloride. 14.2 g (0.986 mol) of 2-chloropyridine-3,5-diamine and 60.3 ml (0.346 mol) of N-ethyl-N-(propan-2-yl)propan-2-amine are added to this solution.

The solution thus obtained is stirred at ambient temperature for 4 days. The black precipitate formed is isolated by filtration, washed with water and dried in a desiccator under vacuum at 30° C. in the presence of a desiccant, to constant weight. A black solid is thus obtained.

The spectrometric analyses show that the compound obtained corresponds to the above structure.

Example 2

The Following Compositions were Produced:
Composition (1)

| ingredients | % by weight (g) |
| --- | --- |
| Dye of example 1 | 2.44 |
| Benzyl alcohol | 24.39 |
| Ethanol | qs 100 |

Composition (2)

| Ingredients | % by weight (g) |
| --- | --- |
| Hydroxyethylcellulose | 0.881 |
| Xanthan Gum | 0.377 |
| Triethanolamine | 0.176 |
| Phenoxyethanol | 1.258 |
| Caprylyl glycol | 1.258 |
| Water | qs 100 |

At the time of use, 20.5 g of composition (1) are mixed with 79.5 g of composition (2). After mixing the composition (1) with (2), a gel with a pH=7 is obtained.

The mixture is applied to locks of natural hair containing 90% gray hairs.

1st Application:

After a leave-on time of 30 min at ambient temperature (27° C.), the hair is rinsed, shampooed and then dried. Hair with a uniform "light gray" shade is obtained.

The 2nd, 3rd, 4th and 5th applications are carried out in an identical manner to the first.

A gradual* coloring is then obtained, which, after several consecutive applications, tends toward a natural dark gray.

*Gradual means that, after each application, a significant darkening and/or uptake of color is obtained after each application.

The colors of the locks thus obtained with dye 1 used in the same pH 7 dye support were evaluated in the CIE L* a* b* system, using a Minolta Spectrophotometer CM2600D colorimeter (specular components included, illuminant D65, angle 10°).

In this L* a* b* system, the three parameters denote, respectively, L*: the color intensity, a*: the green/red color axis, and b*: the blue/yellow color axis. For the intensity, the lower the value, the darker and more intense the color.

The variation in coloring or gain in color build-up is the difference in color between the locks of natural gray hair (NG) treated with the composition according to the invention, and the untreated locks, and is measured by (ΔE) according to the following equation:

$$\Delta E = \sqrt{(L^*-L_o^*)^2 + (a^*-a_o^*)^2 + (b^*-b_o^*)^2}$$

In this equation, L*, a* and b* represent the values measured on NG dyed hair according to the invention, and L0*, a0* and b0* represent the values measured on the untreated locks.

The higher the value of ΔE, the greater the gain in color build-up.

The results are indicated in the table below.

| Dye of example (1) | L | a | b | ΔE |
| --- | --- | --- | --- | --- |
| 1st application | 36.6 | 0.3 | 4.4 | 33.50 |
| 2nd application | 31.6 | 0.2 | 2.8 | 38.73 |
| 3rd application | 28.5 | 0.4 | 2.3 | 41.79 |
| 4th application | 26.5 | 0.2 | 1.4 | 43.98 |

It thus appears that the dyeing process according to the invention makes it possible to obtain very effective coloring in particular in terms of color uptake and of strength, this being as soon as the first application.

The invention claimed is:

1. A process for dyeing keratin fibers which comprises mixing together at least compositions (1) and (2) and applying the mixture to the keratin fibers, wherein:

composition (1) is anhydrous and comprises one or more dyes chosen from compounds of formulae (I) and/or (II) below:

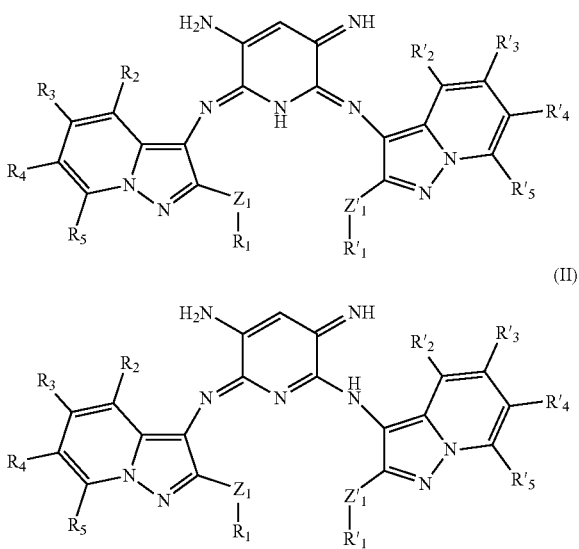

wherein in formulae (I) and (II):

$Z_1$ represents an oxygen atom or a group —N(R$_6$)—;

$Z'_1$ represents an oxygen atom or a group —N(R'$_6$)—;

with the proviso that when $Z_1$ represents —N(R$_6$)— and/or $Z'_1$ represents —N(R'$_6$)—, then $R_1$ and $R_6$ and/or $R'_1$ and $R'_6$, respectively, may form, together with the nitrogen atom to which they are attached, an optionally substituted, 5- to 8-membered, optionally cationic, saturated, unsaturated, or aromatic heterocycle;

$R_1$, $R'_1$, $R_6$, and $R'_6$ each independently represent:

a hydrogen atom, a $C_1$-$C_{10}$ alkyl radical optionally interrupted with one or more non-adjacent heteroatoms, and/or optionally substituted;

$R_2$, $R_3$, $R_4$, $R_5$, $R'_2$, $R'_3$, $R'_4$, and $R'_5$ each independently represent:

a hydrogen atom, an optionally substituted $C_1$-$C_4$ alkyl radical, or a group chosen from —NH$_2$, —N(H)R$_{10}$, —N(R$_{11}$)R$_{12}$, OH, or —OR$_9$, with R$_9$ and R$_{10}$ representing an optionally substituted, linear or branched $C_1$-$C_6$ alkyl, R$_{11}$ and R$_{12}$, which may be identical or different, representing an optionally substituted, linear or branched $C_1$-$C_6$ alkyl, wherein R$_{11}$ and R$_{12}$ optionally form, together with the nitrogen atom to which they are attached, a saturated, unsaturated or aromatic 5- to 8-membered heterocycle optionally containing one or more other heteroatoms or groups chosen from N, O, S, S(O)$_2$, or C(O), the heterocycle being optionally substituted, and/or $R_2$, $R_3$, $R_4$, $R_5$, $R'_2$, $R'_3$, $R'_4$, and $R'_5$ form, in pairs with adjacent radicals, an optionally substituted, saturated or unsaturated (hetero)cycle;

wherein when the compound of formula (I) and/or (II) is positively charged, then it comprises as many anionic counterions as cationic charges to achieve the electrical neutrality of the molecule; and composition (2) is aqueous, and comprises one or more ingredients chosen from:

i) hydrotropic solvents;

ii) anionic surfactants, cationic surfactants, nonionic surfactants, amphoteric or zwitterionic surfactants, or mixtures of two or more thereof;

iii) anionic polymers, cationic polymers, nonionic polymers, amphoteric or zwitterionic polymers, any of which may be optionally associative, or optionally substantive, or mixtures of two or more thereof;

wherein composition (2) does not comprise any dye (I) or (II).

2. The process according to claim 1, wherein $R_1$ and $R'_1$ are chosen from the following groups:

i) $C_1$-$C_6$ alkyl;

ii) $C_1$-$C_{10}$ alkyl substituted with one or more hydroxyl groups;

iii) $C_1$-$C_6$ alkyl substituted with one or more amino or (di)(C$_1$-C$_4$) alkylamino groups;

iv) $C_1$-$C_6$ alkyl substituted with a nitrogenous heterocycle; or v) —[(CH$_2$)$_m$—O]$_p$-L-Y, with:
p=1, 2, or 3,
m=1, 2, or 3,
L chosen from linear or branched, saturated $C_1$-$C_6$ divalent hydrocarbon-based groups, and
Y chosen from hydroxyl groups or a hydrogen atom.

3. The process according to claim 1, wherein $R_2$, $R'_2$, $R_3$, $R'_3$, $R_4$, $R'_4$, $R_5$, and $R'_5$ independently represent a hydrogen atom or a $C_1$-$C_4$ alkyl radical.

4. The process according to claim 1, wherein the compound(s) of formula (I) and/or (II) are chosen from those of formulae (I') or (II'):

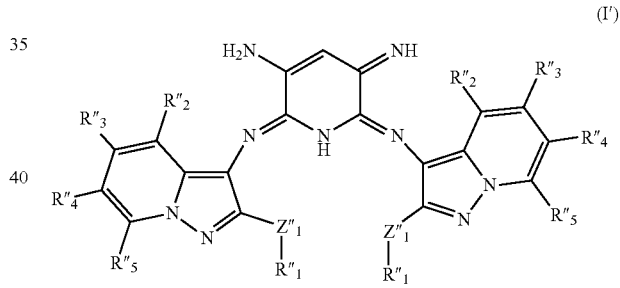

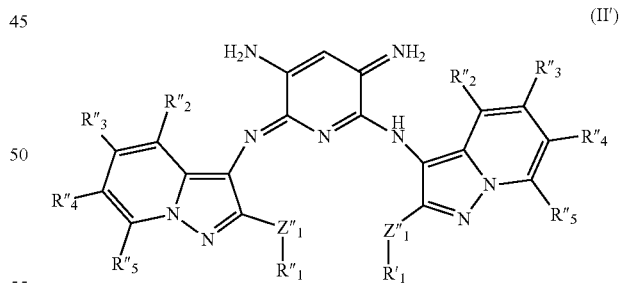

wherein in formulae (I') and (II'):

$Z''_1$ is chosen from an oxygen atom or a group —N(R''$_6$)—;

with the proviso that when $Z''_1$ represents —N(R''$_6$)—, then R''$_1$ and R''$_6$ may form, together with the nitrogen atom to which they are attached, an optionally substituted, 5- or 6-membered, saturated, unsaturated or aromatic heterocycle;

R''$_1$ represents a $C_1$-$C_6$ alkyl radical, optionally interrupted with one or more non-adjacent oxygen atoms, and/or optionally substituted with:

a hydroxyl radical,
a di($C_1$-$C_4$)alkylamino radical, or
a heterocycle optionally substituted with one or more $C_1$-$C_4$ alkyl and/or hydroxyl radicals and chosen selected from pyrrolidine, piperidine, morpholine, piperazine, or imidazole;

R"$_6$ represents:
a hydrogen atom, or
a $C_1$-$C_{10}$ alkyl radical optionally substituted with a hydroxyl radical; and R"$_2$, R"$_3$, R"$_4$, and R"$_5$ each independently represent:
a hydrogen atom, or
a $C_1$-$C_4$ alkyl radical.

5. The process according to claim 4, wherein Z"$_1$ represents NH, and R"1 denotes a $C_1$-$C_6$ hydroxyalkyl radical, a di($C_1$-$C_4$ alkyl)amino($C_1$-$C_6$ alkyl) radical, or an alkyl radical substituted with a heterocycle chosen from pyrrolidinyl, piperidyl, morpholinyl, piperazinyl, or imidazolyl, said heterocycle being optionally substituted with one or more $C_1$-$C_4$ alkyl radicals.

6. The process according to claim 4, wherein Z"$_1$ represents —N(R"$_6$)—, and:
R"$_1$ and R"$_6$ each independently denote a $C_1$-$C_6$ alkyl radical or a $C_1$-$C_6$ hydroxyalkyl radical; or
R"$_1$ forms with R"$_6$ a ring, this ring being chosen from pyrrolidinyl, piperidyl, morpholinyl, or piperazinyl rings optionally substituted with one or more $C_1$-$C_4$ alkyl and/or hydroxyl radicals.

7. The process according to claim 4, wherein the compound(s) of formula (I), (II), (I'), or (II') are chosen from: 2,2'-[(5-amino-3-iminopyridine-2,6(1H,3H)-diylidene)bis(nitrilopyrazolo[1,5-a]pyridine-3,2-diylimino)]diethanol; 3,3'-[(5-amino-3-iminopyridine-2,6(1H,3H)-diylidene)bis(nitrilopyrazolo[1,5-a]pyridine-3,2-diylimino)]dipropan-1-ol; N3,N3'-(5-amino-3-iminopyridine-2,6(1H,3H)-diylidene)bis{N2-[2-(dimethylamino)ethyl]pyrazolo[1,5-a]pyridine-2,3-diamine}; N3,N3'-(5-amino-3-iminopyridine-2,6(1H,3H)-diylidene)bis{N2-[3-(dimethylamino)propyl]pyrazolo-[1,5-a]pyridine-2,3-diamine}; N3,N3'-(5-amino-3-iminopyridine-2,6(1H,3H)-diylidene)-bis{N2-[2-(pyrrolidin-1-yl)ethyl]pyrazolo[1,5-a]pyridine-2,3-diamine}; N3,N3'-(5-amino-3-iminopyridine-2,6(1H,3H)-diylidene)bis{N2-[3-(pyrrolidin-1-yl)propyl]pyrazolo[1,5-a]pyridine-2,3-diamine}; N3,N3'-(5-amino-3-iminopyridine-2,6(1H,3H)-diylidene)bis{N2-[2-(piperidin-1-yl)ethyl]pyrazolo[1,5-a]pyridine-2,3-diamine}; N3,N3'-(5-amino-3-iminopyridine-2,6(1H,3H)-diylidene)bis{N2-[3-(piperidin-1-yl)propyl]pyrazolo[1,5-a]pyridine-2,3-diamine}; N3,N3'-(5-amino-3-iminopyridine-2,6(1H,3H)-diylidene)bis{N2-[2-(morpholin-4-yl)ethyl]pyrazolo[1,5-a]pyridine-2,3-diamine}; N3,N3'-(5-amino-3-iminopyridine-2,6(1H,3H)-diylidene)bis{N2-[3-(morpholin-4-yl)propyl]pyrazolo[1,5-a]pyridine-2,3-diamine}; N3,N3'-(5-amino-3-iminopyridine-2,6(1H,3H)-diylidene)bis{N2-[2-(4-methylpiperazin-1-yl)ethyl]pyrazolo[1,5-a]pyridine-2,3-diamine}; N3,N3'-(5-amino-3-iminopyridine-2,6(1H,3H)-diylidene)bis{N2-[3-(4-methylpiperazin-1-yl)propyl]pyrazolo-[1,5-a]pyridine-2,3-diamine}; N3,N3'-(5-amino-3-iminopyridine-2,6(1H,3H)-diylidene)bis{N2-[2-(1H-imidazol-1-yl)ethyl]pyrazolo[1,5-a]pyridine-2,3-diamine; N3,N3'-(5-amino-3-iminopyridine-2,6(1H,3H)-diylidene)bis{N2-[3-(1H-imidazol-1-yl)propyl]pyrazolo[1,5-a]pyridine-2,3-diamine}; 2,2'-[(5-amino-3-iminopyridine-2,6(1H,3H)-diylidene)bis(nitrilopyrazolo[1,5-a]pyridine-3,2-diyloxy)]diethanol; 3,3'-[(5-amino-3-iminopyridine-2,6(1H,3H)diylidene)bis(nitrilopyrazolo[1,5-a]pyridine-3,2-diyloxy)]dipropan-1-ol; N,N'-(5-amino-3-iminopyridine-2,6(1H,3H)-diylidene)bis{2-[2-(dimethylamino)ethoxy]pyrazolo[1,5-a]pyridin-3-amine}; N,N'-(5-amino-3-iminopyridine-2,6(1H,3H)-diylidene)bis{2-[3-(dimethylamino)propoxy]pyrazolo[1,5-a]pyridin-3-amine}; N,N'-(5-amino-3-iminopyridine-2,6(1H,3H)-diylidene) bis{2-[2-(pyrrolidin-1-yl)ethoxy]pyrazolo[1,5-a]pyridin-3-amine}; N,N'-(5-amino-3-iminopyridine-2,6(1H,3H)-diylidene)bis{2-[3-(pyrrolidin-1-yl)propoxy]pyrazolo[1,5-a]pyridin-3-amine}; N,N'-(5-amino-3-iminopyridine-2,6(1H,3H)-diylidene)bis{2-[2-(piperidin-1-yl)ethoxy]pyrazolo[1,5-a]pyridin-3-amine}; N,N'-(5-amino-3-iminopyridine-2,6(1H,3H)-diylidene)bis{2-[3-(piperidin-1-yl)propoxy]pyrazolo[1,5-a]pyridin-3-amine}; N,N'-(5-amino-3-iminopyridine-2,6(1H,3H)-diylidene)bis{2-[2-(morpholin-4-yl)ethoxy]pyrazolo[1,5-a]pyridin-3-amine}; N,N'-(5-amino-3-iminopyridine-2,6(1H,3H)-diylidene) bis{2-[3-(morpholin-4-yl)propoxy]pyrazolo[1,5-a]pyridin-3-amine}; N,N'-(5-amino-3-iminopyridine-2,6(1H,3H)-diylidene)bis{2-[2-(4-methylpiperazin-1-yl)ethoxy] pyrazolo[1,5-a]pyridin-3-amine}; N,N'-(5-amino-3-iminopyridine-2,6(1H,3H)-diylidene)bis{2-[3-(4-methylpiperazin-1-yl)propoxy]pyrazolo[1,5-a]pyridin-3-amine}; N,N'-(5-amino-3-iminopyridine-2,6(1H,3H)-diylidene)bis{2-[2-(1H-imidazol-1-yl)ethoxy]pyrazolo[1,5-a]pyridin-3-amine}; N,N'-(5-amino-3-iminopyridine-2,6(1H,3H)-diylidene)bis{2-[3-(1H-imidazol-1-yl)propoxy]pyrazolo[1,5-a]pyridin-3-amine}; N,N'-(5-amino-3-iminopyridine-2,6(1H,3H)-diylidene)bis(2-methoxypyrazolo[1,5-a]pyridin-3-amine); N,N'-(5-amino-3-iminopyridine-2,6(1H,3H)-diylidene)bis(2-ethoxypyrazolo[1,5-a]pyridin-3-amine); N,N'-(5-amino-3-iminopyridine-2,6(1H,3H)-diylidene)bis(2-propoxypyrazolo[1,5-a]pyridin-3-amine); N,N'-(5-amino-3-iminopyridine-2,6(1H,3H)-diylidene)bis[2-(propan-2-yloxy)pyrazolo[1,5-a]pyridin-3-amine]; N,N'-(5-amino-3-iminopyridine-2,6(1H,3H)-diylidene)bis{2-[2-(2-ethoxyethoxy)ethoxy]-6,7-dimethylpyrazolo[1,5-a]pyridin-3-amine}; 2-{2-[(3-([3-amino-6-({2-[2-(2-hydroxyethoxy)ethoxy]pyrazolo[1,5-a]pyridin-3-yl}amino)-5-imino-5,6-dihydropyridin-2(1H)-ylidene]amino}pyrazolo[1,5-a]pyridin-2-yl)oxy]ethoxy}ethanol; N,N'-(5-amino-3-iminopyridine-2,6(1H,3H)-diylidene)bis{2-[2-(propan-2-yloxy)ethoxy]pyrazolo[1,5-a]pyridin-3-amine}; N,N'-(5-amino-3-iminopyridine-2,6(1H,3H)-diylidene)bis(2-tert-butoxypyrazolo[1,5-a]pyridin-3-amine); N3,N3'-(5-amino-3-iminopyridine-2,6(1H,3H)diylidene)bis{N2,N2-dimethylpyrazolo[-1,5-a]pyridine-2,3-diamine}; N3,N3'-(5-amino-3-iminopyridine-2,6(1H,3H)diylidene)bis{N2,N2-diethylpyrazolo[1,5-a]pyridine-2,3-diamine}; 2,2',2",2"'-[(5-amino-3-iminopyridine-2,6(1H,3H)-diylidene)bis (nitrilopyrazolo[1,5-a]pyridine-3,2-diylnitrilo)]tetraethanol; N,N'-(5-amino-3-iminopyridine-2,6(1H,3H)diylidene)bis [2-(pyrrolidin-1-yl)pyrazolo[1,5-a]pyridin-3-amine]; N,N'-(5-amino-3-iminopyridine-2,6(1H,3H)diylidene)bis[2-(piperidin-1-yl)pyrazolo[1,5-a]pyridin-3-amine]; N,N'-(5-amino-3-iminopyridine-2,6(1H,3H)diylidene)bis[2-(morpholin-4-yl)pyrazolo[1,5-a]pyridin-3-amine]; N,N'-(5-amino-3-iminopyridine-2,6(1H,3H)diylidene)bis[2-(4-methylpiperazin-1-yl)pyrazolo[1,5-a]pyridin-3-amine]; 1,1'-[(5-amino-3-iminopyridine-2,6(1H,3H)diylidene)bis(nitrilopyrazolo[1,5-a]pyridine-3,2-diyl)]dipyrrolidin-3-ol; 1,1'-[(5-amino-3-iminopyridine-2,6(1H,3H)diylidene)bis(nitrilopyrazolo[1,5-a]pyridine-3,2-diyl)]dipyrrolidine-3,4-diol; 2,2'-{(5-amino-3-iminopyridine-2,6(1H,3H)diylidene) bis[nitrilo(6,7-dimethylpyrazolo[1,5-a]pyridine-3,2-diyl)imino]}diethanol; 3,3'-{(5-amino-3-iminopyridine-2,6(1H,3H)diylidene)bis[nitrilo(6,7-dimethylpyrazolo-[1,5-a]

pyridine-3,2-diyl)imino]}dipropan-1-ol; N3,N3'-(5-amino-3-iminopyridine-2,6(1H,3H)diylidene)bis{N2-[2-(dimethylamino)ethyl]-6,7-dimethylpyrazolo[1,5-a]pyridine-2,3-diamine}; N3,N3'-(5-amino-3-iminopyridine-2,6(1H,3H)diylidene)bis{N2-[3-(dimethylamino)propyl]-6,7-dimethylpyrazolo[1,5-a]pyridine-2,3-diamine}; N3,N3'-(5-amino-3-iminopyridine-2,6(1H,3H)-diylidene)bis{6,7-dimethyl-N2-[2-(pyrrolidin-1-yl)ethyl]pyrazolo[1,5-a]pyridine-2,3-diamine}; N3,N3'-(5-amino-3-iminopyridine-2,6(1H,3H)-diylidene)bis{6,7-dimethyl-N2-[3-(pyrrolidin-1-yl)propyl]pyrazolo[1,5-a]pyridine-2,3-diamine}; N3,N3'-(5-amino-3-iminopyridine-2,6(1H,3H)diylidene)bis{6,7-dimethyl-N2-[2-(piperidin-1-yl)ethyl]pyrazolo-[1,5-a]pyridine-2,3-diamine}; N3,N3'-(5-amino-3-iminopyridine-2,6(1H,3H)diylidene)bis{6,7-dimethyl-N2-[3-(piperidin-1-yl)propyl]pyrazolo[1,5-a]pyridine-2,3-diamine}; N3,N3'-(5-amino-3-iminopyridine-2,6(1H,3H)diylidene)bis{6,7-dimethyl-N2-[2-(morpholin-4-yl)ethyl]pyrazolo[1,5-a]pyridine-2,3-diamine}; N3,N3'-(5-amino-3-iminopyridine-2,6(1H,3H)diylidene)bis{6,7-dimethyl-N2-[3-(morpholin-4-yl)propyl]pyrazolo[1,5-a]pyridine-2,3-diamine}; N3,N3'-(5-amino-3-iminopyridine-2,6(1H,3H)diylidene)bis{6,7-dimethyl-N2-[2-(4-methylpiperazin-1-yl)ethyl]pyrazolo[1,5-a]pyridine-2,3-diamine}; N3,N3'-(5-amino-3-iminopyridine-2,6(1H,3H)diylidene)bis{6,7-dimethyl-N2-[3-(4-methylpiperazin-1-yl)propyl]pyrazolo[1,5-a]pyridine-2,3-diamine}; N3,N3'-(5-amino-3-iminopyridine-2,6(1H,3H)-diylidene)bis{N2-[2-(1H-imidazol-1-yl)ethyl]-6,7-dimethylpyrazolo[1,5-a]pyridine-2,3-diamine}; N3,N3'-(5-amino-3-iminopyridine-2,6(1H,3H)-diylidene)bis{N2-[3-(1H-imidazol-1-yl)propyl]-6,7-dimethylpyrazolo[1,5-a]pyridine-2,3-diamine}; 2,2'-{(5-amino-3-iminopyridine-2,6(1H,3H)-diylidene)bis[nitrilo-(6,7-dimethylpyrazolo-[1,5-a]pyridine-3,2-diyl)oxy]}diethanol; 3,3'-{(5-amino-3-iminopyridine-2,6(1H,3H)-diylidene)bis[nitrilo(6,7-dimethylpyrazolo-[1,5-a]pyridine-3,2-diyl)oxy]}dipropan-1-ol; N,N'-(5-amino-3-iminopyridine-2,6(1H,3H)-diylidene)bis{2-[2-(dimethylamino)ethoxy]-6,7-dimethylpyrazolo[1,5-a]pyridin-3-amine; N3,N3'-(5-amino-3-iminopyridine-2,6(1H,3H)-diylidene)bis{N2-[3-(dimethylamino)propyl]-6,7-dimethyl-pyrazolo[1,5-a]pyridine-2,3-diamine}; N3,N3'-(5-amino-3-iminopyridine-2,6(1H,3H)-diylidene)bis{6,7-dimethyl-N2-[2-(pyrrolidin-1-yl)ethyl]pyrazolo[1,5-a]pyridine-2,3-diamine}; N,N'-(5-amino-3-iminopyridine-2,6(1H,3H)-diylidene)bis{6,7-dimethyl-2-[3-(pyrrolidin-1-yl)propoxy]pyrazolo[1,5-a]pyridin-3-amine}; N,N'-(5-amino-3-iminopyridine-2,6(1H,3H)-diylidene)bis{6,7-dimethyl-2-[2-(piperidin-1-yl)ethoxy]pyrazolo-[1,5-a]pyridin-3-amine}; N,N'-(5-amino-3-iminopyridine-2,6(1H,3H)-diylidene)bis{6,7-dimethyl-2-[3-(piperidin-1-yl)propoxy]pyrazolo[1,5-a]pyridin-3-amine}; N,N'-(5-amino-3-iminopyridine-2,6(1H,3H)-diylidene)bis{6,7-dimethyl-2-[2-(morpholin-4-yl)ethoxy]pyrazolo[1,5-a]pyridin-3-amine}; N,N'-(5-amino-3-iminopyridine-2,6(1H,3H)-diylidene)bis{6,7-dimethyl-2-[3-(morpholin-4-yl)propoxy]pyrazolo[1,5-a]pyridin-3-amine}; N,N'-(5-amino-3-iminopyridine-2,6(1H,3H)-diylidene)bis{6,7-dimethyl-2-[2-(4-methyl-piperazin-1-yl)ethoxy]pyrazolo[1,5-a]pyridin-3-amine}; N,N'-(5-amino-3-iminopyridine-2,6(1H,3H)-diylidene)bis{6,7-dimethyl-2-[3-(4-methylpiperazin-1-yl)propoxy]pyrazolo[1,5-a]pyridin-3-amine}; N,N'-(5-amino-3-iminopyridine-2,6(1H,3H)-diylidene)bis{2-[2-(1H-imidazol-1-yl)ethoxy]-6,7-dimethylpyrazolo[1,5-a]pyridin-3-amine}; N,N'-(5-amino-3-iminopyridine-2,6(1H,3H)-diylidene)bis{2-[3-(1H-imidazol-1-yl)propoxy]-6,7-dimethyl-pyrazolo[1,5-a]pyridin-3-amine}; N,N'-(5-amino-3-iminopyridine-2,6(1H,3H)-diylidene)bis{2-methoxy-6,7-dimethylpyrazolo[1,5-a]pyridin-3-amine}; N2-(2-ethoxy-6,7-dimethylpyrazolo[1,5-a]pyridin-3-yl)-6-[(2-ethoxy-6,7-dimethylpyrazolo[1,5-a]pyridin-3-yl)imino]-3-imino-3,6-dihydropyridine-2,5-diamine; N,N'-(5-amino-3-iminopyridine-2,6(1H,3H)-diylidene)bis{6,7-dimethyl-2-propoxypyrazolo[1,5-a]pyridin-3-amine}; N,N'-(5-amino-3-iminopyridine-2,6(1H,3H)-diylidene)bis[6,7-dimethyl-2-(propan-2-yloxy)-pyrazolo[1,5-a]pyridin-3-amine]; N,N'-(5-amino-3-iminopyridine-2,6(1H,3H)-diylidene)bis{2-tert-butoxy-6,7-dimethylpyrazolo[1,5-a]pyridin-3-amine}; N3,N3'-(5-amino-3-iminopyridine-2,6(1H,3H)-diylidene)bis{N2,N2,6,7-tetramethylpyrazolo[1,5-a]pyridine-2,3-diamine}; N3,N3'-(5-amino-3-iminopyridine-2,6(1H,3H)-diylidene)bis{N2,N2-diethyl-6,7-dimethylpyrazolo[1,5-a]pyridine-2,3-diamine}; 2,2',2'',2'''-{(5-amino-3-iminopyridine-2,6(1H,3H)-diylidene)bis[nitrilo(6,7-dimethyl-pyrazolo[1,5-a]pyridine-3,2-diyl)nitrilo]}tetraethanol; N,N'-(5-amino-3-iminopyridine-2,6(1H,3H)-diylidene)bis[6,7-dimethyl-2-(pyrrolidin-1-yl)pyrazolo[1,5-a]pyridin-3-amine]; N,N'-(5-amino-3-iminopyridine-2,6(1H,3H)-diylidene)bis[6,7-dimethyl-2-(piperidin-1-yl)pyrazolo[1,5-a]pyridin-3-amine]; N,N'-(5-amino-3-iminopyridine-2,6(1H,3H)-diylidene)bis[6,7-dimethyl-2-(morpholin-4-yl)pyrazolo[1,5-a]pyridin-3-amine]; N,N'-(5-amino-3-iminopyridine-2,6(1H,3H)-diylidene)bis[6,7-dimethyl-2-(4-methylpiperazin-1-yl)pyrazolo[1,5-a]pyridin-3-amine]; 1,1'-{(5-amino-3-iminopyridine-2,6(1H,3H)-diylidene)bis[nitrilo(6,7-dimethylpyrazolo[1,5-a]pyridine-3,2-diyl)]}dipyrrolidin-3-ol; 1,1'-{(5-amino-3-iminopyridine-2,6(1H,3H)-diylidene)bis[nitrilo(6,7-dimethylpyrazolo[1,5-a]pyridine-3,2-diyl)]}dipyrrolidine-3,4-diol or leuco forms thereof, optical isomers, geometrical isomers, tautomers, solvates or addition salts thereof.

8. The process according to claim 4, wherein the total amount of compound(s) of formulae (I), (I'), (II), and (II') ranges from 0.01% to 15% by weight.

9. The process according to claim 4, wherein the total amount of compound(s) of formulae (I), (I'), (II), and (II') ranges from 0.05% to 10% by weight.

10. The process according to claim 1, wherein the composition (1) comprises one or more hydrotropic solvent(s) chosen from alcohol ethers, aliphatic esters, aliphatic ethers, aromatic ethers, alkanols bearing aryl substituents, lactones, or mixtures of two or more thereof.

11. The process according to claim 1, wherein the composition (1) comprises one or more hydrotropic solvent(s) chosen from:
$C_1$-$C_4$ ethers of $C_5$-$C_{30}$ alcohols;
aliphatic esters of $C_1$-$C_4$ carboxylic acids and of $C_3$-$C_{10}$ monoalcohols or polyhydroxylated alcohols, interrupted with one or more non-adjacent ether functions;
aromatic ethers of a $C_6$-$C_{10}$ alkyl, optionally bearing a hydroxyl group;
($C_6$-$C_{10}$)aryl($C_1$-$C_6$)alkyl ethers, of a $C_1$-$C_6$ alkyl optionally bearing a hydroxyl group;
alkanols bearing an aryl substituent; or
lactones of formula (iii):

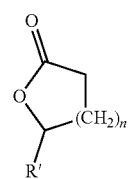

(iii)

wherein in formula (iii), R' represents a hydrogen, a linear or branched $C_1$-$C_8$ alkyl, or a linear or branched $C_1$-$C_4$ hydroxyalkyl, and n has the value 1, 2, or 3.

12. The process according to claim 1, wherein the composition (1) comprises one or more solvent(s) other than hydrotropic solvent(s), chosen from i) $C_1$-$C_4$ lower alkanols; ii) polyols; iii) polyol ethers; or mixtures of two or more thereof.

13. The process according to claim 1, wherein the composition (1) comprises one or more solvent(s) chosen from $C_1$-$C_4$ lower alkanols, present in an amount ranging from about 5% to 80% by weight, relative to the total weight of the composition (1).

14. The process according to claim 1, wherein composition (1) comprises one or more solvents other than hydrotropic solvents and composition (2) comprises one or more hydrotropic solvents chosen from alkanols bearing aryl substituents.

15. The process according to claim 1, wherein the composition (2) comprises one or more optionally associative, optionally substantive anionic, cationic, nonionic, amphoteric or zwitterionic polymers, or mixtures of two or more thereof.

16. The process according to claim 15, wherein the composition (2) comprises one or more polymer(s) chosen from (poly)hydroxy($C_1$-$C_4$)alkylcellulose nonionic cellulose ethers.

17. The process according to claim 1, wherein i) the mixture of the compositions (1) and (2) is applied to the keratin fibers and left on the keratin fibers for a leave-on time ranging from 3 to 60 minutes at a temperature ranging from 25-55° C., and ii) the keratin fibers are optionally subsequently rinsed, shampooed, and/or dried.

18. The process according to claim 1, wherein i) the mixture is applied to the keratin fibers and left on the keratin fibers for a leave-on time ranging from 10 to 30 minutes at a temperature ranging from 25-55° C., and ii) the keratin fibers are optionally subsequently rinsed, shampooed, and/or dried.

19. The process according to claim 17, wherein the dyeing process is repeated from 1 to 6 times.

20. A device or kit comprising at least two compartments separate from one another comprising, composition (1) in a first compartment and composition (2) in a second compartment, wherein:
  composition (1) is anhydrous and comprises one or more dyes chosen from compounds of formulae (I) and/or (II) below:

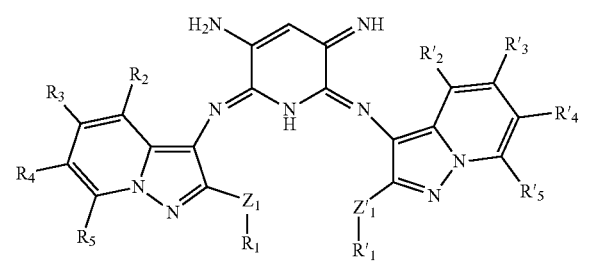

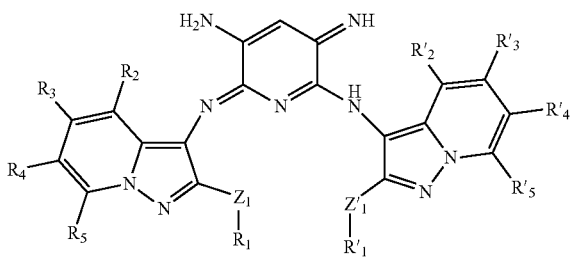

wherein in formulae (I) and (II):
  $Z_1$ represents an oxygen atom or a group —N($R_6$)—;
  $Z'_1$ represents an oxygen atom or a group —N($R'_6$)—;
    with the proviso that when $Z_1$ represents —N($R_6$)— and/or $Z'_1$ represents —N($R'_6$)—, then $R_1$ and $R_6$ and/or $R'_1$ and $R'_6$, respectively, may form, together with the nitrogen atom to which they are attached, an optionally substituted, 5- to 8-membered, optionally cationic, saturated, unsaturated, or aromatic heterocycle;
  $R_1$, $R'_1$, $R_6$, and $R'_6$ each independently represent:
    a hydrogen atom, or
    a $C_1$-$C_{10}$ alkyl radical optionally interrupted with one or more non-adjacent heteroatoms, and/or optionally substituted;
  $R_2$, $R_3$, $R_4$, $R_5$, $R'_2$, $R'_3$, $R'_4$, and $R'_5$ each independently represent:
    a hydrogen atom,
    an optionally substituted $C_1$-$C_4$ alkyl radical, or
    a group chosen from —$NH_2$, —N(H)$R_{10}$, —N($R_{11}$)$R_{12}$, —OH, or —O$R_9$, with $R_9$ and $R_{10}$ representing an optionally substituted, linear or branched $C_1$-$C_6$ alkyl, $R_{11}$ and $R_{12}$, which may be identical or different, representing an optionally substituted, linear or branched $C_1$-$C_6$ alkyl, wherein $R_{11}$ and $R_{12}$ optionally form, together with the nitrogen atom to which they are attached, a saturated, unsaturated or aromatic 5- to 8-membered heterocycle optionally containing one or more other heteroatoms or groups chosen selected from N, O, S, S(O)$_2$, and C(O), the heterocycle being optionally substituted, and/or
  $R_2$, $R_3$, $R_4$, $R_5$, $R'_2$, $R'_3$, $R'_4$, and $R'_5$ form, in pairs with adjacent radicals, an optionally substituted, saturated or unsaturated (hetero)cycle;
    wherein when the compound of formula (I) and/or (II) is positively charged, then it comprises as many anionic counterions as cationic charges to achieve the electrical neutrality of the molecule; and
  composition (2) is aqueous, and comprises one or more ingredients chosen from:
    i) hydrotropic solvents;
    ii) anionic surfactants, cationic surfactants, nonionic surfactants, amphoteric or zwitterionic surfactants, or mixtures of two or more thereof;
    iii) anionic polymers, cationic polymers, nonionic polymers, amphoteric or zwitterionic polymers, any of which may be optionally associative, or optionally substantive, or mixtures of two or more thereof;
  wherein composition (2) does not comprise any dye (I) or (II).

* * * * *

UNITED STATES PATENT AND TRADEMARK OFFICE
CERTIFICATE OF CORRECTION

| | | |
|---|---|---|
| PATENT NO. | : 11,896,700 B2 | |
| APPLICATION NO. | : 16/311519 | |
| DATED | : February 13, 2024 | |
| INVENTOR(S) | : Arnaud Bonnamy et al. | |

It is certified that error appears in the above-identified patent and that said Letters Patent is hereby corrected as shown below:

In the Claims

Claim 4, Column 71, Line 5, please remove "selected.".

Claim 7, Column 72, Line 49, please delete the second "2''" and insert -- 2''' --.

Signed and Sealed this
Seventh Day of May, 2024

*Katherine Kelly Vidal*

Katherine Kelly Vidal
*Director of the United States Patent and Trademark Office*